(12) United States Patent  
Fliri et al.

(10) Patent No.: US 8,686,043 B2  
(45) Date of Patent: Apr. 1, 2014

(54) HETEROCYCLIC SULFONAMIDES, USES AND PHARMACEUTICAL COMPOSITIONS THEREOF

(75) Inventors: Anton Franz Joseph Fliri, Stonington, CT (US); Randall James Gallaschun, Lebanon, CT (US); Christopher John O'Donnell, Mystic, CT (US); Jacob Bradley Schwarz, San Ramon, CA (US); Barbara Eileen Segelstein, Gales Ferry, CT (US)

(73) Assignee: Pfizer Inc., New York, NY (US)

( * ) Notice: Subject to any disclaimer, the term of this patent is extended or adjusted under 35 U.S.C. 154(b) by 138 days.

(21) Appl. No.: 13/596,492

(22) Filed: Aug. 28, 2012

(65) Prior Publication Data

US 2012/0322823 A1 Dec. 20, 2012

Related U.S. Application Data

(62) Division of application No. 12/823,224, filed on Jun. 25, 2010, now Pat. No. 8,278,457.

(60) Provisional application No. 61/220,625, filed on Jun. 26, 2009.

(51) Int. Cl.
| | |
|---|---|
| *A01N 41/06* | (2006.01) |
| *A61K 31/18* | (2006.01) |
| *A01N 43/06* | (2006.01) |
| *A61K 31/38* | (2006.01) |

(52) U.S. Cl.  
USPC .......................... 514/601; 514/444; 514/438

(58) Field of Classification Search  
USPC ......................................... 514/601, 444, 438  
See application file for complete search history.

(56) References Cited

U.S. PATENT DOCUMENTS

2003/0073708 A1  4/2003  Castelhano et al. ....... 514/265.1

FOREIGN PATENT DOCUMENTS

| EP | 1101755 | 5/2001 | ............ C07C 235/38 |
|---|---|---|---|
| WO | WO0190056 | 11/2001 | ............ C07C 303/44 |
| WO | WO2007090840 | 8/2007 | ............ C07D 307/22 |
| WO | WO2009092713 | 7/2009 | ............ C07C 311/08 |
| WO | WO2010038167 | 4/2010 | ............ C07D 211/76 |
| WO | WO2010041162 | 4/2010 | ............ C07D 307/22 |

OTHER PUBLICATIONS

Bleakman, D., et al., "Neuropharmacology of AMPA and kainite receptors", 1998, Neuropharmacology, pp. 1187-1204, 37(10-11).
Black, M.D., "Therapeutic Potential of Positive AMPA Modulators and Their Relationship to AMPA Receptor Subunits. A Review of Preclinical Data", 2005, Psychopharmacology, pp. 154-163, vol. 179.
Rogers, B., et al., "Novel Approaches for the Treatment of Schizophrenia", 2006, Annual Reports in Medicinal Chemistry, pp. 3-21, vol. 41.
Suzuki, A., "Recent advances in the cross-coupling reactions of organoboron derivatives with organic electrophiles, 1995-1998", 1999, Journal of Organometallic Chemistry, pp. 147-169, 576(1-2).
Miyaura, et al., "Palladium-Catalyzed Cross-Coupling Reactions of Organoboron Compounds", 1995, Chemical Reviews, pp. 2457-2483, 95(7).
Withbroe, G.J., et al., "Streamlined synthesis of the Bippyphos Family of Ligands and Cross-Coupling Applications", 2008, Organic Process Research and Development., pp. 480-489, 12(3).
Finnin, B.C., et al., "Transdermal Penetration Enhancers: Applications, Limitations, and Potential", Oct. 1999, Journal of Pharmaceutical Sciences, pp. 955-958, 88(10).
Flack, H.D., "On Enantiomorph-Polarity Estimation", 1983, Acta Cryst, pp. 876-881, vol. A39.
Madsen. P., et al., "Optimization of Alkylidene Hydrazide Based Human Glucagon Receptor Antagonists. Discovery of the Highly Potent and Orally Available 3-Cyano-4-hydroxybenzoic Acid [1-(2,3,5,6-Tetramethylbenzyl)-1*H*-indo-4-ylmethylene]hydrazide", 2002, Journal Medicinal Chemistry, pp. 5755-5775, vol. 45.
Johnson, D.C., et al., "A reversible safety-catch method for the hydrogenolysis of *N*-benzyl moieties", 2004, Tetrahedron Letters, pp. 8483-8487, 45(46).
Kawaguchi, K., et al., "Synthesis of Ladder-Type π-Conjugated Heteroacenes via Palladium-Catalyzed Double N-Arylation and Intramolecular O-Arylation", 2007, Journal of Organic Chemistry, pp. 5119-5128, 72(14).
Huang, X., et al., "Expanding Pd-Catalyzed C-N Bond-Forming Processes: The First Amidation of Aryl Sulfonates, Aqueous Amination, and Complementarity with Cu-Catalyzed Reactions", May 7, 2003, Journal of the American Chemical Society, pp. 6653-6655, 125(22).

(Continued)

*Primary Examiner* — Samira Jean-Louis  
(74) *Attorney, Agent, or Firm* — Feng Shao

(57) ABSTRACT

The invention is directed to a class of compounds, including the pharmaceutically acceptable salts of the compounds, having the structure of formula I:

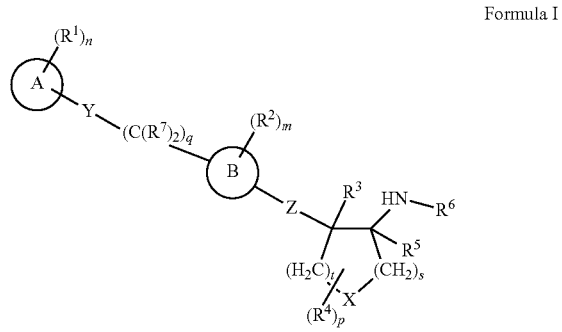

Formula I as defined in the specification. The invention is also directed to compositions containing and uses of the compounds of formula I.

18 Claims, No Drawings

(56) References Cited

OTHER PUBLICATIONS

Roach, M.L., et al., "Methods for the Isolation and Maintenance of Murine Embryonic Stem Cells", 2002, Methods in Molecular Biology, pp. 1-16, vol. 185.

PCT/IB2010/052827, International Search Report, dated Dec. 1, 2010, 5 pages.

Marenco, S., et al., Therapeutic Potential of Positive AMPA Receptor Modulators in the Treatment of Neuropsychiatric Disorders, CNS Drugs, 20 (3): 173-185, 2006.

Wezenberg, E., et al., Acute Effects of the Ampakine Farampator on Memory and Information Processing in Healthy Elderly Volunteers, Neuropsychopharmacology, 32: 1272-1283, 2007.

HETEROCYCLIC SULFONAMIDES, USES AND PHARMACEUTICAL COMPOSITIONS THEREOF

This application is a divisional of U.S. patent application Ser. No. 12/823,224, filed Jun. 25, 2010, now pending, which in turn claims the benefit of priority to U.S. Provisional Patent Application Ser. No. 61/220,625 filed Jun. 26, 2009, the disclosure of each of these two applications is hereby incorporated by reference in its entirety.

FIELD OF THE INVENTION

The present invention relates to a novel class of compounds having the structure of formula I as defined herein and pharmaceutical compositions comprising a compound of formula I or a pharmaceutically acceptable salt thereof. The present invention also comprises methods of treating a subject by administering a therapeutically effective amount of a compound of formula I or a pharmaceutically acceptable salt thereof to the subject. These compounds are useful for the conditions disclosed herein. The present invention further comprises methods for making the compounds of formula I and corresponding intermediates.

BACKGROUND OF THE INVENTION

The primary excitatory neurotransmitter in the mammalian central nervous system (CNS) is the amino acid glutamate whose signal transduction is mediated by either ionotropic or metabotropic glutamate receptors (GluR). Ionotropic glutamate receptors (iGluR) are comprised of three subtypes differentiated by their unique responses to the three selective iGluR agonists α-amino-3-hydroxy-5-methylisoxazole-4-propionic acid (AMPA), N-methyl-D-aspartate (NMDA) and kainate (Parsons, C. G., Danysz, W. and Lodge, D. (2002), in: *Ionotropic Glutamate Receptors as Therapeutic Targets* (Danysz, W., Lodge, D. and Parsons, C. G. eds), pp 1-30, F.P. Graham Publishing Co., Tennessee). AMPA receptors, proteinaceous homo- or heterotetramers comprised of any combination of four ca. 900 amino acid monomer subunits each encoded from a distinct gene ($Glu_{A1-A4}$) with each subunit protein existing as one of two splice variants deemed "flip" and "flop", mediate the vast majority of excitatory synaptic transmissions in the mammalian brain and have long been proposed to be an integral component of the neural circuitry that mediates cognitive processes (Bleakman, D. and Lodge, D. (1998) Neuropharmacology of AMPA and Kainate Receptors. *Neuropharmacology* 37:1187-1204). The combination of various heterotetrameric possibilities, two splice forms for each of the four iGluR monomers and receptor subunit RNA editing with the heterogeneous distribution of AMPA receptors throughout the brain highlight the myriad of potential AMPA receptor responses within this organ (Black, M. D. (2005) Therapeutic Potential of Positive AMPA Modulators and Their Relationship to AMPA Receptor Subunits. A Review of Preclinical Data. *Psychopharmacology* 179:154-163). AMPA modulators have now become an active target for drug discovery (see Rogers, B. and Schmidt, C., (2006) Novel Approaches for the Treatment of Schizophrenia, Annual Reports in Medicinal Chemistry 3-21).

SUMMARY OF THE INVENTION

The present invention is directed to compounds, including the pharmaceutically acceptable salts of the compounds, having the structure of formula:

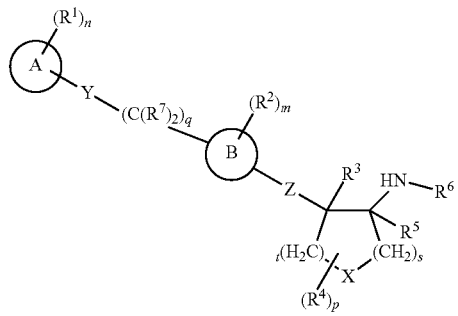

wherein each $R^1$ and each $R^2$ and each $R^7$ is independently selected from the group consisting of hydrogen, halogen, hydroxyl, —$CF_3$, —CN, —(C═O)$R^8$, —O—(C═O)—$R^8$, —(N$R^8$)—(C═O)—$R^8$, —(C═O)—O$R^8$, —(C═O)—N($R^8$)$_2$, —O$R^8$, —O—(C═O)—O$R^8$, —O—(C═O)—N($R^8$)$_2$, —$NO_2$, —N($R^8$)$_2$, —(N$R^8$)—$SO_2$—$R^8$, —S(O)$_w$$R^8$, —$SO_2$—N(R)$_2$, ($C_1$-$C_6$)alkyl, ($C_6$-$C_{10}$)aryl, ($C_1$-$C_9$)heteroaryl, ($C_1$-$C_9$)heterocycloalkyl, and ($C_3$-$C_{10}$)cycloalkyl; wherein said ($C_1$-$C_6$)alkyl, ($C_6$-$C_{10}$)aryl, ($C_1$-$C_9$)heteroaryl, ($C_1$-$C_9$)heterocycloalkyl, or ($C_3$-$C_{10}$)cycloalkyl are each independently optionally substituted with one, two, three or four $R^9$;

w is 0, 1 or 2;
m is zero, one, two or three;
n is zero, one, two or three;
p is zero, one, two or three;
q is zero, one, two or three;
s is one and t is one; or one of s or t is one and the other of s or t is two;

$R^3$ is hydrogen or ($C_1$-$C_6$)alkyl;

each $R^4$ is independently selected from hydrogen, or ($C_1$-$C_6$)alkyl; wherein said ($C_1$-$C_6$)alkyl may be optionally substituted with one, two, three or four halogen, —CN, or —O$R^9$;

or two $R^4$ groups on the same carbon atom may be taken together to form an oxo (═O) radical or a ($C_3$-$C_6$)spirocycloalkyl;

$R^5$ is hydrogen, or ($C_1$-$C_6$)alkyl;

$R^6$ is ($C_1$-$C_6$)alkyl-(C═O)—, [($C_1$-$C_6$)alkyl]$_2$N—(C═O)—, ($C_1$-$C_6$)alkyl-$SO_2$—, ($C_3$-$C_{10}$)cycloalkyl-$SO_2$—, or [($C_1$-$C_6$)alkyl]$_2$N—$SO_2$—; wherein said ($C_1$-$C_6$)alkyl moieties of said [($C_1$-$C_6$)alkyl]$_2$N—(C═O)— and [($C_1$-$C_6$) alkyl]$_2$N—$SO_2$— may optionally be taken together with the nitrogen atom to which they are attached to form a three to six membered heterocyclic ring;

each $R^8$ is independently selected from the group consisting of hydrogen, ($C_1$-$C_6$)alkyl, ($C_6$-$C_{10}$)aryl, ($C_1$-$C_9$)heteroaryl, ($C_1$-$C_9$)heterocycloalkyl, and ($C_3$-$C_{10}$)cycloalkyl; wherein said ($C_1$-$C_6$)alkyl may be optionally substituted with one, two or three substituents independently selected from hydrogen, halo, —CN, perfluoro($C_1$-$C_6$)alkyl, hydroxy, amino, ($C_1$-$C_6$)alkylamino, [($C_1$-$C_6$)alkyl]$_2$-amino, ($C_1$-$C_6$)alkoxy, perfluoro($C_1$-$C_6$)alkoxy, HO—(C═O)—, ($C_1$-$C_6$) alkyl-O—(C═O)—, formyl, ($C_1$-$C_6$)alkyl-(C═O)—, $H_2$N—(C═O)—, ($C_1$-$C_6$)alkyl]-(NH)—(C═O)—, [($C_1$-$C_6$)alkyl]$_2$N—(C═O)—, ($C_1$-$C_6$)alkyl-(C═O)—O—, H(C═O)—NH—, ($C_1$-$C_6$)alkyl(C═O)—NH—, ($C_1$-$C_6$) alkyl(C═O)—O—[N(($C_1$-$C_6$)alkyl)]-, ($C_1$-$C_6$)alkyl-$SO_2$—, ($C_1$-$C_6$)alkyl-$SO_2$—NH—, ($C_1$-$C_6$)alkyl-$SO_2$— [N(($C_1$-$C_6$) alkyl)]-, $H_2$N—$SO_2$—, [($C_1$-$C_6$)alkyl]-NH—$SO_2$—, and [($C_1$-$C_6$)alkyl]$_2$N—$SO_2$—; wherein said ($C_1$-$C_6$)alkyl may be additionally optionally substituted with an optionally substituted $(C_6\text{-}C_{10})$aryl, $(C_1\text{-}C_9)$heteroaryl, $(C_1\text{-}C_9)$heterocycloalkyl, or $(C_3\text{-}C_{10})$cycloalkyl; wherein said optional substituents may be independently selected from one, two, three or four radicals independently selected from halogen, hydroxyl, —$CF_3$, —CN, $(C_1\text{-}C_3)$alkyl, $(C_1\text{-}C_3)$alkoxy, and amino; wherein each of said $R^8$ $(C_6\text{-}C_{10})$aryl, $(C_1\text{-}C_9)$heteroaryl, $(C_1\text{-}C_9)$heterocycloalkyl or $(C_3\text{-}C_{10})$cycloalkyl substituents may be optionally additionally substituted with one, two, three or four radicals independently selected from halogen, hydroxyl, —$CF_3$, —CN, $(C_1\text{-}C_3)$alkyl, $(C_1\text{-}C_3)$alkoxy and amino;

each $R^9$ is independently selected from the group consisting of halogen, hydroxyl, —$CF_3$, —CN, —(C=O)$R^{10}$, —O—(C=O)—$R^{10}$, —(N$R^{10}$)—(C=O)—$R^{10}$, —(C=O)—O$R^{10}$, —(C=O)—N($R^{10}$)$_2$, —O$R^{10}$, —O—(C=O)—O$R^{10}$, —O—(C=O)—N($R^{10}$)$_2$, —NO$_2$, —N($R^{10}$)$_2$, —(N$R^{10}$)—SO$_2$—$R^{10}$, —S(O)$_u R^{10}$, and —SO$_2$—N($R^{10}$)$_2$;

each $R^{10}$ is independently selected from the group consisting of hydrogen, $(C_1\text{-}C_6)$alkyl, $(C_6\text{-}C_{10})$aryl, $(C_1\text{-}C_9)$heteroaryl, $(C_1\text{-}C_9)$heterocycloalkyl and $(C_3\text{-}C_{10})$cycloalkyl; wherein said $(C_1\text{-}C_6)$alkyl may be optionally substituted with one, two or three substituents independently selected from hydrogen, halo, —CN, perfluoro$(C_1\text{-}C_6)$alkyl, hydroxy, amino, $(C_1\text{-}C_6)$alkylamino, [$(C_1\text{-}C_6)$alkyl]$_2$-amino, $(C_1\text{-}C_6)$alkoxy, perfluoro$(C_1\text{-}C_6)$alkoxy, HO—(C=O)—, $(C_1\text{-}C_6)$alkyl-O—(C=O)—, formyl, $(C_1\text{-}C_6)$alkyl-(C=O)—, H$_2$N—(C=O)—, $(C_1\text{-}C_6)$alkyl]-(NH)—(C=O)—, [$(C_1\text{-}C_6)$alkyl]$_2$N—(C=O)—, $(C_1\text{-}C_6)$alkyl-(C=O)—O—, H(C=O)—NH—, $(C_1\text{-}C_6)$alkyl(C=O)—NH—, $(C_1\text{-}C_6)$alkyl(C=O)—[N(($C_1\text{-}C_6$)alkyl)]-, $(C_1\text{-}C_6)$alkyl-SO$_2$—, $(C_1\text{-}C_6)$alkyl-SO$_2$—NH—, $(C_1\text{-}C_6)$alkyl-SO$_2$— [N(($C_1\text{-}C_6$)alkyl)]-, H$_2$N—SO$_2$—, [$(C_1\text{-}C_6)$alkyl]-NH—SO$_2$—, and [$(C_1\text{-}C_6)$alkyl]$_2$N—SO$_2$—; wherein said $(C_1\text{-}C_6)$alkyl may also be additionally optionally substituted with an optionally substituted $(C_6\text{-}C_{10})$aryl, $(C_1\text{-}C_9)$heteroaryl, $(C_1\text{-}C_9)$heterocycloalkyl or $(C_3\text{-}C_{10})$cycloalkyl; wherein said optional substituents may be independently selected from one, two, three or four radicals independently selected from halogen, hydroxyl, —$CF_3$, —CN, $(C_1\text{-}C_3)$alkyl, $(C_1\text{-}C_3)$alkoxy, and amino; wherein each of said $R^{10}$ $(C_6\text{-}C_{10})$aryl, $(C_1\text{-}C_9)$heteroaryl, $(C_1\text{-}C_9)$heterocycloalkyl, or $(C_3\text{-}C_{10})$cycloalkyl substituents may be optionally additionally substituted with one, two, three or four radicals independently selected from halogen, hydroxyl, —$CF_3$, —CN, $(C_1\text{-}C_3)$alkyl, $(C_1\text{-}C_3)$alkoxy, and amino;

$R^{11}$ is hydrogen or $(C_1\text{-}C_6)$alkyl;

ring "A" is $(C_6\text{-}C_{10})$aryl, $(C_1\text{-}C_9)$heteroaryl, $(C_4\text{-}C_{10})$cycloalkyl, or $(C_1\text{-}C_9)$heterocycloalkyl; wherein two of said $R^1$ substituents on said $(C_4\text{-}C_{10})$cycloalkyl and $(C_1\text{-}C_9)$heterocycloalkyl may optionally be attached to the same carbon atom and may optionally be taken together to be oxo;

ring "B" is $(C_6\text{-}C_{10})$aryl, $(C_1\text{-}C_9)$heteroaryl, $(C_4\text{-}C_{10})$cycloalkyl, or $(C_1\text{-}C_9)$heterocycloalkyl;

"X" is —O— or >C($R^4$)$_2$;

"Y" is >N$R^{11}$, —(N$R^{11}$)—(C=O)—, >C=O, —O— or >C($R^7$)$_2$; and

"Z" is —O—, —S—, —(S=O)—, or —(SO$_2$)—.

The term "alkyl" refers to a linear or branched-chain saturated, mono-unsaturated and poly-unsaturated hydrocarbyl substituent (i.e., a substituent obtained from a hydrocarbon by removal of a hydrogen) containing from one to six carbon atoms; and in another embodiment, from one to four carbon atoms. Mono- and poly-unsaturated substituents, a so called alkenyl, has 2 to 6 carbon atoms. The alkenyl group may exist as the pure E (entgegen) form, the pure Z (zusammen) form, or any mixture thereof. Poly-unsaturated includes multiple double bonds and one or more triple bonds. Such triple bond containing alkyl grops, a so called alkynyl group, has 2 to 6 carbon atoms. Examples of such saturated substituents include methyl, ethyl, propyl (including n-propyl and isopropyl), butyl (including n-butyl, isobutyl, sec-butyl and tert-butyl), pentyl, iso-amyl, hexyl and the like. Examples of unsaturated alkyl include ethenyl, 1-propenyl, 2-propenyl(allyl), iso-propenyl, 2-methyl-1-propenyl, 1-butenyl, 2-butenyl, and the like. Examples of alkynyl include ethynyl, propynyl, butynyl, 3,3-dimethylbutynyl and the like.

In some instances, the number of carbon atoms in a hydrocarbyl substituent (e.g., alkyl, alkenyl, cycloalkyl, cycloalkenyl, aryl, etc.) is indicated by the prefix "$C_x$-$C_y$-," wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl refers to saturated cycloalkyl containing from 3 to 6 carbon ring atoms.

As used herein, the term "perfluoro($C_1$-$C_6$)alkyl" refers to an alkyl radical as described above substituted with one or more fluorine's including, but not limited to, fluoromethyl, difluoromethyl, trifluoromethyl, 2,2,2-trifluoroethyl, and the like.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents include, for example, alcohols, enols and phenol.

The term "cyano" (also referred to as "nitrile") means —CN, which also may be depicted as —C≡N.

The term "carbonyl" means —C(O)—, >C=O, —(C=O)—, and which also may be depicted as:

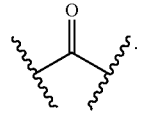

The term "amino" refers to —NH$_2$.

The term "oxo" refers to =O.

The term "alkoxy" refers to an alkyl linked to an oxygen, which may also be represented as: —O—R, wherein the R represents the alkyl group. Examples of alkoxy include methoxy, ethoxy, propoxy and butoxy.

The term "sulfonyl" refers to —S(O)$_2$—, which also may be depicted as:

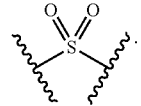

Thus, for example, "alkyl-sulfonyl-alkyl" refers to alkyl-S(O)$_2$-alkyl. Examples of alkylsulfonyl include methylsulfonyl, ethylsulfonyl, and propylsulfonyl.

As used herein, the term "cycloalkyl" is defined to include saturated or unsaturated (non aromatic), bridged, polycyclic, spirocyclic or fused polycyclic 3 to 10 membered hydrocarbon rings (e.g., cyclopropyl, cyclobutyl, cyclopentyl, cyclohexyl, cycloheptyl, cyclooctyl, cyclononyl, bicyclo[2.2.1]heptanyl, bicyclo[3.2.1]octanyl and bicyclo[5.2.0]nonanyl, etc.); optionally substituted by 1 to 5 suitable substituents. Preferably, the cycloalkyl group has 3 to 6 carbon atoms. In one embodiment the cycloalkyl may optionally contain one, two or more non cumulative non aromatic double or triple bonds. Spirocyclic rings are one particular kind of cycloalkyl that occurs when a ring is formed around one carbon atom as compared to a fused ring in which a ring is formed through two common carbon atoms.

As used herein, the term "aryl" is defined to include all-carbon monocyclic or fused-ring polycyclic (i.e., rings which share adjacent pairs of carbon atoms) groups having a completely conjugated pi-electron system. The aryl group has 6, 8, 9 or 10 carbon atoms in the ring(s). More preferably, the aryl group has 6 or 10 carbon atoms in the ring(s). Most preferably, the aryl group has 6 carbon atoms in the ring(s). For example, as used herein, the term "($C_6$-$C_{10}$)aryl" means aromatic radicals containing from 6 to 10 carbon atoms such as phenyl, naphthyl, tetrahydronaphthyl, anthracenyl, indanyl and the like. The aryl group is optionally substituted by 1 to 5 suitable substituents.

As used herein, the term "heteroaryl" is defined to include monocyclic or fused-ring polycyclic aromatic heterocyclic groups with one or more heteroatoms selected from O, S and N in one or more of said ring(s). The heteroaryl group has 5 to 12 ring atoms including one to five heteroatoms independently selected from O, S, and N. One or more of said rings of said heterocyclic group may contain no heteroatoms. Preferably, the heteroaryl group has 5 to 10 ring atoms including one to four heteroatoms. More preferably, the heteroaryl group has 5 to 8 ring atoms including one, two or three heteroatoms. Most preferably, the heteroaryl group has 6 to 8 ring atoms including one or two heteroatoms. For example, as used herein, the term "($C_1$-$C_9$)heteroaryl" means aromatic radicals containing at least one ring heteroatom independently selected from O, S and N and from 1 to 9 carbon atoms such as pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like. The heteroaryl group is optionally substituted by 1 to 5 suitable substituents.

As used herein, the term "heterocycloalkyl" is defined to include a monocyclic, bridged, polycyclic, spirocyclic or fused polycyclic saturated or unsaturated non-aromatic 3 to 20 membered ring including 1 or more heteroatoms independently selected from O, S and N. One or more of said rings of said bridged, polycyclic or fused heterocyclic group may contain no heteroatoms. Examples of such heterocycloalkyl rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, and the like. Further examples of said heterocycloalkyl rings are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2 pyrazolidin-2-yl, 1,3-pyrazolidin-1-yl, 1,2-tetrahydrothiazin-2-yl, 1,3 tetrahydrothiazin-3-yl, 1,2-tetrahydrodiazin-2-yl, 1,3 tetrahydrodiazin-1-yl, 1,4-oxazin-2-yl, 1,2,5-oxathiazin-4-yl and the like. The heterocycloalkyl ring is optionally substituted by 1 to 5 suitable substituents.

If substituents are described as being "independently selected" from a group, each substituent is selected independent of the other. Each substituent therefore may be identical to or different from the other substituent(s).

When an asymmetric center is present in a compound of formula I (hereinafter understood to mean formula I, Ia, Ib, Ic, Id or Ie), hereinafter referred to as a "compound of the invention," the compound may exist in the form of optical isomers (enantiomers). In one embodiment, the present invention comprises enantiomers and mixtures, including racemic mixtures of the compounds of formula I. In another embodiment, for compounds of formula I that contain more than one asymmetric center, the present invention comprises diastereomeric forms (individual diastereomers and mixtures thereof) of compounds. When a compound of formula I contains an alkenyl group or moiety, geometric isomers may arise.

The present invention comprises the tautomeric forms of compounds of formula I. Where structural isomers are interconvertible via a low energy barrier, tautomeric isomerism ('tautomerism') can occur. This can take the form of proton tautomerism in compounds of formula I containing, for example, an imino, keto, or oxime group, or so-called valence tautomerism in compounds which contain an aromatic moiety. It follows that a single compound may exhibit more than one type of isomerism. The various ratios of the tautomers in solid and liquid form is dependent on the various substituents on the molecule as well as the particular crystallization technique used to isolate a compound.

Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclylic, carboxylic, and sulfonic classes of organic acids.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

In one embodiment, hemisalts of acids and bases may also be formed, for example, hemisulphate and hemicalcium salts.

The present invention also includes isotopically labelled compounds, which are identical to those recited in formula I, but for the fact that one or more atoms are replaced by an atom having an atomic mass or mass number different from the atomic mass or mass number usually found in nature.

Examples of isotopes that may be incorporated into compounds of the present invention include isotopes of hydrogen, carbon, nitrogen, oxygen, phosphorous, sulfur, fluorine and chlorine, such as $^2H$, $^3H$, $^{13}C$, $^{11}C$, $^{14}C$, $^{15}N$, $^{18}O$, $^{17}O$, $^{31}P$, $^{32}P$, $^{35}S$ $^{18}F$, and $^{36}Cl$, respectively. Compounds of the present invention, and pharmaceutically acceptable salts of said compounds or which contain the aforementioned isotopes and/or other isotopes of other atoms are within the scope of this invention. Certain isotopically labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, may afford certain therapeutic advantages resulting from greater metabolic stability, for example increased in vivo half-life or reduced dosage requirements and, hence, may be preferred in some circumstances. Isotopically labelled compounds of formula I of this invention may generally be prepared by carrying out the procedures disclosed in the Schemes and/or in the Examples and Preparations below, by substituting a readily available isotopically labelled reagent for a non-isotopically labelled reagent.

One embodiment of the present invention relates to compounds of the Formula:

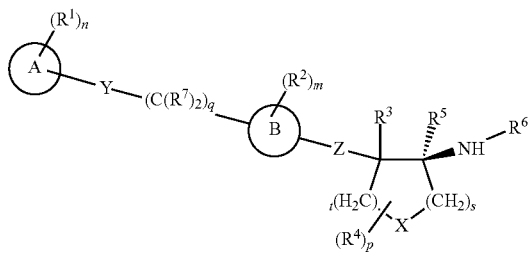

Ia

Another embodiment of the present invention relates to compounds of the Formula:

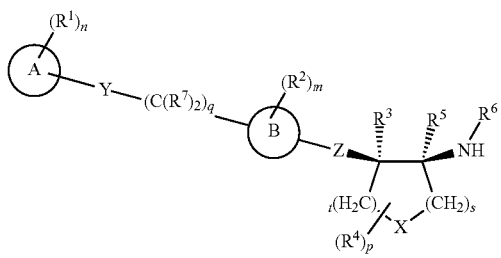

Ib

One skilled in the art will appreciate that compounds of formula I can exist as alternate stereoisomers including the following:

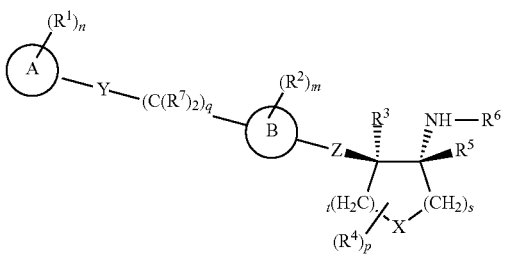

Ic

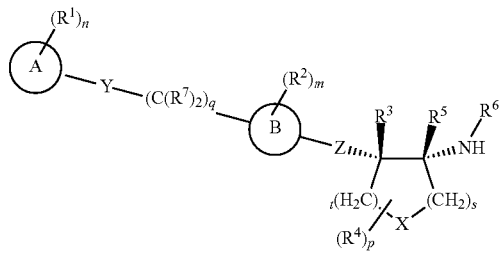

Id

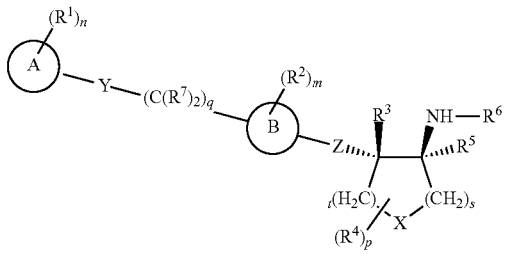

Ie

Another embodiment of the present invention (the so called ethers) relates to compounds of the Formula I (or Ia, Ib, Ic, Id or Ie), wherein "Z" is —O—.

Another embodiment of the present invention (the so called thioethers) relates to a compound of the Formula I (or Ia, Ib, Ic, Id or Ie), wherein "Z" is —S—.

Another embodiment of the present invention (the so called sulfoxides) relates to a compound of the Formula I (or Ia, Ib, Ic, Id or Ie), wherein "Z" is —(S═O)—.

Another embodiment of the present invention (the so called sulfones) relates to a compound of the Formula I (or Ia, Ib, Ic, Id or Ie), wherein "Z" is —(SO$_2$)—.

Another embodiment of the present invention (the so called furans or pyrans) relate to compounds of the Formula I (or Ia, Ib, Ic, Id or Ie), wherein X is —O—. The present inventors have a particular interest is these furans and pyrans particularly as they can be segregated according to combinations with other embodiments of which the "Z" embodiments are of particular note.

Another embodiment of the present invention (the so called cyclopentyls or cyclohexyls) relate to compounds of the Formula I (or Ia, Ib, Ic, Id or Ie), wherein X is >C(R$^4$)$_2$, more specifically wherein each R$^4$ is hydrogen. The present inventors also have a particular interest is these cyclopentyls or cyclohexyls particularly as they can be segregated according to combinations with other embodiments of which the "Z" embodiments are of particular note.

Another embodiment of the present invention relates to a compound of the Formula I (or Ia, Ib, Ic, Id or Ie), wherein ring "A" is phenyl; more specifically wherein n is zero, one or two; more specifically wherein R$^1$ is selected from the group consisting of hydrogen, halogen, hydroxyl, —CF$_3$, —CN, —(C═O)R$^8$, —O—(C═O)—R$^8$, —(NR$^8$)—(C═O)—R$^8$, —(C═O)—OR$^8$, —(C═O)—N(R$^8$)$_2$, —OR$^8$, —O—(C═O)—OR$^8$, —O—(C═O)—N(R$^8$)$_2$, —NO$_2$, —N(R$^8$)$_2$, —(NR$^8$)—SO$_2$—R$^8$, —S(O)$_w$R$^8$, —SO$_2$—N(R$^8$)$_2$, and (C$_1$-C$_6$)alkyl; wherein said (C$_1$-C$_6$)alkyl is optionally substituted with one, two, three or four R$^9$. The present inventors also have a particular interest in these "A" phenyl compounds particularly as they can be segregated according to combinations with other embodiments of which the "cyclopentyls" or "cyclohexyls" and/or the "Z" embodiments are of particular note.

Another embodiment of the present invention relates to a compound of the Formula I (or Ia, Ib, Ic, Id or Ie), wherein ring "A" is ($C_1$-$C_9$)heteroaryl; more specifically wherein n is zero, one or two; and more specifically wherein $R^1$ is selected from the group consisting of hydrogen, halogen, hydroxyl, —$CF_3$, —CN, —(C=O)$R^8$, —O—(C=O)—$R^8$, —(N$R^8$)—(C=O)—$R^8$, —(C=O)—O$R^8$, —(C=O)—N($R^8$)$_2$, —O$R^8$, —O—(C=O)—O$R^8$, —O—(C=O)—N($R^8$)$_2$, —$NO_2$, —N($R^8$)$_2$, —(N$R^8$)—$SO_2$—$R^8$, —S(O)$_w$$R^8$, —$SO_2$—N($R^8$)$_2$, and ($C_1$-$C_6$)alkyl; wherein said ($C_1$-$C_6$)alkyl is optionally substituted with one, two, three or four $R^9$. The present inventors also have a particular interest is these "A" ($C_1$-$C_9$)heteroaryl compounds particularly as they can be segregated according to combinations with other embodiments of which the "X" "cyclopentyls" or "cyclohexyls" and/or the "Z" embodiments are of particular note.

Another embodiment of the present invention relates to a compound of the Formula I (or Ia, Ib, Ic, Id or Ie), wherein ring "A" is ($C_1$-$C_9$)heterocycloalkyl; more specifically wherein n is zero, one or two; and more specifically wherein $R^1$ is selected from the group consisting of oxo, hydrogen, halogen, hydroxyl, —$CF_3$, —CN, —(C=O)$R^8$, —O—(C=O)—$R^8$, —(N$R^8$)—(C=O)—$R^8$, —(C=O)—O$R^8$, —(C=O)—N($R^8$)$_2$, —O$R^8$, —O—(C=O)—O$R^8$, —O—(C=O)—N($R^8$)$_2$, —$NO_2$, —N($R^8$)$_2$, —(N$R^8$)—$SO_2$—$R^8$, —S(O)$_w$$R^8$, —$SO_2$—N($R^8$)$_2$, and ($C_1$-$C_6$)alkyl; wherein said ($C_1$-$C_6$)alkyl is optionally substituted with one, two, three or four $R^9$. The present inventors also have a particular interest in these "A" ($C_1$-$C_9$)heterocycloalkyl compounds particularly as they can be segregated according to combinations with other embodiments of which the "X" "cyclopentyls" or "cyclohexyls" and/or the "Z" embodiments are of particular note.

Another embodiment of the present invention relates to a compound of the Formula I (or Ia, Ib, Ic, Id or Ie), wherein ring "A" is ($C_4$-$C_{10}$)cycloalkyl; more specifically wherein n is zero, one or two; and more specifically wherein $R^1$ is selected from the group consisting of oxo, hydrogen, halogen, hydroxyl, —$CF_3$, —CN, —(C=O)$R^8$, —O—(C=O)—$R^8$, —(N$R^8$)—(C=O)—$R^8$, —(C=O)—O$R^8$, —(C=O)—N($R^8$)$_2$, —O$R^8$, —O—(C=O)—O$R^8$, —O—(C=O)—N($R^8$)$_2$, —$NO_2$, —N($R^8$)$_2$, —(N$R^8$)—$SO_2$—$R^8$, —S(O)$_w$$R^8$, —$SO_2$—N($R^8$)$_2$, and ($C_1$-$C_6$)alkyl; wherein said ($C_1$-$C_6$)alkyl is optionally substituted with one, two, three or four $R^9$. The present inventors also have a particular interest is these "A" ($C_4$-$C_{10}$)cycloalkyl compounds particularly as they can be segregated according to combinations with other embodiments of which the "X" "cyclopentyls" or "cyclohexyls" and/or the "Z" embodiments are of particular note.

Another embodiment of the present invention relates to a compound of the Formula I (or Ia, Ib, Ic, Id or Ie), wherein $R^1$ is ($C_1$-$C_6$)alkoxy, ($C_1$-$C_6$)alkyl, cyano or halogen and is in the ortho or para position relative to Y.

Another embodiment of the present invention relates to a compound of the Formula I (or Ia, Ib, Ic, Id or Ie), wherein ring "B" is phenyl; more specifically wherein n is zero or one; more specifically wherein $R^2$ is hydrogen, halogen, hydroxyl, —$CF_3$, —CN, —(C=O)$R^8$, —O—(C=O)—$R^8$, —(N$R^8$)—(C=O)—$R^8$, —(C=O)—O$R^8$, —(C=O)—N($R^8$)$_2$, —O$R^8$, —O—(C=O)—O$R^8$, —O—(C=O)—N($R^8$)$_2$, —$NO_2$, —N($R^8$)$_2$, —(N$R^8$)—$SO_2$—$R^8$, —S(O)$_w$$R^8$, —$SO_2$—N($R^8$)$_2$, and ($C_1$-$C_6$)alkyl; wherein said ($C_1$-$C_6$)alkyl is optionally substituted with one, two, three or four $R^9$. The present inventors also have a heightened particular interest in these "B" phenyl compounds particularly as they can be segregated according to combinations with other embodiments of which the "X" "cyclopentyls" or "cyclohexyls" and/or the "Z" embodiments are of particular note. Each of these embodiments also form additional embodiments of interest with the "A" ring embodiments described above.

Another embodiment of the present invention relates to a compound of the Formula I (or Ia, Ib, Ic, Id or Ie), wherein ring "B" is ($C_1$-$C_9$)heteroaryl; more specifically wherein n is zero or one; and more specifically wherein $R^2$ is hydrogen, halogen, hydroxyl, —$CF_3$, —CN, —(C=O)$R^8$, —O—(C=O)—$R^8$, —(N$R^8$)—(C=O)—$R^8$, —(C=O)—O$R^8$, —(C=O)—N($R^8$)$_2$, —O$R^8$, —O—(C=O)—O$R^8$, —O—(C=O)—N($R^8$)$_2$, —$NO_2$, —N($R^8$)$_2$, —(N$R^8$)—$SO_2$—$R^8$, —S(O)$_w$$R^8$, —$SO_2$—N($R^8$)$_2$, and ($C_1$-$C_6$)alkyl; wherein said ($C_1$-$C_6$)alkyl is optionally substituted with one, two, three or four $R^9$. The present inventors also have a heightened particular interest in these "B" ($C_1$-$C_9$)heteroaryl compounds particularly as they can be segregated according to combinations with other embodiments of which the "X" "cyclopentyls" or "cyclohexyls" and/or the "Z" embodiments are of particular note. Each of these embodiments also form additional embodiments of interest with the "A" ring embodiments described above.

Another embodiment of the present invention relates to a compound of the Formula I (or Ia, Ib, Ic, Id or Ie), wherein ring "B" is ($C_1$-$C_9$)heterocycloalkyl; more specifically wherein n is zero or one; and more specifically wherein $R^2$ is hydrogen, halogen, hydroxyl, —$CF_3$, —CN, —(C=O)$R^8$, —O—(C=O)—$R^8$, —(N$R^8$)—(C=O)—$R^8$, —(C=O)—O$R^8$, —(C=O)—N($R^8$)$_2$, —O$R^8$, —O—(C=O)—O$R^8$, —O—(C=O)—N($R^8$)$_2$, —$NO_2$, —N($R^8$)$_2$, —(N$R^8$)—$SO_2$—$R^8$, —S(O)$_w$$R^8$, —$SO_2$—N($R^8$)$_2$, and ($C_1$-$C_6$)alkyl; wherein said ($C_1$-$C_6$)alkyl is optionally substituted with one, two, three or four $R^9$. The present inventors also have a heightened particular interest in these "B" ($C_1$-$C_9$)heterocycloalkyl compounds particularly as they can be segregated according to combinations with other embodiments of which the "X" "cyclopentyls" or "cyclohexyls" and/or the "Z" embodiments are of particular note. Each of these embodiments also form additional embodiments of interest with the "A" ring embodiments described above.

Another embodiment of the present invention relates to a compound of the Formula I (or Ia, Ib, Ic, Id or Ie), wherein ring "B" is ($C_4$-$C_{10}$)cycloalkyl; more specifically wherein n is zero or one; and more specifically wherein $R^2$ is hydrogen, halogen, hydroxyl, —$CF_3$, —CN, —(C=O)$R^8$, —O—(C=O)—$R^8$, —(N$R^8$)—(C=O)—$R^8$, —(C=O)—O$R^8$, —(C=O)—N($R^8$)$_2$, —O$R^8$, —O—(C=O)—O$R^8$, —O—(C=O)—N($R^8$)$_2$, —$NO_2$, —N($R^8$)$_2$, —(N$R^8$)—$SO_2$—$R^8$, —S(O)$_w$$R^8$, —$SO_2$—N($R^8$)$_2$, and ($C_1$-$C_6$)alkyl; wherein said ($C_1$-$C_6$)alkyl is optionally substituted with one, two, three or four $R^9$. The present inventors also have a heightened particular interest in these "B" ($C_4$-$C_{10}$)cycloalkyl compounds particularly as they can be segregated according to combinations with other embodiments of which the "X" "cyclopentyls" or "cyclohexyls" and/or the "Z" embodiments are of particular note. Each of these embodiments also form additional embodiments of interest with the "A" ring embodiments described above.

Another embodiment of the present invention relates to a compound of the Formula I (or Ia, Ib, Ic, Id or Ie), wherein $R^2$ is ($C_1$-$C_6$)alkoxy, ($C_1$-$C_6$)alkyl, cyano or halogen.

Another embodiment of the present invention relates to a compound of the Formula I (or Ia, Ib, Ic, Id or Ie), wherein $R^2$ is hydrogen.

Another embodiment of the present invention relates to a compound of the Formula I (or Ia, Ib, Ic, Id or Ie), wherein $R^4$ is hydrogen.

Another embodiment of the present invention relates to a compound of the Formula I (or Ia, Ib, Ic, Id or Ie), wherein p is two and both $R^4$ are taken together to form oxo.

Another embodiment of the present invention relates to a compound of the Formula I (or Ia, Ib, Ic, Id or Ie), wherein p is two and each $R^4$ is $(C_1-C_6)$alkyl.

Another embodiment of the present invention relates to a compound of the Formula I (or Ia, Ib, Ic, Id or Ie), wherein q is zero.

Another embodiment of the present invention relates to a compound of the Formula I (or Ia, Ib, Ic, Id or Ie), wherein Y is absent.

Another embodiment of the present invention relates to a compound of the Formula I (or Ia, Ib, Ic, Id or Ie), wherein Y is —O—.

Another embodiment of the present invention relates to a compound of the Formula I (or Ia, Ib, Ic, Id or Ie), wherein Y is >C(R^7)_2$.

Another embodiment of the present invention relates to a compound of the Formula I (or Ia, Ib, Ic, Id or Ie), wherein $R^6$ is $(C_1-C_5)$alkyl-(C=O)—.

Another embodiment of the present invention relates to a compound of the Formula I (or Ia, Ib, Ic, Id or Ie), wherein $R^6$ is $[(C_1-C_3)alkyl]_2N$—(C=O)—, wherein said $(C_1-C_2)$alkyl moieties may optionally be taken together with the nitrogen atom to which they are attached to form a four to six membered heterocyclic ring.

Another embodiment of the present invention relates to a compound of the Formula I (or Ia, Ib, Ic, Id or Ie), wherein $R^6$ is $(C_1-C_5)$alkyl-$SO_2$—.

Another embodiment of the present invention relates to a compound of the Formula I (or Ia, Ib, Ic, Id or Ie), wherein $R^6$ is $(C_3-C_5)$cycloalkyl-$SO_2$—.

Another embodiment of the present invention relates to a compound of the Formula I (or Ia, Ib, Ic, Id or Ie), wherein $R^6$ is $[(C_1-C_3)alkyl]_2N$—$SO_2$—; wherein said $(C_1-C_2)$alkyl moieties may optionally be taken together with the nitrogen atom to which they are attached to form a four to six membered heterocyclic ring.

Another embodiment of the invention also relates to each of the individual compounds described as Examples 1-54 in the Examples section of this specification, and pharmaceutically acceptable salts thereof.

Specific preferred compounds of the invention include:
Propane-2-sulfonic acid [(3S,4S)-4-(2'-cyano-biphenyl-4-yloxy)-tetrahydro-furan-3-yl]-amide;
Propane-2-sulfonic acid [(3S,4S)-4-(2'-cyano-4'-fluoro-biphenyl-4-yloxy)-tetrahydro-furan-3-yl]-amide;
Propane-2-sulfonic acid [(3S,4S)-4-(2',4'-difluoro-biphenyl-4-yloxy)-tetrahydro-furan-3-yl]-amide;
Propane-2-sulfonic acid {(3S,4S)-4-[4-(5-cyano-thiophen-2-yl)-phenoxy]-tetrahydro-furan-3-yl}-amide;
Propane-2-sulfonic acid {(1S,2R)-2-[4-(5-cyano-thiophen-2-yl)-3-fluoro-phenoxy]-cyclopentyl}-amide;
Propane-2-sulfonic acid {(1S,2R)-2-[4-(5-cyano-thiophen-2-yl)-phenoxy]-cyclopentyl}-amide;
Propane-2-sulfonic acid {(1S,2R)-2-[3-fluoro-4-(2-methanesulfonylamino-ethyl)-phenoxy]-cyclopentyl}-amide;
Propane-2-sulfonic acid {(3S,4S)-4-[5-(2-cyano-phenyl)-pyridin-2-yloxy]-tetrahydro-furan-3-yl}-amide;
Propane-2-sulfonic acid {(1S,2R)-2-[6-(2-cyano-4-fluoro-phenyl)-pyridin-3-yloxy]-cyclohexyl}-amide; and
Propane-2-sulfonic acid {(1S,2R)-2-[6-(5-cyano-thiophen-2-yl)-pyridin-3-yloxy]-cyclohexyl}-amide;
or pharmaceutically acceptable salts thereof.

Other specific compounds of the invention, and the pharmaceutically acceptable salts thereof, include the following:
Propane-2-sulfonic acid [4-(4-benzyl-phenoxy)-tetrahydro-furan-3-yl]-amide;
Propane-2-sulfonic acid {4-[4-(1-phenyl-ethyl)-phenoxy]-tetrahydro-furan-3-yl}-amide;
Propane-2-sulfonic acid {4-[4-(hydroxy-phenyl-methyl)-phenoxy]-tetrahydro-furan-3-yl}-amide;
Propane-2-sulfonic acid [4-(4-benzoyl-phenoxy)-tetrahydro-furan-3-yl]-amide;
Propane-2-sulfonic acid [4-(4-phenoxymethyl-phenoxy)-tetrahydro-furan-3-yl]-amide;
Propane-2-sulfonic acid {4-[4-(pyrrolidine-1-carbonyl)-phenoxy]-tetrahydro-furan-3-yl}-amide;
Propane-2-sulfonic acid {4-[3-fluoro-4-(2-oxo-pyrrolidin-1-ylmethyl)-phenoxy]-tetrahydro-furan-3-yl}-amide;
Propane-2-sulfonic acid {4-[4-(1,1-dioxo-1lambda*6*-isothiazolidin-2-ylmethyl)-phenoxy]-tetrahydro-furan-3-yl}-amide;
Propane-2-sulfonic acid [4-(4-phenoxy-phenoxy)-tetrahydro-furan-3-yl]-amide;
N-{4-[4-(Propane-2-sulfonylamino)-tetrahydro-furan-3-yloxy]-phenyl}-benzamide;
Propane-2-sulfonic acid {4-[4-(2-oxo-pyrrolidin-1-yl)-phenoxy]-tetrahydro-furan-3-yl}-amide;
2-[2-Fluoro-4-(tetrahydro-furan-3-yloxy)-phenyl]-isothiazolidine 1,1-dioxide; compound with propane-2-sulfonic acid amide;
N-[4-(2'-Cyano-biphenyl-4-yloxy)-tetrahydro-furan-3-yl]-methanesulfonamide;
3-[4-(2'-Cyano-biphenyl-4-yloxy)-tetrahydro-furan-3-yl]-1,1-dimethyl-sulfonylurea;
Propane-2-sulfonic acid {4-[5-(2-cyano-phenyl)-pyridin-2-yloxy]-tetrahydro-furan-3-yl}-amide; and
Propane-2-sulfonic acid {4-[5-(2-cyano-phenyl)-pyrimidin-2-yloxy]-tetrahydro-furan-3-yl}-amide.

The compounds of Formula I and the pharmaceutically acceptable salts thereof are useful for the treatment of a variety of neurological and psychiatric disorders associated with glutamate dysfunction, including: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, social anxiety disorder, panic disorder, post-traumatic stress disorder and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, attention deficit disorder, and conduct disorder. Accordingly, in one embodiment, the invention provides a method for treating a condition in a mammal, such as a human, selected from the conditions above, comprising administering an effective amount of a compound of Formula I or a pharmaceutically acceptable salt thereof to the mammal. The mammal is preferably a mammal in need of such treatment or prevention.

The term "treating", as used herein, unless otherwise indicated, means reversing, alleviating, modulating, or inhibiting the progress of disorder or condition to which such term applies, or one or more symptoms of such disorder or condition. The term "treatment", as used herein, unless otherwise indicated, refers to the act of treating as "treating" is defined immediately above.

As an example, the invention provides a method for treating a condition selected from migraine, anxiety disorders, schizophrenia, and epilepsy. Exemplary anxiety disorders are generalized anxiety disorder, social anxiety disorder, panic disorder, post-traumatic stress disorder and obsessive-compulsive disorder. As another example, the invention provides a method for treating depression selected from Major Depression, Chronic Depression (Dysthymia), Seasonal Depression (Seasonal Affective Disorder), Psychotic Depression, and Postpartum Depression. As another example, the invention provides a method for treating a sleep disorder selected from insomnia and sleep deprivation.

In another embodiment, the invention comprises methods of treating a condition in a mammal, such as a human, by administering an effective amount of a compound of Formula I or a pharmaceutically acceptable salt thereof, wherein the condition is selected from the group consisting of atherosclerotic cardiovascular diseases, cerebrovascular diseases and peripheral arterial diseases, to the mammal. The mammal is preferably a mammal in need of such treatment or prevention. Other conditions that can be treated in accordance with the present invention include hypertension and angiogenesis.

In another embodiment, the present invention provides methods of treating neurological and psychiatric disorders associated with glutamate dysfunction, comprising administering to a mammal, preferably a mammal in need thereof, an amount of a compound of Formula I or a pharmaceutically acceptable salt thereof effective in treating such disorders.

The compound of Formula I or a pharmaceutically acceptable salt thereof is optionally used in combination with another active agent. Such an active agent may be, for example, an atypical antipsychotic or an AMPA potentiator. Accordingly, another embodiment of the invention provides methods of treating neurological and psychiatric disorders associated with glutamate dysfunction, comprising administering to a mammal an effective amount of a compound of Formula I or a pharmaceutically acceptable salt thereof and further comprising administering another active agent.

As used herein, the term "another active agent" refers to any therapeutic agent, other than the compound of Formula (I), or salt thereof, that is useful for the treatment of a subject disorder. Examples of additional therapeutic agents include antidepressants, antipsychotics, anti-pain, anti-Alzheimer's and anti-anxiety agents. Examples of particular classes of antidepressants that can be used in combination with the compounds of the invention include norepinephrine reuptake inhibitors, selective serotonin reuptake inhibitors (SSRIs), NK-1 receptor antagonists, monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, and atypical antidepressants. Suitable norepinephrine reuptake inhibitors include tertiary amine tricyclics and secondary amine tricyclics. Examples of suitable tertiary amine tricyclics and secondary amine tricyclics include amitriptyline, clomipramine, doxepin, imipramine, trimipramine, dothiepin, butriptyline, iprindole, lofepramine, nortriptyline, protriptyline, amoxapine, desipramine and maprotiline. Examples of suitable selective serotonin reuptake inhibitors include fluoxetine, fluvoxamine, paroxetine, and sertraline. Examples of monoamine oxidase inhibitors include isocarboxazid, phenelzine, and tranylcyclopramine. Examples of suitable reversible inhibitors of monoamine oxidase include moclobemide. Examples of suitable serotonin and noradrenaline reuptake inhibitors of use in the present invention include venlafaxine. Examples of suitable atypical anti-depressants include bupropion, lithium, nefazodone, trazodone and viloxazine. Examples of anti-Alheimer's agents include Dimebon, NMDA receptor antagonists such as memantine; and cholinesterase inhibitors such as donepezil and galantamine. Examples of suitable classes of anti-anxiety agents that can be used in combination with the compounds of the invention include benzodiazepines and serotonin 1A (5-HT1A) agonists or antagonists, especially 5-HT1A partial agonists, and corticotropin releasing factor (CRF) antagonists. Suitable benzodiazepines include alprazolam, chlordiazepoxide, clonazepam, chlorazepate, diazepam, halazepam, lorazepam, oxazepam, and prazepam. Suitable 5-HT1A receptor agonists or antagonists include buspirone, flesinoxan, gepirone and ipsapirone. Suitable atypical antipsychotics include paliperidone, bifeprunox, ziprasidone, risperidone, aripiprazole, olanzapine, and quetiapine. Suitable nicotine acetylcholine agonists include ispronicline, varenicline and MEM 3454. Anti-pain agents include pregabalin, gabapentin, clonidine, neostigmine, baclofen, midazolam, ketamine and ziconotide.

The invention is also directed to pharmaceutical compositions comprising a compound of Formula I or a pharmaceutically acceptable salt thereof, and a pharmaceutically acceptable carrier.

DETAILED DESCRIPTION OF THE INVENTION

The compounds of the Formula I may be prepared by the methods described below, together with synthetic methods known in the art of organic chemistry, or modifications and derivatisations that are familiar to those of ordinary skill in the art.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1999, which is hereby incorporated by reference.

As appreciated by the artisan, the use of Formula I is a convenience and the invention is understood to include each and every species falling thereunder as though individually set forth herein. Thus, the invention contemplates each species separately and any and all combinations of such species. More specifically, in the Scheme that follows, $R^1$ through $R^{11}$, m, n, p, q, s, t, w, A, B, X, Y, and Z are as defined above.

Scheme 1

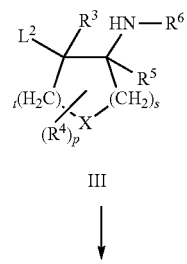

III

-continued

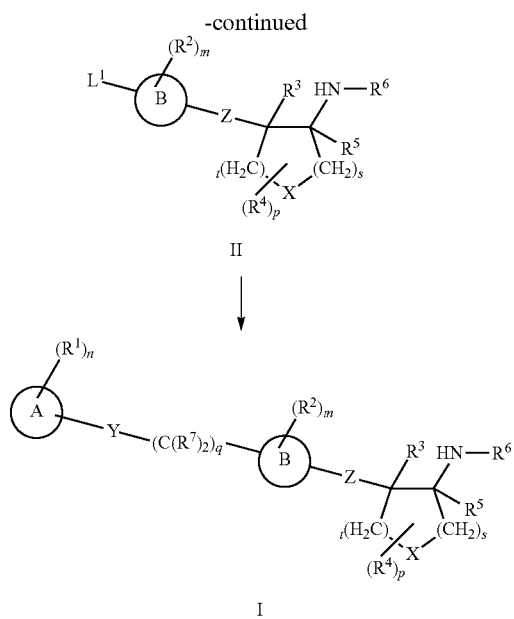

Scheme 1 refers to the preparation of compounds of the Formula I. Referring to Scheme 1, an aryl halide of Formula II, wherein $L^1$ is iodo, bromo or a triflate, may be coupled to a suitably substituted aryl boronic acid of structure $(R^1)_n$—ArB(OH)$_2$, wherein Ar represents a suitably substituted aryl or heteroaryl group and B is boron, under standard palladium catalyzed cross-coupling reaction conditions well known to one of ordinary skill in the art to provide the compound of Formula I. [Suzuki, A., Journal of Organometallic Chemistry, 576, 147-169 (1999), Miyaura and Suzuki, Chemical Reviews, 95, 2457-2483 (1995).] The compounds of Formula II may be prepared from the compounds of Formula III via displacement of $L^2$, wherein $L^2$ may be halo, —OSO$_2$CH$_3$ (—OMs), or —OSO$_2$CF$_3$ (—OTf), with a reactant

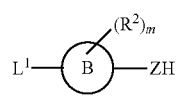

wherein Z is O or S. Typical conditions involve reaction in an organic solvent such as acetonitrile in the presence of a base such as cesium carbonate at elevated temperature such as 150° C. In the case where Z is S the product II or I may be further oxidized to afford >S=O or >SO$_2$ with a reagent such as a peroxide (such as mCPBA) in a solvent such as methylene chloride at room temperature.

Alternately, the compound of Formula III may be converted to a compound of Formula II, wherein $L^2$ is ZH and Z is O or S, by nucleophilic aromatic substitution (such as reaction with an aryl tin, such as SnAr) reaction with an appropriately substituted aryl reagent

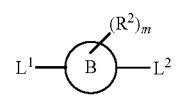

wherein $L^2$ is halo or —OSO$_2$CF$_3$ (—OTf) according to methods analogous to those described in Withbroe, G. J.; Singer, R. A.; Sieser, J. E. "Streamlined Synthesis of the Bippyphos Family of Ligands and Cross-Coupling Applications" *Org. Process Res. Dev.* 2008, 12, 480-489. Typical conditions involve reaction in an organic solvent such as ethanol in the presence of a base such as potassium hydroxide, a catalyst, such as a palladium (such as Pd2(dba)$_3$), and a ligand, such as 1-[2-[bis(tert-butyl)phosphino]phenyl]-3,5-diphenyl-1H-pyrazole (bippyphos), at elevated temperature such as 80° C.

Alternatively, a compound of Formula I may be prepared from a compound of Formula II, wherein $L^1$ is a silyl group (such as trimethylsilyl) by first converting the silyl group to a halide, such as by reaction with a halogenating reagent such as potassium bromide/N-chlorosuccinimide (NCS) in the presence of an acid (such as acetic acid) followed by arylation as described above. Suitable solvents for the halogenation include alcohols such as methanol or ethanol. The reaction may be conducted at a temperature of about 10° C. to about 60° C. for about 10 to about 120 minutes.

Alternatively, a compound of Formula I wherein q is zero and Y is O or NR$^7$ may be prepared by reaction of a compound of Formula II wherein $L^1$ is NH$_2$ or OH by reaction with an aryl halide in the presence of a catalyst.

Alternatively, when q is two or three, one skilled in the art will appreciate that numerous coupling reactions of two suitably functionalized alkyl groups may afford the compounds of Formula I. Such reactions are within the skill of the art.

The compound of Formula II may be prepared from a compound of Formula III by coupling with a suitably substituted Aryl Grignard in an ethereal solvent such as THF at about –30° C. to about room temperature. A catalyst, such as palladium or copper, may facilitate the reaction.

The compounds of Formula III are commercially available or may be made by methods well known to those skilled in the art or may be prepared by routine methods known in the art (such as those methods disclosed in standard reference books such as the COMPENDIUM OF ORGANIC SYNTHETIC METHODS, Vol. I-VI (published by Wiley-Interscience)).

The compounds of Formula I may be separated into the enantiomerically pure isomers according to methods well known to those skilled in the art and described in detail in the Example section herein.

The compounds of this invention may be used in the form of salts derived from inorganic or organic acids. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

Base salts can easily be prepared by treating the corresponding acidic compounds with an aqueous solution containing the desired pharmaceutically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of the reaction and maximum product yields.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts."

Typically, a compound of the invention is administered in an amount effective to treat or prevent a condition as described herein. The compounds of the invention are administered by any suitable route in the form of a pharmaceutical composition adapted to such a route, and in a dose effective for the treatment or prevention intended. Therapeutically effective doses of the compounds required to treat or prevent the progress of the medical condition are readily ascertained by one of ordinary skill in the art using preclinical and clinical approaches familiar to the medicinal arts.

The compounds of the invention may be administered orally. Oral administration may involve swallowing so that the compound enters the gastrointestinal tract, or buccal or sublingual administration may be employed by which the compound enters the blood stream directly from the mouth.

In another embodiment, the compounds of the invention may be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may be administered topically to the skin or mucosa, that is, dermally or transdermally. In another embodiment, the compounds of the invention may be administered intranasally or by inhalation. In another embodiment, the compounds of the invention may be administered rectally or vaginally. In another embodiment, the compounds of the invention may be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus, the dosage regimen may vary widely. Dosage levels of the order from about 0.01 mg to about 100 mg per kilogram of body weight per day are useful in the treatment or prevention of the above-indicated conditions. In one embodiment, the total daily dose of a compound of the invention (administered in single or divided doses) is typically from about 0.01 to about 100 mg/kg. In another embodiment, total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 or 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment or prevention of the conditions recited herein.

For the treatment or prevention of the conditions referred to above, a compound of the invention can be administered as the compound per se. Alternatively, pharmaceutically acceptable salts of the compounds are suitable for medical applications because of their greater aqueous solubility relative to the parent compounds.

In another embodiment, the present invention comprises pharmaceutical compositions. Such pharmaceutical compositions comprise a compound of the invention or a pharmaceutically acceptable salt thereof presented with a pharmaceutically-acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention and the pharmaceutically acceptable salts thereof may be administered by any suitable route, preferably in the form of a pharmaceutical composition adapted to such a route, and in a dose effective for the treatment or prevention intended. The active compounds, pharmaceutically acceptable salts thereof and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention or a pharmaceutically acceptable salt thereof. In another embodiment, the oral administration may be in a powder or granule form. In another embodiment, the oral dose form is sub-lingual, such as, for example, a lozenge. In such solid dosage forms, the compounds of formula I or a pharmaceutically acceptable salt thereof are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneally, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention and the pharmaceutically acceptable salts thereof are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Formulations suitable for topical administration to the eye include, for example, eye drops wherein the compound of this invention or a pharmaceutically acceptable salt thereof is dissolved or suspended in suitable carrier. A typical formulation suitable for ocular or aural administration may be in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention or the pharmaceutically acceptable salts thereof are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman, et al., Eds., Pharmaceutical Dosage Forms, Marcel Decker, New York, N.Y., 1980; and Kibbe, et al., Eds., Handbook of Pharmaceutical Excipients ($3^{rd}$ Ed.), American Pharmaceutical Association, Washington, 1999.

The compounds of the present invention and the pharmaceutically acceptable salts thereof can be used, alone or in combination with other therapeutic agents, in the treatment or prevention of various conditions or disease states. The compound(s) of the present invention, pharmaceutically acceptable salts thereof and other therapeutic agent(s) may be may be administered simultaneously (either in the same dosage form or in separate dosage forms) or sequentially in any order. An exemplary therapeutic agent may be, for example, a metabotropic glutamate receptor agonist.

The administration of two or more compounds "in combination" means that the two compounds are administered closely enough in time that the presence of one alters the biological effects of the other. The two or more compounds may be administered simultaneously, concurrently or sequentially in any order. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention further comprises kits that are suitable for use in performing the methods of treatment or prevention described above. In one embodiment, the kit contains a first dosage form comprising one or more of the compounds of the present invention or a pharmaceutically acceptable salt thereof and a container for the dosage, in quantities sufficient to carry out the methods of the present invention.

In another embodiment, the kit of the present invention comprises one or more compounds of the invention or a pharmaceutically acceptable salt thereof.

Three compounds of the invention were subjected to single crystal X-ray structure determination to elucidate their absolute stereochemistry. Crystallographic data is provided below.

Representative crystals were surveyed (see individual compounds below for characterization of data sets and diffractometers used). Friedel pairs were collected in order to facilitate the determination of the absolute configuration. Atomic scattering factors were taken from the International Tables for Crystallography, Vol. C, pp. 219, 500, Kluwer Academic Publishers, 1992. All crystallographic calculations were facilitated by the SHELXTL system, Version 5.1, Bruker AXS, 1997. All diffractometer data were collected at room temperature. Pertinent crystal, data collection, and refinement are summarized in Table I for each compound.

A trial structure was obtained by direct methods for each compound. These trial structures refined routinely. Hydrogen positions were calculated wherever possible. The methyl hydrogens were located by difference Fourier techniques and then idealized. Any hydrogens on nitrogen were located by difference Fourier techniques and allowed to refine. The hydrogen parameters were added to the structure factor calculations but were not refined. The shifts calculated in the final cycles of least squares refinement were all less than 0.1 of the corresponding standard deviations. Final R-indices are given for each structure. A final difference Fourier revealed no missing or misplaced electron density for any of these structures.

Absolute configurations were determined by the method of Flack, *Acta Crystallogr.*, 1983 A39, 876. Coordinates, anisotropic temperature factors, distances and angles are shown below (Tables 1-5) for each structure.

EXPERIMENTAL PROCEDURES

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

For syntheses referencing procedures in other Examples, Preparations or Methods, reaction conditions (length of reaction and temperature) may vary. In general, reactions were followed by thin layer chromatography or mass spectrometry, and subjected to work-up when appropriate. If non-product solids were present in the crude reaction mixture, filtration through Celite® may be employed. Purifications may vary between experiments: in general, solvents and the solvent ratios used for eluants/gradients were chosen to provide appropriate $R_f$s or retention times.

Preparation 1

Synthesis of cis-N-{4-[(6-bromopyridin-3-yl)oxy]tetrahydrofuran-3-yl}propane-2-sulfonamide Step 1. Synthesis of trans-4-[(6-bromopyridin-3-yl)oxy]tetrahydrofuran-3-ol The title compound of Step 1 was prepared according to the general procedure for the synthesis of trans-4-(4-bromophenoxy)tetrahydrofuran-3-ol in Example 2, except that 6-bromopyridin-3-ol was used in place of 4-bromophenol, and the crude product was purified by silica gel chromatography (Gradient: 20% to 70% ethyl acetate in heptane). Yield: 5.24 g, 20.2 mmol, 61%. $^1$H NMR (500 MHz, CDCl$_3$) δ 3.79 (dd, J=9.9, 1.9 Hz, 1H), 3.87 (dd, J=10.4, 1.8 Hz, 1H), 4.00 (dd, J=9.9, 4.3 Hz, 1H), 4.19 (dd, J=10.4, 4.7 Hz, 1H), 4.38 (br m, 1H), 4.59 (br s, 1H), 4.68 (br d, J=4.4 Hz, 1H), 7.14 (dd, J=8.7, 3.2 Hz, 1H), 7.32 (dd, J=8.7, 0.5 Hz, 1H), 8.01 (br d, J=3.1 Hz, 1H).

Step 2. Synthesis of trans-4-[(6-bromopyridin-3-yl)oxy]tetrahydrofuran-3-yl methanesulfonate The title compound of Step 2 was prepared according to the general procedure for the synthesis of trans-2-(4-bromophenoxy)cyclopentyl methanesulfonate in Example 5, except that trans-4-[(6-bromopyridin-3-yl)oxy]tetrahydrofuran-3-ol was used instead of trans-2-(4-bromophenoxy)cyclopentanol. The product was obtained as a solid. Yield: 5.95 g, 17.6 mmol, 87%. $^1$H NMR (400 MHz, CDCl$_3$) δ 3.07 (s, 3H), 3.94 (br dd, J=10.5, 1.8 Hz, 1H), 4.00 (m, 1H), 4.11 (dd, J=11.1, 4.1 Hz, 1H), 4.18 (dd, J=10.6, 4.5 Hz, 1H), 4.97 (br d, J=4.4 Hz, 1H), 5.13 (br d, J=3.8 Hz, 1H), 7.19 (dd, J=8.7, 3.2 Hz, 1H), 7.35 (dd, J=8.7, 0.5 Hz, 1H), 8.04 (dd, J=3.2, 0.5 Hz, 1H).

Step 3. Synthesis of cis-N-{4-[(6-bromopyridin-3-yl)oxy]tetrahydrofuran-3-yl}propane-2-sulfonamide Trans-4-[(6-bromopyridin-3-yl)oxy]tetrahydrofuran-3-yl methane sulfonate (591.7 mg, 1.75 mmol), propane-2-sulfonamide (647 mg, 5.25 mmol) and cesium carbonate (855 mg, 2.62 mmol) were combined in acetonitrile (8 mL) and subjected to microwave irradiation for 55 minutes at 150° C. The crude reaction mixture was combined with several similar reactions run under the same conditions (total starting material used: 1.527 g, 4.515 mmol) and shaken with saturated aqueous sodium bicarbonate solution (100 mL). The aqueous layer was extracted with ethyl acetate, and the combined organic layers were dried over sodium sulfate, filtered and concentrated in vacuo. The residue was purified via silica gel chromatography (Gradient: 5% to 40% ethyl acetate in heptane) to provide the title compound. Yield: 382 mg, 1.046 mmol, 23%. $^1$H NMR (400 MHz, CDCl$_3$) δ 1.34 (d, J=6.8 Hz, 3H), 1.36 (d, J=6.8 Hz, 3H), 3.17 (septet, J=6.8 Hz, 1H), 3.74 (dd, J=9, 9 Hz, 1H), 3.94 (dd, J=10.9, 1.5 Hz, 1H), 4.14 (dd, J=8, 8 Hz, 1H), 4.19 (dd, J=10.9, 4.3 Hz, 1H), 4.27 (m, 1H), 4.84 (m, 1H), 5.66 (d, J=9.9 Hz, 1H), 7.20 (dd, J=8.8, 3.2 Hz, 1H), 7.40 (d, J=8.8 Hz, 1H), 8.01 (d, J=3.2 Hz, 1H).

Preparation 2

Synthesis of methyl 3-cyano-4-(4,4,5,5-tetramethyl-1,3,2-dioxaborolan-2-yl)benzoate Step 1. Synthesis of methyl 3-cyano-4-{[(trifluoromethyl)sulfonyl]oxy}-benzoate A solution of methyl 3-cyano-4-hydroxybenzoate [see P. Madsen et al, *J. Medicinal Chemistry* 2002, 45, 5755-5775] (4.18 g, 23.6 mmol) in dichloromethane (81 mL) was treated with 4-(dimethylamino)pyridine (432 mg, 3.54 mmol) and cooled to 0° C. After addition of triethylamine (4.93 mL, 35.4 mmol), the solution was treated drop-wise with trifluoromethanesulfonic anhydride (5.96 mL, 35.4 mmol) and allowed to warm to room temperature. After 2 hours, the reaction was concentrated in vacuo, and repetitively treated with dichloromethane and concentrated until 17 grams of material remained. This was subjected to silica gel chromatography (Gradient: 0% to 10% ethyl acetate in heptane) to provide product as a colorless oil. Yield: 6.50 g, 21.0 mmol, 89%. $^1$H NMR (500 MHz, CDCl$_3$) δ 4.00 (s, 3H), 7.60 (d, J=8.8 Hz, 1H), 8.39 (dd, J=8.8, 2.1 Hz, 1H), 8.45 (d, J=2.2 Hz, 1H).

Step 2. Synthesis of Compound methyl 3-cyano-4-(4,4,5,5-tetramethyl-1,3,2-dioxaborolan-2-yl)benzoate 4,4,4',4',5,5,5',5'-Octamethyl-2,2'-bi-1,3,2-dioxaborolane (bis(pinacolato)diboron, 5.81 g, 22.9 mmol), methyl 3-cyano-4-{[(trifluoromethyl)sulfonyl]oxy}benzoate (5.90 g, 19.1 mmol), potassium acetate (99%, 9.46 g, 95.4 mmol) and 1,1'-[bis(diphenylphosphino)ferrocene]dichloropalladium (II) (1.40 g, 1.91 mmol) were combined in degassed dioxane (83 mL) in a thick-walled reaction flask. The reaction was sealed and heated at 100° C. for 18 hours, then treated with dichloromethane (100 mL), stirred well and filtered through Celite®. The filter cake was rinsed with dichloromethane (2×100 mL), and the combined filtrates were concentrated in vacuo and subjected to chromatography on silica gel (Gradient: 0% to 30% ethyl acetate in heptane). Fractions containing product were concentrated and subjected to recrystallization from 2-propanol to provide the title compound as a white solid. Yield: 3.395 g, 11.82 mmol, 62%. $^1$H NMR (400 MHz, CDCl$_3$) δ 1.41 (s, 12H), 3.97 (s, 3H), 7.98 (d, J=7.8 Hz, 1H), 8.20 (dd, J=7.8, 1.6 Hz, 1H), 8.35 (br d, J=1.6 Hz, 1H).

Preparation 3

Synthesis of N-[(1S,2R)-2-(4-bromo-3-fluorophenoxy)cyclopentyl]propane-2-sulfonamide

Step 1. Synthesis of trans-2-(4-bromo-3-fluorophenoxy)cyclopentanol

4-Bromo-3-fluorophenol (8.00 g, 41.9 mmol) and 6-oxabicyclo[3.1.0]hexane (8.25 mL, 95.2 mmol) were combined in butyronitrile (5.0 mL) and treated with sodium carbonate (4.04 g, 38.1 mmol). The reaction was subjected to microwave irradiation for 2 hours at 175° C., then filtered through Celite®. The filter cake was washed with ethyl acetate, then dichloromethane, and the combined filtrates were concentrated under reduced pressure to provide product as a dark brown oil. This material was used without additional purification. Yield: 11.59 g, >41.9 mmol, assumed quantitative. $^1$H NMR (400 MHz, CDCl$_3$) δ 1.61-1.89 (m, 5H), 2.02-2.24 (m, 2H), 4.30 (m, 1H), 4.46 (m, 1H), 6.63 (ddd, J=8.9, 2.8, 1.1 Hz, 1H), 6.73 (dd, J=10.5, 2.8 Hz, 1H), 7.40 (dd, J=8.9, 8.0 Hz, 1H).

Step 2. Synthesis of (1R,2R)-2-(4-bromo-3-fluorophenoxy)cyclopentyl acetate

The title compound in Step 2 was prepared according to the general procedure for the synthesis of (1R,2R)-2-(4-bromophenoxy)cyclohexyl acetate in Example 7, except that trans-2-(4-bromo-3-fluorophenoxy)cyclopentanol was used instead of trans-2-(4-bromophenoxy)cyclohexanol. The less polar material from the chromatographic purification on silica gel provided (1R,2R)-2-(4-bromo-3-fluorophenoxy)cyclopentyl acetate as an oil. Yield: 6.42 g, 20.2 mmol, 48% over 2 steps. $^1$H NMR (400 MHz, CDCl$_3$) δ 1.67-1.75 (m, 1H), 1.79-1.92 (m, 3H), 2.05-2.20 (m, 2H), 2.08 (s, 3H), 4.60 (m, 1H), 5.14 (m, 1H), 6.66 (ddd, J=8.9, 2.8, 1.1 Hz, 1H), 6.78 (dd, J=10.5, 2.8 Hz, 1H), 7.40 (dd, J=8.8, 8.1 Hz, 1H).

Step 3. Synthesis of (1R,2R)-2-(4-bromo-3-fluorophenoxy)-cyclopentanol

The title compound in Step 3 was prepared according to the general procedure for the synthesis of (1R,2R)-2-(4-bromophenoxy)cyclohexanol in Example 7, except that (1R,2R)-2-(4-bromo-3-fluorophenoxy)cyclopentyl acetate was used instead of (1R,2R)-2-(4-bromophenoxy)cyclohexyl acetate. The product was obtained as a yellow oil. Yield: 5.29 g, 19.2 mmol, 95%. $^1$H NMR (500 MHz, CDCl$_3$) δ 1.62-1.68 (m, 2H), 1.71-1.90 (m, 3H), 2.04-2.11 (m, 1H), 2.15-2.22 (m, 1H), 4.30 (m, 1H), 4.47 (m, 1H), 6.63 (ddd, J=8.9, 2.8, 1.1 Hz, 1H), 6.73 (dd, J=10.5, 2.8 Hz, 1H), 7.40 (dd, J=8.9, 8.1 Hz, 1H).

Step 4. Synthesis of (1R,2R)-2-(4-bromo-3-fluorophenoxy)cyclopentyl methanesulfonate The title compound in Step 4 was prepared according to the general procedure for the synthesis of trans-2-(4-bromophenoxy)cyclopentyl methanesulfonate in Example 5, except that (1R,2R)-2-(4-bromo-3-fluorophenoxy)cyclopentanol was used instead of trans-2-(4-bromophenoxy)cyclopentanol. The product was obtained as an oil, which was taken on to the following step without purification. MS (GCMS) m/z 352, 354 (M+1). $^1$H NMR (500 MHz, CDCl$_3$) δ 1.81-2.00 (m, 4H), 2.16-2.26 (m, 2H), 3.04 (s, 3H), 4.77 (m, 1H), 5.07 (m, 1H), 6.65 (ddd, J=8.9, 2.8, 1.1 Hz, 1H), 6.74 (dd, J=10.2, 2.8 Hz, 1H), 7.43 (dd, J=8.9, 8.0 Hz, 1H).

Step 5. Synthesis of (1R,2S)-2-azidocyclopentyl 4-bromo-3-fluorophenyl ether The title compound in Step 5 was prepared according to the general procedure for the synthesis of cis-2-azidocyclopentyl 4-bromophenyl ether in Example 5, except that (1R,2R)-2-(4-bromo-3-fluorophenoxy)cyclopentyl methanesulfonate was employed in place of trans-2-(4-bromophenoxy)cyclopentyl methanesulfonate. The product was isolated as a brown oil, which was used without purification in the following step. $^1$H NMR (400 MHz, CDCl$_3$) δ 1.66-1.75 (m, 1H), 1.88-2.08 (m, 5H), 3.74 (m, 1H), 4.65 (m, 1H), 6.66 (ddd, J=8.9, 2.8, 1.1 Hz, 1H), 6.75 (dd, J=10.4, 2.8 Hz, 1H), 7.42 (dd, J=8.8, 8.0 Hz, 1H).

Step 6: Synthesis of (1S,2R)-2-(4-bromo-3-fluorophenoxy)cyclopentanamine

The title compound in Step 6 was prepared according to the general procedure for the synthesis of cis-2-(4-bromophenoxy)cyclopentanamine in Example 5, except that (1R,2S)-2-azidocyclopentyl 4-bromo-3-fluorophenyl ether was used instead of cis-2-azidocyclopentyl 4-bromophenyl ether, and cis-2-(4-bromophenoxy)cyclopentanamine was taken on to the following step without purification. LCMS m/z 276.2 (M+1). $^1$H NMR (500 MHz, CDCl$_3$) δ 1.5 (v br s, 2H), 1.57-1.66 (m, 2H), 1.80-1.87 (m, 2H), 1.93-2.01 (m, 2H), 3.36 (m, 1H), 4.41 (m, 1H), 6.63 (ddd, J=8.9, 2.8, 1.1 Hz, 1H), 6.71 (dd, J=10.5, 2.8 Hz, 1H), 7.40 (dd, J=8.8, 8.0 Hz, 1H).

Step 7. Synthesis of N-[(1S,2R)-2-(4-bromo-3-fluorophenoxy)-cyclopentyl]propane-2-sulfonamide The title compound of Step 7 was prepared according to the general procedure for the synthesis of cis-N-[2-(4-bromophenoxy)cyclopentyl]propane-2-sulfonamide in Example 5, except that (1S,2R)-2-(4-bromo-3-fluorophenoxy)cyclopentanamine was used instead of cis-2-(4-bromophenoxy)cyclopentanamine, and the chromatographic purification was carried out with a gradient of 0% to 10% methanol in dichloromethane, to provide the title compound as an off-white solid. Yield: 4.15 g, 10.9 mmol, 54% from (1R,2R)-2-(4-bromo-3-fluorophenoxy)cyclopentyl acetate (5 steps). $^1$H NMR (500 MHz, CDCl$_3$) δ 1.36 (d, J=6.7 Hz, 3H), 1.39 (d, J=6.8 Hz, 3H), 1.62-1.69 (m, 1H), 1.77-1.90 (m, 3H), 1.92-2.00 (m, 1H), 2.10-2.15 (m, 1H), 3.14 (septet, J=6.8 Hz, 1H), 3.86 (m, 1H), 4.56-4.60 (m, 2H), 6.61 (ddd, J=8.9, 2.8, 1.1 Hz, 1H), 6.70 (dd, J=10.3, 2.8 Hz, 1H), 7.43 (dd, J=8.8, 8.1 Hz, 1H). The absolute configuration of N-[(1S,2R)-2-(4-bromo-3-fluorophenoxy)cyclopentyl]propane-2-sulfonamide was assigned by analogy to the stereochemistry of compounds in Example 7 and Preparation 6.

Preparation 4

Synthesis of (2-cyano-4-fluorophenyl)boronic acid

2-Bromo-5-fluorobenzonitrile (6.00 g, 30.0 mmol) and triisopropyl borate (8.28 mL, 36.0 mmol) were dissolved in a mixture of toluene (48 mL) and tetrahydrofuran (12 mL), and the solution was cooled in a dry ice/acetone bath. A solution of n-butyllithium in hexanes (2.5M, 14.4 mL, 36.0 mmol) was added drop-wise over 1 hour, and the reaction was then allowed to warm to room temperature with stirring over 18 hours. The mixture was cooled in an ice bath and treated with a 2N aqueous hydrochloric acid solution until the pH reached 1, then allowed to warm to room temperature, at which time the layers were separated, and the aqueous layer was extracted twice with ethyl acetate. The combined organic layers were washed twice with water, once with saturated aqueous sodium chloride solution, dried over magnesium sulfate, filtered and concentrated in vacuo. The resulting solid was recrystallized from ethyl acetate-heptane to provide (2-cyano-4-fluorophenyl)boronic acid as a white solid. Yield: 2.20 g, 13.3 mmol, 44%. $^1$H NMR (400 MHz, CD$_3$OD) δ 7.43 (ddd, J=8.6, 8.6, 2.5 Hz, 1H), 7.55 (dd, J=8.8, 2.5 Hz, 1H), 7.69 (br s, 1H).

Preparation 5

Synthesis of N-{2-[4-(4,4,5,5-tetramethyl-1,3,2-dioxaborolan-2-yl)phenyl]ethyl}methanesulfonamide Step 1. Synthesis of tert-butyl(methylsulfonyl){2-[4-(4,4,5,5-tetramethyl-1,3,2-dioxaborolan-2-yl)phenyl]ethyl}carbamate 4,4,5,5-Tetramethyl-1,3,2-dioxaborolane (4.29 mL, 29.6 mmol) was added slowly to a mixture of tert-butyl[2-(4-iodophenyl)ethyl](methylsulfonyl)carbamate (see J. P. Gardner and W. D. Miller, PCT Pat. Appl. Publ. WO 2001090055, 2001) (8.39 g, 19.7 mmol), triethylamine (9.64 mL, 69.1 mmol) and 1,1'-[bis(diphenylphosphino)ferrocene]dichloropalladium(II) (217 mg, 0.296 mmol) in acetonitrile (50 mL), and the reaction mixture was heated at 75° C. for 4 hours. After removal of solvent, the residue was mixed with water (240 mL) and extracted with methyl tert-butyl ether. The combined organic layers were washed with saturated aqueous sodium chloride solution and with water, then dried over magnesium sulfate, filtered and concentrated in vacuo to provide synthesis of tert-butyl(methylsulfonyl){2-[4-(4,4,5,5-tetramethyl-1,3,2-dioxaborolan-2-yl)phenyl]ethyl}carbamate, which was used without additional purification. Yield: assumed quantitative. LCMS m/z 326.1 (M+1). $^1$H NMR (400 MHz, CDCl$_3$) δ 1.35 (s, 12H), 2.84 (s, 3H), 2.90 (t, J=6.8 Hz, 2H), 3.42 (dt, J=6.6, 6.6 Hz, 2H), 4.18 (br t, J=6 Hz, 1H), 7.23 (d, J=8.1 Hz, 2H), 7.78 (d, J=8.1 Hz, 2H).

Step 2. Synthesis of N-{2-[4-(4,4,5,5-tetramethyl-1,3,2-dioxaborolan-2-yl)phenyl]ethyl}methanesulfonamide Trifluoroacetic acid (10 mL) was added to a 0° C. solution of tert-butyl (methylsulfonyl){2-[4-(4,4,5,5-tetramethyl-1,3,2-dioxaborolan-2-yl)phenyl]ethyl}carbamate (from the previous step, assumed 19.7 mmol) in dichloromethane (100 mL). The reaction mixture was allowed to warm to room temperature and stir for 18 hours. It was then cooled to 0° C. and brought to pH 10.5 with a 4N aqueous sodium hydroxide solution. The organic layer was washed with saturated aqueous sodium chloride solution, dried over magnesium sulfate, filtered and concentrated in vacuo. The residue was purified via silica gel chromatography (Gradient: 0% to 5% methanol in dichloromethane) to provide the title compound as an off-white solid. Yield: 2.5 g, 7.7 mmol, 39% over two steps. LCMS m/z 326.1 (M+1). $^1$H NMR (400 MHz, CDCl$_3$) δ 1.35 (s, 12H), 2.84 (s, 3H), 2.90 (t, J=6.8 Hz, 2H), 3.42 (dt, J=6.6, 6.6 Hz, 2H), 4.18 (br t, J=6 Hz, 1H), 7.23 (d, J=8.1 Hz, 2H), 7.78 (d, J=8.1 Hz, 2H).

Preparation 6

Synthesis of N-[(1S,2R)-2-(4-bromo-3-fluorophenoxy)cyclohexyl]propane-2-sulfonamide The title compound was prepared according to the general procedure for the synthesis of cis-N-[2-(4-bromophenoxy)cyclopentyl]propane-2-sulfonamide in Example 5, except that (1S,2R)-2-(4-bromo-3-fluorophenoxy)cyclohexanamine was used in place of cis-2-(4-bromophenoxy)cyclopentanamine, and the chromatographic purification employed 0% to 1% methanol in dichloromethane as gradient. (1S,2R)-2-(4-Bromo-3-fluorophenoxy)cyclohexanamine was synthesized according to the general procedures described for synthesis of (1S,2R)-2-(4-bromophenoxy)cyclohexanamine in Example 7, except for the use of 4-bromo-3-fluorophenol in place of 4-bromophenol. The title compound was obtained as a white solid. $^1$H NMR (400 MHz, CDCl$_3$) δ 1.33-1.53 (m, 4H), 1.35-1.38 (m, 6H), 1.78-1.89 (m, 3H), 2.04-2.10 (m, 1H), 3.12 (septet, J=6.8 Hz, 1H), 3.54 (m, 1H), 4.44 (d, J=9.6 Hz, 1H), 4.55 (m, 1H), 6.67 (br dd, J=8.9, 2.8 Hz, 1H), 6.75 (dd, J=10.2, 2.7 Hz, 1H), 7.43 (dd, J=8.5, 8.5 Hz, 1H). The absolute configuration of the title compound was established via X-ray crystallography.

Preparation 7

Synthesis of N-{(1S,2R)-2-[(6-bromopyridin-3-yl)oxy]cyclohexyl}propane-2-sulfonamide Step 1. Synthesis of trans-2-[(6-bromopyridin-3-yl)oxy]cyclohexanol The title compound of Step 1 was prepared according to the general procedure for the synthesis of trans-2-(4-bromo-3-fluorophenoxy)cyclopentanol in Preparation 3, except that 6-bromopyridin-3-ol was used instead of 4-bromo-3-fluorophenol, and 7-oxabicyclo[4.1.0]heptane in place of 6-oxabicyclo[3.1.0]hexane. The crude product (preparation run in four batches) was recrystallized from heptane to provide trans-2-[(6-bromopyridin-3-yl)oxy]cyclohexanol as an off-white solid. Yield: 11.09 g, 40.75 mmol, 46%. $^1$H NMR (500 MHz, CDCl$_3$) δ 1.27-1.46 (m, 4H), 1.76-1.80 (m, 2H), 2.09-

2.13 (m, 2H), 2.41 (d, J=2.6 Hz, 1H), 3.74 (m, 1H), 4.00 (m, 1H), 7.17 (dd, J=8.7, 3.1 Hz, 1H), 7.37 (d, J=8.5 Hz, 1H), 8.10 (d, J=3.0 Hz, 1H).

Step 2. Synthesis of cis-2-[(6-bromopyridin-3-yl)oxy]cyclohexanamine

Cis-5-[(2-azidocyclohexyl)oxy]-2-bromopyridine, prepared from trans-2-[(6-bromopyridin-3-yl)oxy]cyclohexanol by the general procedures described in Example 5 for the conversion of trans-2-(4-bromophenoxy)cyclopentanol to cis-2-azidocyclopentyl 4-bromophenyl ether) (13.5 g, 45.4 mmol) was dissolved in tetrahydrofuran (292 mL) and water (23 mL), and the solution was treated with triphenylphosphine (23.8 g, 90.7 mmol). The reaction was stirred for 18 hours at room temperature, then partitioned between ethyl acetate (500 mL) and water (200 mL). The aqueous layer was extracted with ethyl acetate, and the combined organic layers were washed with water (2×200 mL) and saturated aqueous sodium chloride solution (200 mL). The organic layer was then extracted with aqueous 1N hydrochloric acid (4×150 mL), and the combined aqueous layers were washed with ethyl acetate (150 mL). The aqueous layer was then cooled in an ice bath and slowly treated with an aqueous 2N solution of sodium hydroxide, until the mixture was a cloudy white; it was then extracted with ethyl acetate (3×150 mL), and the combined organic layers were washed with saturated aqueous sodium chloride solution (150 mL), dried over sodium sulfate, filtered and concentrated in vacuo. Cis-2-[(6-bromopyridin-3-yl)oxy]cyclohexanamine was obtained as a yellow oil. Yield: 8.00 g, 29.5 mmol, 65%. $^1$H NMR (500 MHz, CDCl$_3$) δ 1.34 (d, J=6.8 Hz, 3H), 1.35 (d, J=6.7 Hz, 3H), 1.35-1.52 (m, 4H), 1.79-1.85 (m, 3H), 2.02 (m, 1H), 3.11 (septet, J=6.8 Hz, 1H), 3.53 (m, 1H), 4.59 (br s, 1H), 4.68 (m, 1H), 7.19 (dd, J=8.7, 3.1 Hz, 1H), 7.38 (d, J=8.7 Hz, 1H), 8.07 (d, J=3.2 Hz, 1H).

Step 3. Synthesis of cis-N-{2-[(6-bromopyridin-3-yl)oxy]cyclohexyl}-propane-2-sulfonamide The title compound of Step 3 was prepared according to the general procedure for the synthesis of cis-N-[2-(4-bromophenoxy)cyclopentyl]propane-2-sulfonamide cis-N-[2-(4-bromophenoxy)cyclopentyl]propane-2-sulfonamide in Example 5, except that cis-2-[(6-bromopyridin-3-yl)oxy]cyclohexanamine was used in place of cis-2-(4-bromophenoxy)cyclopentanamine, and the 4-(dimethylamino)pyridine was omitted. The silica gel chromatography in this case was carried out with an eluant of 2% methanol in dichloromethane, to provide cis-N-{2-[(6-bromopyriclin-3-yl)oxy]cyclohexyl}propane-2-sulfonamide as a beige foam. Yield: 7.96 g, 21.1 mmol, 72%. $^1$H NMR (500 MHz, CDCl$_3$) δ 1.34 (d, J=6.8 Hz, 3H), 1.35 (d, J=6.7 Hz, 3H), 1.35-1.52 (m, 4H), 1.79-1.85 (m, 3H), 2.02 (m, 1H), 3.11 (septet, J=6.8 Hz, 1H), 3.53 (m, 1H), 4.59 (br s, 1H), 4.68 (m, 1H), 7.19 (dd, J=8.7, 3.1 Hz, 1H), 7.38 (d, J=8.7 Hz, 1H), 8.07 (d, J=3.2 Hz, 1H).

Step 4. Isolation of N-{(1S,2R)-2-[(6-bromopyridin-3-yl)oxy]cyclohexyl}propane-2-sulfonamide Separation of the enantiomers comprising cis-N-{2-[(6-bromopyridin-3-yl)oxy]cyclohexyl}propane-2-sulfonamide (7.96 g, 21.1 mmol) was carried out by chiral chromatography. Column: Chiralpak® AD-H, 2.1×25 cm, 5 μm; Mobile phase: 70:30 carbon dioxide: methanol; Flow rate: 65 g/min. The first-eluting compound was enantiomer [N-{(1R,2S)-2-[(6-bromopyridin-3-yl)oxy]cyclohexyl}propane-2-sulfonamide] and the second-eluting peak provided desired product N-{(1S,2R)-2-[(6-bromopyridin-3-yl)oxy]cyclohexyl}propane-2-sulfonamide upon removal of solvent in vacuo. Yield: 3.13 g, 8.30 mmol, 39%. The absolute stereochemistry of these enantiomers was assigned by analogy to Example 5.

Preparation 8

Synthesis of cis-N-[4-(4-bromophenoxy)tetrahydrofuran-3-yl]propane-2-sulfonamide The title compound was prepared according to the general procedure for the synthesis of cis-N-{4-[(6-bromopyridin-3-yl)oxy]tetrahydrofuran-3-yl}propane-2-sulfonamide in Preparation 1, except that trans-4-(4-bromophenoxy)tetrahydrofuran-3-yl methanesulfonate was used in place of trans-4-[(6-bromopyridin-3-yl)oxy]tetrahydrofuran-3-yl methanesulfonate, and the chromatographic purification was carried out with a gradient of 15% to 35% acetone in heptane. Yield: 238 mg, 0.65 mmol, 31%. $^1$H NMR (400 MHz, CDCl$_3$) δ 1.30 (d, J=6.8 Hz, 3H), 1.33 (d, J=6.8 Hz, 3H), 3.11 (septet, J=6.8 Hz, 1H), 3.66 (dd, J=9.1, 8.4 Hz, 1H), 3.89 (dd, J=10.7, 1.7 Hz, 1H), 4.07-4.13 (m, 2H), 4.19 (m, 1H), 4.71 (m, 1H), 5.12 (d, J=9.6 Hz, 1H), 6.75 (d, J=9.0 Hz, 2H), 7.36 (d, J=9.0 Hz, 2H).

Example 1

Synthesis of N-{1-[4-trans-({4-[(isopropylsulfonyl)amino]tetrahydrofuran-3-yl}oxy)phenyl]pyrrolidin-3-yl}acetamide

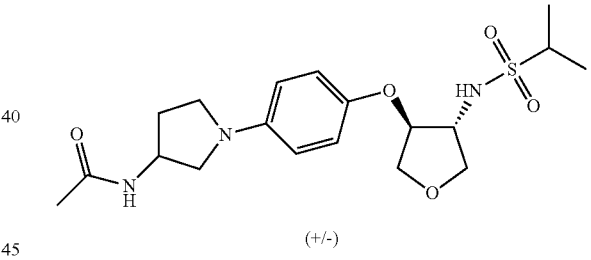

(+/-)

Step 1. Synthesis of trans-N-(4-hydroxytetrahydrofuran-3-yl)propane-2-sulfonamide 3,6-Dioxabicyclo[3.1.0]hexane (1.90 g, 22.1 mmol), propane-2-sulfonamide (prepared according to the method of D. C. Johnson, II and T. S. Widlanski, *Tetrahedron Letters* 2004, 45, 8483-8487) (3.13 g, 25.4 mmol), potassium carbonate (584 mg, 4.23 mmol) and benzyltriethylammonium chloride (963 mg, 4.23 mmol) were suspended in dioxane (10 mL) and heated at reflux for 120 hours. The reaction was cooled to room temperature, filtered, concentrated in vacuo and purified by silica gel chromatography (Gradient: 40% to 80% ethyl acetate in heptane), to afford trans-N-(4-hydroxytetrahydrofuran-3-yl)propane-2-sulfonamide as a solid. Yield: 3.76 g, 18.0 mmol, 81%. $^1$H NMR (400 MHz, CDCl$_3$) δ 1.38 (d, J=6.7 Hz, 3H), 1.40 (d, J=6.7 Hz, 3H) 2.91 (d, J=3.6 Hz, 1H), 3.22 (septet, J=6.8 Hz, 1H), 3.67-3.71 (m, 2H), 3.82 (m, 1H), 4.08-4.12 (m, 2H), 4.40 (m, 1H), 4.77 (d, J=8.4 Hz, 1H), $^{13}$C NMR (100 MHz, CDCl$_3$) δ 16.44, 16.69, 54.18, 62.06, 71.47, 73.50, 77.64.

Step 2. Synthesis of trans-4-[(isopropylsulfonyl)amino]tetrahydrofuran-3-yl methanesulfonate Triethylamine (1.99 mL, 14.3 mmol) was added to a cooled (0° C.) solution of trans-N-(4-hydroxytetrahydrofuran-3-yl)propane-2-sulfonamide (1.99 g, 9.52 mmol) in dichloromethane (20 mL). Methanesulfonyl chloride (0.885 mL, 11.4 mmol) was then added and the reaction was stirred at 0° C. for 50 minutes. Saturated aqueous sodium bicarbonate solution (10 mL) was added, and the aqueous layer was extracted with methylene chloride. The combined organic layers were dried over sodium sulfate, filtered, concentrated in vacuo and purified by silica gel chromatography (Gradient: 10% to 50% ethyl acetate in heptane) to provide trans-4-[(isopropylsulfonyl)amino]tetrahydrofuran-3-yl methanesulfonate. Yield: 2.27 g, 7.90 mmol, 83%. $^1$H NMR (400 MHz, CDCl$_3$) δ 1.40 (d, J=6.8 Hz, 3H), 1.41 (d, J=6.8 Hz, 3H), 3.14 (s, 3H), 3.25 (septet, J=6.8 Hz, 1H), 3.77 (dd, J=9.5, 2.4 Hz, 1H), 3.96 (dd, J=11.3, 2.2 Hz, 1H), 4.08-4.16 (m, 2H), 4.21 (dd, J=11.3, 5.1 Hz, 1H), 4.77 (d, J=8.0 Hz, 1H), 5.15 (m, 1H). $^{13}$C NMR (100 MHz, CDCl$_3$) δ 16.48, 16.54, 38.28, 54.28, 59.49, 71.83, 71.87, 83.97.

Step 3. Synthesis of trans-N-[4-(4-bromophenoxy)tetrahydrofuran-3-yl]propane-2-sulfonamide In a microwave vial, a solution of trans-4-[(isopropylsulfonyl)amino]tetrahydrofuran-3-yl methanesulfonate (546 mg, 1.90 mmol) in acetonitrile (8 mL) was combined with 4-bromophenol (97%, 407 mg, 2.28 mmol) and cesium carbonate (929 mg, 2.85 mmol). The reaction was irradiated in a microwave reactor at 160° C. for 2 hours, then cooled to room temperature and treated with saturated aqueous sodium bicarbonate solution (10 mL). The reaction was extracted with ethyl acetate and the combined organic layers were dried over sodium sulfate, filtered, and concentrated in vacuo. The residue was purified by silica gel chromatography (Gradient: 20% to 50% ethyl acetate in heptane), to afford trans-N-[4-(4-bromophenoxy)tetrahydrofuran-3-yl]propane-2-sulfonamide. Yield: 626 mg, 1.72 mmol, 91%. LCMS m/z 361.9 (M−1). $^1$H NMR (400 MHz, CDCl$_3$) δ 1.38 (d, J=6.9 Hz, 3H), 1.40 (d, J=6.8 Hz, 3H), 3.19 (septet, J=6.8 Hz, 1H), 3.82 (br d, J=8.0, 1H), 3.91 (dd, J=10.6, 1.7 Hz, 1H), 4.02-4.08 (m, 2H), 4.24 (dd, J=10.5, 4.7 Hz, 1H), 4.85 (br d, J=4.7 Hz, 1H), 4.95 (br d, J=8.3 Hz, 1H), 6.88 (d, J=9.0 Hz, 2H), 7.40 (d, J=9.0 Hz, 2H). $^{13}$C NMR (100 MHz, CDCl$_3$) δ 16.45, 16.71, 54.14, 58.70, 71.45, 71.81, 82.07, 113.97, 117.20, 132.52, 155.75.

Step 4. Synthesis of N-{1-[4-trans-({4-[(isopropylsulfonyl)amino]-tetrahydrofuran-3-yl}oxy)phenyl]pyrrolidin-3-yl}acetamide To 2-methylbutan-2-ol (2.0 mL) was added 2'-(dicyclohexylphosphino)-N,N-dimethylbiphenyl-2-amine (3.2 mg, 0.008 mmol) and tris(dibenzylideneacetone)dipalladium(0) (2.7 mg, 0.003 mmol). The purple reaction mixture was then degassed for 20 minutes and trans-N-[4-(4-bromophenoxy)tetrahydrofuran-3-yl]propane-2-sulfonamide (95 mg, 0.26 mmol) and N-pyrrolidin-3-ylacetamide (67 mg, 0.52 mmol) were added. Next, potassium hydroxide (32 mg, 0.57 mmol) was added and the reaction was degassed for an additional 20 minutes. The brown reaction mixture was heated to reflux under nitrogen and turned yellow. The reaction was monitored by GC-MS and when the reaction was complete, saturated aqueous sodium bicarbonate solution (5 mL) was added. The aqueous layer was extracted with ethyl acetate and the combined organics were dried over sodium sulfate, filtered, concentrated in vacuo, and purified by silica gel chromatography (Gradient: 50% to 70% ethyl acetate in heptane), to afford the diastereomeric mixture N-{1-[4-trans-({4-[(isopropylsulfonyl)amino]tetrahydrofuran-3-yl}oxy)phenyl]pyrrolidin-3-yl}acetamide as a gum Yield: 97.5 mg, 0.236 mmol, 91%. $^1$H NMR (400 MHz, CDCl$_3$) δ 1.31 (d, J=6.8 Hz, 3H), 1.32 (d, J=6.8 Hz, 3H), 1.93 (s, 3H), 2.22 (m, 1H), 2.64 (br s, 1H), 3.07-3.13 (m, 2H), 3.19 (m, 1H), 3.34-3.43 (m, 2H), 3.74 (dd, J=9.0, 1.8 Hz, 1H), 3.85 (dd, J=10.3, 1.7 Hz, 1H), 4.00-4.13 (m, 3H), 4.53 (m, 1H), 4.69 (br s, 1H), 5.67 (d, J=8.0 Hz, 1H), 6.46 (d, J=8.8 Hz, 2H), 6.46 (1H, pattern obscured by aromatic signal), 6.84 (d, J=9.0 Hz, 2H). $^{13}$C NMR (100 MHz, CDCl$_3$) δ 16.37, 16.46, 22.98, 31.44, 46.32, 49.31, 53.61, 53.88, 58.67, 71.45, 71.87, 82.80, 112.72, 117.00, 143.13, 147.98, 170.23.

Example 2

N-[(3S,4S)-4-(biphenyl-4-yloxy)tetrahydrofuran-3-yl]propane-2-sulfonamide

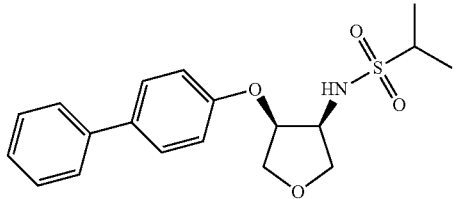 [SMILES: CC(C)S(=O)(=O)N[C@H]1COC[C@H]1Oc1ccc(-c2ccccc2)cc1]

Step 1. Synthesis of trans-4-(4-bromophenoxy)tetrahydrofuran-3-ol 3,6-Dioxabicyclo[3.1.0]hexane (100 g, 1.16 mol), 4-bromophenol (241.1 g, 1.39 mol), cesium carbonate (492 g, 1.51 mol) and benzyltriethylammonium chloride (52.9 g, 0.23 mol) were suspended in dioxane (1 L) and heated at reflux for 18 hours. The reaction was cooled to room temperature and diluted with ethyl acetate, then washed with saturated aqueous sodium carbonate solution. The aqueous layer was extracted with ethyl acetate, and the combined organic portions were dried over sodium sulfate, filtered and concentrated in vacuo, to provide crude product, which solidified on standing. This was used without purification in the next step. Yield: 354 g, >100%, assumed quantitative. Material from a smaller-scale experiment carried out in similar fashion was purified by silica gel chromatography for characterization (Gradient: 10% to 35% ethyl acetate in heptane), to afford trans-4-(4-bromophenoxy)tetrahydrofuran-3-ol as a solid. $^1$H NMR (400 MHz, CDCl$_3$) δ 2.09 (br d, J=4.5 Hz, 1H), 3.83 (m, 1H), 3.91 (dd, J=10.3, 2.1 Hz, 1H), 4.05 (dd, J=10.1, 4.0 Hz, 1H), 4.26 (dd, J=10.4, 4.9 Hz, 1H), 4.41 (br s, 1H), 4.67 (m, 1H), 6.81 (d, J=9.0 Hz, 2H), 7.40 (d, J=9.1 Hz, 2H).

Step 2. Synthesis of trans-4-(4-bromophenoxy)tetrahydrofuran-3-yl methanesulfonate Triethylamine (181.9 mL, 1.31 mol) was added to a solution of trans-4-(4-bromophenoxy)tetrahydrofuran-3-ol from the previous step (354 g, assumed 300.6 g, 1.16 mol) in methylene chloride (2 L), and the reaction was cooled to 0° C. in an ice bath. Methanesulfonyl chloride (101.3 mL, 1.31 mol) was then added drop-wise, while keeping the reaction temperature below 5° C., and the reaction was stirred at room temperature for 18 hours. Water (1.5 L) was added, and the aqueous layer was extracted with methylene chloride. The organics were combined and dried over sodium sulfate, filtered and concentrated in vacuo to afford product as a brown oil. Yield: 399.6 g, 1.18 mol, quantitative. Material from a smaller-scale experiment carried out in similar fashion was triturated with ethanol for characterization. $^1$H NMR (400 MHz, CDCl$_3$) δ 3.10 (s, 3H), 4.00 (br dd, J=10.4, 1.9 Hz, 1H), 4.07 (m, 1H), 4.16 (dd, J=11.1, 3.9 Hz, 1H), 4.23 (dd, J=10.5, 4.6 Hz, 1H), 4.98 (br d, J=4.6 Hz, 1H), 5.20 (m, 1H), 6.85 (d, J=9.1 Hz, 2H), 7.42 (d, J=9.0 Hz, 2H).

Step 3. Synthesis of
cis-3-azido-4-(4-bromophenoxy)tetrahydrofuran

To a solution of trans-4-(4-bromophenoxy)tetrahydrofuran-3-yl methanesulfonate (133.2 g, 0.395 mol) in dimethylformamide (3 L) was added sodium azide (192.6 g, 2.96 mol) and the reaction was heated at 110° C. for 66 hours. The reaction was cooled to room temperature and water (12 L) was added. This reaction was carried out a total of three times on the same scale, and the combined batches were extracted with tert-butyl methyl ether. The organic layers were then dried over sodium sulfate and concentrated in vacuo to afford product as a red-brown oil, contaminated with 18% dimethylformamide. Corrected yield: 286.7 g, 1.01 mol, 85%. $^1$H NMR (400 MHz, CDCl$_3$) δ 3.93-3.97 (m, 2H), 4.00 (m, 1H), 4.09 (dd, J=8.7, 5.8 Hz, 1H), 4.17 (dd, J=10.0, 5.6 Hz, 1H), 4.90 (ddd, J=5.4, 5.4, 4.4 Hz, 1H), 6.83 (d, J=9.1 Hz, 2H), 7.41 (d, J=9.0 Hz, 2H).

Step 4. Synthesis of
cis-4-(4-bromophenoxy)tetrahydrofuran-3-amine

A solution of cis-3-azido-4-(4-bromophenoxy)tetrahydrofuran (286.7 g, 1.01 mol) in tetrahydrofuran (1.25 L) was cooled to 0° C. and treated with triphenylphosphine (278 g, 1.06 mol). The reaction was allowed to warm to room temperature and stirred for 18 hours. Water (53 mL) was added and the reaction was stirred at room temperature for 66 hours. Solvent was removed under reduced pressure and the residue was mixed with diethyl ether. The supernatant was decanted and concentrated in vacuo, providing a residue, which was filtered through a short plug of silica gel (Gradient: 0% to 5% methanol in methylene chloride) to afford cis-4-(4-bromophenoxy)tetrahydrofuran-3-amine (155 g) and 366 grams of impure product. An acid/base extraction was carried out on the impure material, providing additional product (48.5 g). Total yield: 203.5 g, 0.788 mol, 68% over four steps. $^1$H NMR (300 MHz, CDCl$_3$) δ 3.6 (m, 1H), 3.7 (m, 1H), 3.9 (m, 1H), 4.0 (m, 1H), 4.1 (m, 1H), 4.6 (m, 1H), 6.8 (m, 2H), 7.3 (m, 2H).

Step 5. Synthesis of
(3S,4S)-4-(4-bromophenoxy)tetrahydrofuran-3-amine

A mixture of cis-4-(4-bromophenoxy)tetrahydrofuran-3-amine (191 g, 0.74 mol) and (1S)-(+)-10-camphorsulfonic acid (154.2 g, 0.66 mol) was dissolved in 2-propanol (2.4 L) and water (100 mL) at reflux. The clear solution was allowed to cool to room temperature over 18 hours, and the resulting crystals were isolated, washed and dried to afford the (+)-camphorsulfonic acid salt of (3S,4S)-4-(4-bromophenoxy) tetrahydrofuran-3-amine (139.2 g, 0.284 mol) with an e.e. (enantiomeric excess) of 85%. Recrystallization from 2-propanol (1.2 L) and water (70 mL) afforded the (+)-camphorsulfonic acid salt of (3S,4S)-4-(4-bromophenoxy)tetrahydrofuran-3-amine, with an e.e. of 99%. Yield: 113.2 g, 0.23 mol, 31%. $^1$H NMR (300 MHz, DMSO-d$_6$) δ 0.74 (s, 3H), 1.05 (s, 3H), 1.23 (d, half of AB quartet J=10 Hz, 1H), 1.29 (d, half of AB quartet, J=10 Hz, 1H), 1.76-1.94 (m, 2H), 2.19-2.28 (m, estimated 2H), 2.35 (d, J=14.7 Hz, 1H), 2.66-2.73 (m, estimated 1H), 2.85 (d, J=14.7 Hz, 1H), 3.78-3.84 (m, 2H), 3.96-4.10 (m, 3H), 5.04 (m, 1H), 6.99 (d, J=8.8 Hz, 2H), 7.52 (d, J=9.0 Hz, 2H), 8.23 (br s, 3H). Additional (3S,4S)-4-(4-bromophenoxy)tetrahydrofuran-3-amine(+)-camphorsulfonic acid salt (13.6 g, 27.7 mmol) from another experiment was added and the combined batch (126.8 g, 0.258 mol) was washed with 2N aqueous sodium hydroxide solution and extracted three times with methylene chloride. The organic layers were combined and concentrated in vacuo, affording (3S,4S)-4-(4-bromophenoxy)tetrahydrofuran-3-amine as a white solid with an e.e. of 99%. Yield: 65.6 g, 0.254 mmol, 98% for neutralization.

The combined mother liquors from above, enriched in (3R,4R)-4-(4-bromophenoxy)tetrahydrofuran-3-amine, were washed with 2N sodium hydroxide and extracted with methylene chloride. The combined organic layers were dried over sodium sulfate and concentrated in vacuo to give a residue (156.3 g, 0.606 mol of product and its enantiomer). This material was combined with (1R)-(–)-10-camphorsulfonic acid (126.2 g, 0.54 mol) and dissolved in 2-propanol (1.65 L) and water (100 mL) at reflux. The clear solution was allowed to cool to room temperature over 18 hours and the resulting crystals were isolated, washed and dried. This afforded the (–)-camphorsulfonic acid salt of (3R,4R)-4-(4-bromophenoxy)tetrahydrofuran-3-amine (152.6 g, 0.311 mol), with an e.e. of 90%. Recrystallization as above afforded the (–)-camphorsulfonic acid salt of (3R,4R)-4-(4-bromophenoxy) tetrahydrofuran-3-amine as a white solid, with an e.e. of 99%. Yield: 132.0 g, 0.27 mol, 36%.

The mother liquor was concentrated in vacuo, washed with 2N sodium hydroxide and extracted with methylene chloride. The combined organic layers were dried over sodium sulfate and concentrated under reduced pressure to obtain a mixture of (3S,4S)-4-(4-bromophenoxy)tetrahydrofuran-3-amine and its enantiomer (67.7 g, 0.26 mol). Together with (1S)-(+)-10-camphorsulfonic acid (54.6 g, 0.24 mol), this material was dissolved in 2-propanol (425 mL) and water (17.5 mL) at reflux. The clear solution was allowed to reach room temperature over 18 hours and the resulting crystals were isolated, washed and dried. This afforded additional (3S,4S)-4-(4-bromophenoxy)tetrahydrofuran-3-amine(+)-camphorsulfonic acid salt (48.0 g, 97.9 mmol), with an e.e. of 89-93% Recrystallization afforded (3S,4S)-4-(4-bromophenoxy)tetrahydrofuran-3-amine(+)-camphorsulfonic acid salt (40.0 g, 81.6 mmol, additional 11%) with an e.e. of 99+%.

Step 6. Synthesis of N-[(3S,4S)-4-(4-bromophenoxy) tetrahydrofuran-3-yl]propane-2-sulfonamide To a solution of (3S,4S)-4-(4-bromophenoxy)tetrahydrofuran-3-amine (65.6 g, 0.254 mol) in methylene chloride (500 mL) was added 1,8-diazabicyclo[5.4.0]undec-7-ene (DBU, 53 mL, 0.35 mol). The reaction mixture was cooled to 0° C. and propane-2-sulfonyl chloride (31.2 mL, 0.28 mol) was added drop-wise. The mixture was then stirred at room temperature for 18 hours. The reaction was monitored by proton NMR: additional propane-2-sulfonyl chloride (2.8 mL, 25 mmol) was added and the mixture was stirred at room temperature for an additional 18 hours. Again the reaction was monitored by NMR and additional propane-2-sulfonyl chloride (2.8 mL, 25 mmol) was added. After 2.5 hours the reaction was complete according to NMR analysis. Water (500 mL) was added and the layers were separated. The aqueous layer was extracted with methylene chloride, and the combined organic layers were dried over sodium sulfate, filtered and concentrated in vacuo. The residue was dissolved in methylene chloride and washed with aqueous hydrochloric acid (1N, 2×300 mL), dried over sodium sulfate, filtered and concentrated in vacuo to afford N-[(3S,4S)-4-(4-bromophenoxy)tetrahydrofuran-3-yl]propane-2-sulfonamide as an orange/brown oil. Yield: 92.5 g, 0.254 mol, 100%. $^1$H NMR (300 MHz, CDCl$_3$) δ 1.36 (d, J=7 Hz, 3H), 1.38 (d, J=7 Hz, 3H), 3.15 (septet, J=7 Hz, 1H), 3.69 (dd, J=8.5, 8.5 Hz, 1H), 3.93 (dd, J=10.6, 1.5 Hz, 1H), 4.10-4.28 (m, 3H), 4.72-4.81 (m, 2H), 6.77 (d, J=9.1 Hz, 2H), 7.41 (d, J=9.1 Hz, 2H). The absolute configuration of this material was established via X-ray crystallographic analysis of a crystal of N-[(3S,4S)-4-(4-bromophenoxy)tetrahydrofuran-3-yl]propane-2-sulfonamide grown from a heptane/ethyl acetate solution. The results are described below.

A 0.90 Å data set (maximum sin Θ/λ=0.56) was collected on a Bruker APEX diffractometer. The final R-index was 3.61%.

TABLE 1

Crystal data and structure refinement

| | |
|---|---|
| Empirical formula | C$_{13}$H$_{18}$NO$_4$SBr |
| Formula weight | 364.25 |
| Temperature | 298(2) K |
| Wavelength | 1.54178 Å |
| Crystal system | Monoclinic |
| Space group | P2(1) |
| Unit cell dimensions | a = 5.9363(2) Å    α = 90°. |
| | b = 10.5879(3) Å    β = 103.2060(10)°. |
| | c = 12.8451(3) Å    γ = 90°. |
| Volume | 786.00(4) Å$^3$ |
| Z | 2 |
| Density (calculated) | 1.539 Mg/m$^3$ |
| Absorption coefficient | 4.921 mm$^{-1}$ |
| F(000) | 372 |
| Crystal size | 0.10 × 0.30 × 0.46 mm$^3$ |
| Theta range for data collection | 3.53 to 58.95°. |
| Reflections collected | 3091 |
| Independent reflections | 1793 [R(int) = 0.0354] |
| Completeness to theta = 58.95° | 94.4% |
| Absorption correction | Empirical Absorption Correction |
| Refinement method | Full-matrix least-squares on F$^2$ |
| Data/restraints/parameters | 1793/1/182 |
| Goodness-of-fit on F$^2$ | 1.059 |
| Final R indices [I > 2sigma(I)] | R1 = 0.0361, wR2 = 0.0989 |
| R indices (all data) | R1 = 0.0363, wR2 = 0.0991 |
| Absolute structure parameter | 0.07(3) |
| Extinction coefficient | 0.0186(12) |
| Largest diff. peak and hole | 0.334 and −0.419 e.Å$^{-3}$ |

TABLE 2

Atomic coordinates (×10$^4$) and equivalent isotropic displacement parameters (Å$^2$ × 10$^3$). U(eq) is defined as one third of the trace of the orthogonalized U$_{ij}$ tensor.

| | x | y | z | U(eq) |
|---|---|---|---|---|
| O(1) | 16729(5) | −2517(4) | 8631(3) | 64(1) |
| C(2) | 15699(8) | −1365(5) | 8185(4) | 53(1) |
| C(3) | 13507(7) | −1173(4) | 8572(3) | 40(1) |
| C(4) | 13927(7) | −2000(5) | 9573(4) | 44(1) |
| C(5) | 15252(8) | −3101(5) | 9223(4) | 51(1) |
| O(6) | 11551(5) | −1714(3) | 7853(3) | 43(1) |
| C(7) | 10585(7) | −1088(4) | 6917(3) | 39(1) |
| C(8) | 8713(8) | −1672(5) | 6277(3) | 44(1) |
| C(9) | 7541(9) | −1109(5) | 5335(4) | 53(1) |

TABLE 2-continued

Atomic coordinates (×10$^4$) and equivalent isotropic displacement parameters (Å$^2$ × 10$^3$). U(eq) is defined as one third of the trace of the orthogonalized U$_{ij}$ tensor.

| | x | y | z | U(eq) |
|---|---|---|---|---|
| C(10) | 8294(10) | 50(5) | 5049(4) | 53(1) |
| C(11) | 10210(9) | 625(5) | 5669(4) | 59(1) |
| C(12) | 11377(9) | 69(5) | 6625(4) | 52(1) |
| N(13) | 11853(6) | −2321(4) | 9909(3) | 49(1) |
| S(14) | 11933(2) | −2739(1) | 11126(1) | 44(1) |
| O(15) | 14164(7) | −3235(4) | 11567(3) | 68(1) |
| O(16) | 9939(7) | −3478(4) | 11111(3) | 71(1) |
| C(17) | 11817(10) | −1310(5) | 11862(4) | 60(1) |
| C(18) | 11798(15) | −1658(9) | 13017(5) | 91(2) |
| C(19) | 9823(14) | −497(8) | 11370(6) | 94(2) |
| Br(20) | 6647(1) | 861(1) | 3780(1) | 84(1) |

TABLE 3

Bond lengths [Å] and angles [°].

| | | | |
|---|---|---|---|
| O(1)—C(2) | 1.425(7) | N(13)—C(4)—C(3) | 113.7(4) |
| O(1)—C(5) | 1.426(6) | N(13)—C(4)—C(5) | 116.2(4) |
| C(2)—C(3) | 1.509(6) | C(3)—C(4)—C(5) | 100.7(4) |
| C(3)—O(6) | 1.428(5) | O(1)—C(5)—C(4) | 104.2(4) |
| C(3)—C(4) | 1.528(6) | C(7)—O(6)—C(3) | 119.1(3) |
| C(4)—N(13) | 1.436(6) | C(8)—C(7)—O(6) | 115.1(4) |
| C(4)—C(5) | 1.530(7) | C(8)—C(7)—C(12) | 120.8(4) |
| O(6)—C(7) | 1.378(5) | O(6)—C(7)—C(12) | 124.0(4) |
| C(7)—C(8) | 1.370(6) | C(7)—C(8)—C(9) | 120.4(5) |
| C(7)—C(12) | 1.394(7) | C(10)—C(9)—C(8) | 119.0(5) |
| C(8)—C(9) | 1.386(6) | C(11)—C(10)—C(9) | 121.0(5) |
| C(9)—C(10) | 1.383(8) | C(11)—C(10)—Br(20) | 119.4(4) |
| C(10)—C(11) | 1.373(7) | C(9)—C(10)—Br(20) | 119.6(4) |
| C(10)—Br(20) | 1.904(5) | C(10)—C(11)—C(12) | 120.1(5) |
| C(11)—C(12) | 1.396(7) | C(11)—C(12)—C(7) | 118.5(5) |
| N(13)—S(14) | 1.615(3) | C(4)—N(13)—S(14) | 121.2(3) |
| S(14)—O(16) | 1.415(4) | O(16)—S(14)—O(15) | 120.2(3) |
| S(14)—O(15) | 1.417(4) | O(16)—S(14)—N(13) | 107.4(2) |
| S(14)—C(17) | 1.794(6) | O(15)—S(14)—N(13) | 107.8(2) |
| C(17)—C(19) | 1.483(9) | O(16)—S(14)—C(17) | 110.0(3) |
| C(17)—C(18) | 1.532(8) | O(15)—S(14)—C(17) | 104.3(3) |
| C(2)—O(1)—C(5) | 109.0(3) | N(13)—S(14)—C(17) | 106.4(2) |
| O(1)—C(2)—C(3) | 107.8(4) | C(19)—C(17)—C(18) | 111.7(6) |
| O(6)—C(3)—C(2) | 111.6(4) | C(19)—C(17)—S(14) | 112.8(4) |
| O(6)—C(3)—C(4) | 105.5(3) | C(18)—C(17)—S(14) | 108.5(5) |
| C(2)—C(3)—C(4) | 102.3(4) | | |

Symmetry transformations used to generate equivalent atoms

TABLE 4

Anisotropic displacement parameters (Å$^2$ × 10$^3$). The anisotropic displacement factor exponent takes the form: −2π$^2$ [h$^2$ a *$^2$U$_{11}$ + ... + 2 h k a * b * U$_{12}$]

| | U$_{11}$ | U$_{22}$ | U$_{33}$ | U$_{23}$ | U$_{13}$ | U$_{12}$ |
|---|---|---|---|---|---|---|
| O(1) | 46(2) | 70(2) | 84(3) | 20(2) | 30(2) | 10(2) |
| C(2) | 46(3) | 54(3) | 59(3) | 4(3) | 15(2) | −8(2) |
| C(3) | 37(2) | 44(3) | 37(2) | −1(2) | 4(2) | −3(2) |
| C(4) | 33(2) | 59(3) | 37(2) | 6(2) | 2(2) | −9(2) |
| C(5) | 40(2) | 51(3) | 62(3) | 13(3) | 13(2) | 3(2) |
| O(6) | 43(2) | 43(2) | 37(2) | 4(1) | 1(1) | −10(1) |
| C(7) | 39(2) | 44(2) | 35(2) | 1(2) | 8(2) | 0(2) |
| C(8) | 45(2) | 44(2) | 42(2) | −1(2) | 8(2) | −7(2) |
| C(9) | 48(2) | 66(3) | 38(2) | 3(2) | −3(2) | −4(2) |
| C(10) | 67(3) | 57(3) | 34(2) | 8(2) | 7(2) | 2(3) |
| C(11) | 72(3) | 56(4) | 46(2) | 7(3) | 9(2) | −8(3) |
| C(12) | 58(3) | 54(3) | 44(2) | 1(2) | 9(2) | −6(2) |
| N(13) | 37(2) | 81(3) | 27(2) | 8(2) | 5(2) | −7(2) |
| S(14) | 48(1) | 46(1) | 38(1) | 9(1) | 8(1) | 0(1) |
| O(15) | 57(2) | 88(3) | 53(2) | 19(2) | −1(2) | 23(2) |

TABLE 4-continued

Anisotropic displacement parameters (Å$^2$ × 10$^3$). The anisotropic displacement factor exponent takes the form: $-2\pi^2$ [h$^2$ a*$^2$U$_{11}$ + ... + 2 h k a* b* U$_{12}$]

| | U$_{11}$ | U$_{22}$ | U$_{33}$ | U$_{23}$ | U$_{13}$ | U$_{12}$ |
|---|---|---|---|---|---|---|
| O(16) | 69(2) | 92(3) | 52(2) | 10(2) | 15(2) | −34(2) |
| C(17) | 72(3) | 68(4) | 40(2) | −2(3) | 12(3) | −2(3) |
| C(18) | 116(5) | 108(6) | 48(3) | −7(4) | 17(3) | −9(5) |
| C(19) | 106(6) | 93(5) | 76(4) | −10(4) | 7(4) | 36(4) |
| Br(20) | 100(1) | 84(1) | 56(1) | 25(1) | −10(1) | 3(1) |

TABLE 5

Hydrogen coordinates (×10$^4$) and isotropic displacement parameters (Å$^2$ × 10$^3$).

| | x | y | z | U(eq) |
|---|---|---|---|---|
| H(2A) | 15347 | −1408 | 7411 | 80 |
| H(2B) | 16753 | −666 | 8412 | 80 |
| H(3A) | 13257 | −285 | 8730 | 80 |
| H(4A) | 14969 | −1550 | 10157 | 80 |
| H(5A) | 16148 | −3550 | 9838 | 80 |
| H(5B) | 14199 | −3690 | 8779 | 80 |
| H(8A) | 8225 | −2452 | 6477 | 80 |
| H(9A) | 6268 | −1504 | 4900 | 80 |
| H(11A) | 10730 | 1387 | 5450 | 80 |
| H(12A) | 12656 | 462 | 7058 | 80 |
| H(13A) | 10543 | −2290 | 9454 | 80 |
| H(17A) | 13237 | −832 | 11873 | 80 |
| H(18A) | 11746 | −902 | 13423 | 80 |
| H(18B) | 13173 | −2126 | 13328 | 80 |
| H(18C) | 10462 | −2166 | 13025 | 80 |
| H(19A) | 9846 | 254 | 11792 | 80 |
| H(19B) | 8408 | −949 | 11342 | 80 |
| H(19C) | 9924 | −270 | 10659 | 80 |

Step 7. Synthesis of N-[(3S,4S)-4-(biphenyl-4-yloxy)tetrahydrofuran-3-yl]propane-2-sulfonamide To a microwave vial was added N-[(3S,4S)-4-(4-bromophenoxy)tetrahydrofuran-3-yl]propane-2-sulfonamide (124 mg, 0.340 mmol), phenylboronic acid (63.5 mg, 0.521 mmol), dicyclohexyl(2',4',6'-triisopropylbiphenyl-2-yl)phosphine (XPhos, 16.2 mg, 0.034 mmol), palladium(II) acetate (5.2 mg, 0.023 mmol) and potassium fluoride (99.6 mg, 1.71 mmol). The vial was capped, and purged three times with nitrogen/vacuum. A 1:1 mixture of degassed methanol/toluene (1.5 mL) was added and the reaction was subjected to microwave irradiation at 130° C. for 30 minutes. The solvent was removed in vacuo and the residue was partitioned between ethyl acetate and saturated aqueous sodium chloride solution. The aqueous layer was extracted twice with ethyl acetate, and the organic layers were combined, dried over sodium sulfate, filtered, and concentrated in vacuo. The residue was purified by silica gel chromatography (Gradient: 10% to 25% ethyl acetate in heptane), to afford the title compound as a solid. Yield: 90 mg, 0.25 mmol, 73%. $^1$H NMR (400 MHz, CDCl$_3$) δ 1.37 (d, J=6.8 Hz, 3H), 1.40 (d, J=6.8 Hz, 3H), 3.17 (septet, J=6.8 Hz, 1H), 3.76 (dd, J=8.6, 8.6 Hz, 1H), 4.01 (dd, J=10.6, 1.6 Hz, 1H), 4.16-4.30 (m, 3H), 4.84 (m, 1H), 5.09 (d, J=9.4 Hz, 1H), 6.97 (d, J=8.7 Hz, 2H), 7.34 (t, J=7.4 Hz, 1H), 7.44 (dd, J=7.6, 7.6 Hz, 2H), 7.55 (m, 4H). $^{13}$C NMR (100 MHz, CDCl$_3$) δ 16.48, 16.55, 54.27, 55.35, 70.29, 71.96, 75.87, 115.85, 126.65, 126.88, 128.34, 128.68, 135.11, 140.25, 155.93.

Example 3

N-{(3S,4S)-4-[(2'-cyanobiphenyl-4-yl)oxy]tetrahydrofuran-3-yl}propane-2-sulfonamide

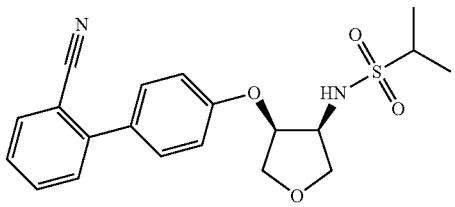 [SMILES: CC(C)S(=O)(=O)N[C@H]1COC[C@H]1Oc1ccc(-c2ccccc2C#N)cc1]

The title compound was prepared according to the general procedure for the synthesis of Example 2, except that (2-cyanophenyl)boronic acid was used in place of phenylboronic acid, affording product as a solid. Yield: 675.3 mg, 1.75 mmol, 85%. LCMS m/z 387.0 (M+1). $^1$H NMR (500 MHz, CDCl$_3$) δ 1.36 (d, J=6.8 Hz, 3H), 1.39 (d, J=6.8 Hz, 3H), 3.19 (septet, J=6.8 Hz, 1H), 3.77 (dd, J=8.8, 8.8 Hz, 1H), 3.98 (dd, J=10.6, 1.6 Hz, 1H), 4.16 (dd, J=7.9, 7.9 Hz, 1H), 4.21 (dd, J=10.6, 4.3 Hz, 1H) 4.30 (m, 1H), 4.82 (m, 1H), 5.53 (d, J=9.6 Hz, 1H), 7.03 (d, J=8.8 Hz, 2H), 7.43 (ddd, J=7.7, 7.7, 1.1 Hz, 1H), 7.48 (br d, J=7.9 Hz, 1H), 7.51 (d, J=8.8 Hz, 2H), 7.63 (ddd, J=7.7, 7.7, 1.4 Hz, 1H), 7.75 (br dd, J=7.8, 1.1 Hz, 1H). $^{13}$C NMR (125 MHz, CDCl$_3$) δ 16.19, 16.24, 53.89, 55.03, 69.86, 71.62, 75.48, 110.47, 115.39, 118.53, 127.00, 129.53, 129.86, 131.26, 132.58, 133.35, 144.32, 156.76.

Example 4

N-{(3S,4S)-4-[4-(5-cyano-2-thienyl)phenoxy]tetrahydrofuran-3-yl}propane-2-sulfonamide

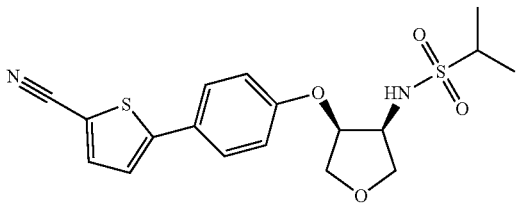 [SMILES: CC(C)S(=O)(=O)N[C@H]1COC[C@H]1Oc1ccc(-c2ccc(C#N)s2)cc1]

The title compound was prepared according to the general procedure for the synthesis of Example 2, except that (5-cyano-2-thienyl)boronic acid was used in place of phenylboronic acid, affording product as a solid. Yield: 365 mg, 0.93 mmol, 58%. LCMS m/z 393.5 (M+1). $^1$H NMR (500 MHz, CDCl$_3$) δ 1.39 (d, J=6.8 Hz, 3H), 1.41 (d, J=6.8 Hz, 3H), 3.21 (septet, J=6.8 Hz, 1H), 3.77 (dd, J=8.8, 8.8 Hz, 1H), 3.99 (dd, J=10.7, 1.6 Hz, 1H), 4.18 (dd, J=7.8, 7.8 Hz, 1H), 4.23 (dd, J=10.7, 4.3 Hz, 1H), 4.30 (m, 1H), 4.88 (m, 1H), 5.31 (d, J=9.8 Hz, 1H), 6.97 (d, J=8.9 Hz, 2H), 7.19 (d, J=3.9 Hz, 1H), 7.53 (d, J=8.8 Hz, 2H), 7.58 (d, J=3.9 Hz, 1H). $^{13}$C NMR (125

MHz, CDCl₃) δ 16.35, 54.07, 55.26, 69.84, 71.73, 75.84, 107.00, 114.23, 116.02, 122.36, 125.87, 127.67, 138.35, 151.01, 157.40.

Example 5

N-{(1S,2R)-2-[(2'-cyanobiphenyl-4-yl)oxy]cyclopentyl}propane-2-sulfonamide

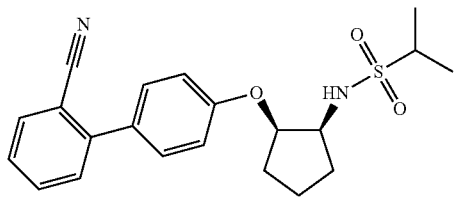 [SMILES: CC(C)S(=O)(=O)N[C@H]1CCC[C@H]1Oc1ccc(-c2ccccc2C#N)cc1]

Step 1. Synthesis of trans-2-(4-bromophenoxy)cyclopentanol

6-Oxabicyclo[3.1.0]hexane (2.04 mL, 23.5 mmol), 4-bromophenol (4.49 g, 26.0 mmol), cesium carbonate (99%, 8.93 g, 27.1 mmol) and benzyltriethylammonium chloride (99%, 1.09 g, 4.74 mmol) were suspended in dioxane (65 mL) and heated at reflux for 18 hours. Additional 6-oxabicyclo[3.1.0]hexane (0.50 mL, 5.8 mmol) was added, and heating was continued for 66 hours. Again, 6-oxabicyclo[3.1.0]hexane (0.50 mL, 5.8 mmol) was added, and the reaction mixture was heated at reflux for an additional 18 hours. The reaction was then cooled to room temperature, concentrated in vacuo and partitioned between saturated aqueous sodium bicarbonate solution and ethyl acetate. The organic layer was washed with saturated aqueous sodium chloride solution, dried over calcium sulfate, filtered and concentrated under reduced pressure to afford a golden oil, which was purified via chromatography on silica gel (Gradient: 0% to 20% ethyl acetate in heptane) to provide product as an oil. Yield: 3.21 g, 12.5 mmol, 48%. GCMS m/z 256, 258 (M⁺). ¹H NMR (400 MHz, CDCl₃) δ 1.64 (d, J=3.7 Hz, 1H), 1.60-1.68 (m, 1H), 1.70-1.88 (m, 3H), 2.07 (m, 1H), 2.17 (m, 1H), 4.30 (m, 1H), 4.48 (m, 1H), 6.80 (d, J=9.0 Hz, 2H), 7.37 (d, J=9.0 Hz, 2H).

Step 2. Synthesis of trans-2-(4-bromophenoxy)cyclopentyl methanesulfonate

The title compound of Step 2 was prepared according to the general procedure for the synthesis of trans-4-(4-bromophenoxy)tetrahydrofuran-3-yl methanesulfonate in Example 2, except that trans-2-(4-bromophenoxy)cyclopentanol was used in place of trans-4-(4-bromophenoxy)tetrahydrofuran-3-ol, and the reaction mixture was quenched by addition of saturated aqueous ammonium chloride solution. The organic layer was then washed with saturated aqueous ammonium chloride solution, washed with saturated aqueous sodium chloride solution, dried over sodium sulfate, filtered and concentrated in vacuo to provide product as a brown oil. Yield: 3.86 g, 11.5 mmol, 98%. ¹H NMR (400 MHz, CDCl₃) δ 1.79-2.00 (m, 4H), 2.14-2.26 (m, 2H), 3.03 (s, 3H), 4.78 (m, 1H), 5.07 (m, 1H), 6.82 (d, J=9.0 Hz, 2H), 7.39 (d, J=9.1 Hz, 2H).

Step 3. Synthesis of cis-2-azidocyclopentyl 4-bromophenyl ether

To a solution of trans-2-(4-bromophenoxy)cyclopentyl methanesulfonate (3.52 g, 10.5 mmol) in dimethylformamide (22 mL) was added sodium azide (897 mg, 13.7 mmol) and the reaction was heated at 100° C. for 18 hours. The reaction was cooled to room temperature and partitioned between ethyl acetate and 1N aqueous lithium chloride solution. The aqueous layer was extracted with ethyl acetate, and the combined organic layers were washed with saturated aqueous sodium chloride solution, dried over calcium sulfate, filtered and concentrated in vacuo to provide product as a brown oil, which was used in the next step without additional purification. Yield: 2.59 g, 9.18 mmol, 87%. ¹H NMR (400 MHz, CDCl₃) δ 1.65-1.73 (m, 1H), 1.89-2.05 (m, 5H), 3.74 (m, 1H), 4.66 (m, 1H), 6.83 (d, J=9.0 Hz, 2H), 7.39 (d, J=9.0 Hz, 2H).

Step 4. Synthesis of cis-2-(4-bromophenoxy)cyclopentanamine

A solution of cis-2-azidocyclopentyl 4-bromophenyl ether from the previous step (2.59 g, 9.18 mmol) in tetrahydrofuran (63 mL) and water (5.0 mL) was treated with polymer-supported triphenylphosphine (3 mmol/g, 7.15 g, 21.5 mmol). The reaction was stirred for 18 hours, then filtered through Celite®. The filter pad was rinsed with tetrahydrofuran, then with a mixture of methylene chloride and methanol, and the combined filtrates were concentrated in vacuo, and azeotroped with ethanol. The residue was purified by chromatography on silica gel (Gradient: 0% to 10% methanol in ethyl acetate) to afford product as a light brown oil. Yield: 1.43 g, 5.58 mmol, 61%. MS (APCI) m/z 257.9 (M+1). ¹H NMR (400 MHz, CDCl₃) δ 1.47 (br s, 2H), 1.56-1.68 (m, 2H), 1.78-1.88 (m, 2H), 1.91-1.99 (m, 2H), 3.35 (ddd, J=8.6, 7.0, 4.7 Hz, 1H), 4.42 (m, 1H), 6.80 (d, J=9.0 Hz, 2H), 7.37 (d, J=9.0 Hz, 2H).

Step 5. Synthesis of cis-N-[2-(4-bromophenoxy)cyclopentyl]propane-2-sulfonamide To a slurry of cis-2-(4-bromophenoxy)cyclopentanamine (1.43 g, 5.58 mmol) in methylene chloride (38.5 mL) was added 1,8-diazabicyclo[5.4.0]undec-7-ene (1.40 mL, 9.36 mmol), then 4-(dimethylamino)pyridine (915 mg, 7.49 mmol). The reaction mixture was cooled to 0° C. and propane-2-sulfonyl chloride (0.937 mL, 8.38 mmol) was added drop-wise. The mixture was then allowed to warm to room temperature and stir for 18 hours. The reaction was treated with 1N aqueous hydrochloric acid, and the organic layer was washed with saturated aqueous sodium chloride solution, dried over calcium sulfate, filtered and concentrated in vacuo. The resulting residue was purified by silica gel chromatography (Gradient: 0% to 15% ethyl acetate in heptane) to provide product as a colorless gum. Yield: 1.586 g, 4.38 mmol, 78%.

Step 6. Isolation of N-[(1S,2R)-2-(4-bromophenoxy)cyclopentyl]-propane-2-sulfonamide Separation of the enantiomers comprising cis-N-[2-(4-bromophenoxy)cyclopentyl]propane-2-sulfonamide (1.586 g, 4.38 mmol) was carried out by chiral chromatography. Column: Chiralpak® AD-H, 2.1×25 cm, 5 μm; Mobile phase: 75:25 carbon dioxide: methanol; Flow rate: 65 g/min. The first-eluting compound was enantiomer N-[(1R,2S)-2-(4-bromophenoxy)cyclopentyl]propane-2-sulfonamide (767 mg, 2.12 mmol, 48%) and the second-eluting peak provided desired product N-[(1S,2R)-2-(4-bromophenoxy)cyclopentyl]propane-2-sulfonamide upon removal of solvent in vacuo. Yield: 758 mg, 2.09 mmol, 48%. The absolute stereochemistry of these enantiomers was assigned by analogy to their higher homologues (see Example 7). The title compound, synthesized in the following step, proved significantly more potent than its enantiomer (prepared in the same way from N-[(1R,2S)-2-(4-bromophenoxy)cyclopentyl]propane-2-sulfonamide. On this basis, the (1S,2R) configuration was assigned to N-[(1S,2R)-2-(4-bromophenoxy)cyclopentyl] propane-2-sulfonamide. MS (APCI) m/z 364.2 (M+1). $^1$H NMR (500 MHz, CDCl$_3$) δ 1.35 (d, J=6.8 Hz, 3H), 1.38 (d, J=6.8 Hz, 3H), 1.64 (m, 1H), 1.79-1.98 (m, 4H), 2.12 (m, 1H), 3.13 (septet, J=6.8 Hz, 1H), 3.86 (m, 1H), 4.59 (m, 1H), 4.63 (d, J=9.5 Hz, 1H), 6.78 (d, J=9.0 Hz, 2H), 7.39 (d, J=9.1 Hz, 2H). Data for N-[(1R,2S)-2-(4-bromophenoxy)cyclopentyl]propane-2-sulfonamide: MS (APCI) m/z 362.2, 364.2 (M+1). $^1$H NMR (500 MHz, CDCl$_3$) δ 1.35 (d, J=6.8 Hz, 3H), 1.38 (d, J=6.8 Hz, 3H), 1.58-1.68 (m, 1H), 1.78-1.97 (m, 4H), 2.12 (m, 1H), 3.13 (septet, J=6.8 Hz, 1H), 3.86 (m, 1H), 4.59 (m, 1H), 4.64 (d, J=9.5 Hz, 1H), 6.78 (d, J=9.1 Hz, 2H), 7.39 (d, J=9.0 Hz, 2H).

Step 7. Synthesis of compound N-{(1S,2R)-2-[(2'-cyanobiphenyl-4-yl)oxy]cyclopentyl}propane-2-sulfonamide The title compound of Step 7 was prepared according to the general procedure for the synthesis of Example 2, except that N-[(1S,2R)-2-(4-bromophenoxy)cyclopentyl]propane-2-sulfonamide was used instead of N-[(3S,4S)-4-(4-bromophenoxy)tetrahydrofuran-3-yl]propane-2-sulfonamide, and (2-cyanophenyl)boronic acid was added in place of phenylboronic acid. After the reaction mixture was concentrated in vacuo, it was directly purified by silica gel chromatography in this case (Eluant: 25% ethyl acetate in heptane), to afford the product as a sticky white foam. Trituration with hexanes gave product as a white powder. Yield: 53 mg, 0.14 mmol, 82%. MS (APCI) m/z 382.9 (M−1). $^1$H NMR (400 MHz, CDCl$_3$) δ 1.36 (d, J=6.7 Hz, 3H), 1.40 (d, J=6.8 Hz, 3H), 1.66 (m, 1H), 1.82-2.03 (m, 4H), 2.15 (m, 1H), 3.15 (septet, J=6.8 Hz, 1H), 3.90 (m, 1H), 4.70 (m, 2H), 7.01 (d, J=8.8 Hz, 2H), 7.42 (ddd, J=7.6, 7.6, 1.2 Hz, 1H), 7.50 (m, 1H), 7.52 (d, J=8.8 Hz, 2H), 7.64 (ddd, J=7.7, 7.7, 1.4 Hz, 1H), 7.76 (m, 1H).

Example 6

N-{(1S,2R)-2-[4-(5-cyano-2-thienyl)phenoxy]cyclopentyl}propane-2-sulfonamide

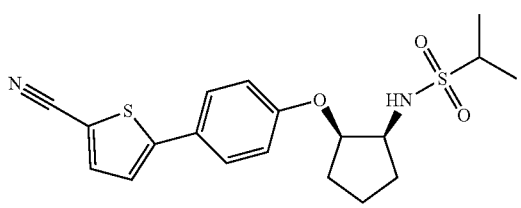 [SMILES: CC(C)S(=O)(=O)N[C@H]1CCC[C@H]1Oc1ccc(-c2ccc(C#N)s2)cc1]

To a microwave vial was added N-[(1S,2R)-2-(4-bromophenoxy)cyclopentyl]propane-2-sulfonamide (150.0 mg, 0.414 mmol), (5-cyano-2-thienyl)boronic acid (95.0 mg, 0.621 mmol), dicyclohexyl(2',4',6'-triisopropylbiphenyl-2-yl)phosphine (20.2 mg, 0.0410 mmol), palladium(II) acetate (7.4 mg, 0.033 mmol) and potassium fluoride (120 mg, 2.07 mmol). Dimethoxyethane (1.5 mL) was added and the reaction mixture was purged three times with nitrogen/vacuum. The reaction was subjected to microwave irradiation at 120° C. for 2 hours, then solvent was removed in vacuo and the residue was partitioned between ethyl acetate and saturated aqueous sodium chloride solution. The aqueous layer was extracted with ethyl acetate, and the organic layers were combined, dried over calcium sulfate, filtered, and concentrated in vacuo. The residue was purified by preparative thin layer chromatography on silica gel (Eluant: 40% ethyl acetate in heptane), to afford the title compound as a yellow oil which subsequently solidified. Yield: 104 mg, 0.266 mmol, 64%. LCMS m/z 391.0 (M+1). $^1$H NMR (500 MHz, CDCl$_3$) δ 1.36 (d, J=6.8 Hz, 3H), 1.39 (d, J=6.8 Hz, 3H), 1.66 (m, 1H), 1.81-1.94 (m, 3H), 1.99 (m, 1H), 2.14 (m, 1H), 3.15 (septet, J=6.8 Hz, 1H), 3.89 (m, 1H), 4.64 (d, J=9.5 Hz, 1H), 4.69 (m, 1H), 6.95 (d, J=8.7 Hz, 2H), 7.18 (d, J=4.0 Hz, 1H), 7.54 (d, J=8.7 Hz, 2H), 7.57 (d, J=3.9 Hz, 1H).

Example 7

N-{(1S,2R)-2-[(2'-cyanobiphenyl-4-yl)oxy]cyclohexyl}propane-2-sulfonamide

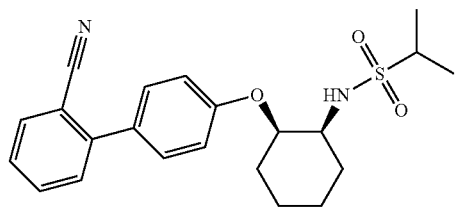 [SMILES: CC(C)S(=O)(=O)N[C@H]1CCCC[C@H]1Oc1ccc(-c2ccccc2C#N)cc1]

Step 1. Synthesis of trans-2-(4-bromophenoxy)cyclohexanol

Sodium metal (2.58 g, 112 mmol) was combined with absolute ethanol (200 mL) and allowed to react completely. 4-Bromophenol (19.4 g, 112 mmol) was added, and the reaction was stirred for 20 minutes, at which point 7-oxabicyclo[4.1.0]heptane (10.0 g, 102 mmol) was added, and the solution was heated at reflux for 15 hours. After removal of solvent in vacuo, the residue was partitioned between water (300 mL) and ethyl acetate (100 mL). The aqueous layer was extracted with ethyl acetate (2×100 mL), and the combined organic layers were washed with water (2×200 mL), dried over magnesium sulfate, filtered, and concentrated under reduced pressure. The resulting light tan solid was recrystallized from heptane (roughly 200 mL) to provide trans-2-(4-bromophenoxy)cyclohexanol as a fluffy white solid. Yield: 12.5 g, 46.1 mmol, 45%. $^1$H NMR (400 MHz, CDCl$_3$) δ 1.26-1.46 (m, 4H), 1.75-1.79 (m, 2H), 2.08-2.14 (m, 2H), 2.52 (d, J=2.1 Hz, 1H), 3.72 (m, 1H), 3.96 (ddd, J=10.3, 8.6, 4.4 Hz, 1H), 6.84 (d, J=9.0 Hz, 2H), 7.37 (d, J=9.0 Hz, 2H).

Step 2. Synthesis of (1R,2R)-2-(4-bromophenoxy)cyclohexyl acetate trans-2-(4-Bromophenoxy)cyclohexanol (5.305 g, 19.56 mmol) was dissolved in ethyl acetate (196 mL) and treated with vinyl acetate (3.37 g, 39.1 mmol), followed by lipase enzyme from Candida antarctica (Novozyme 435, Sigma L4777, lipase immobilized on acrylic resin, 5.3 g). The reaction was capped and stirred for 18 hours, then filtered through Celite® and rinsed with ethyl acetate (500 mL). Concentration of the filtrate in vacuo provided a pale yellow oil, which was purified via silica gel chromatography (Gradient: 0% to 10% ethyl acetate in heptane) to afford (1R,2R)-2-(4-bromophenoxy)cyclohexyl acetate, the less polar product, as a colorless oil. Yield: 2.047 g, 6.54 mmol, 33%. Data for (1R,2R)-2-(4-bromophenoxy)cyclohexyl acetate: $^1$H NMR (400 MHz, CDCl$_3$) δ 1.32-1.59 (m, 4H), 1.71-1.80 (m, 2H), 1.95 (s, 3H), 2.02-2.14 (m, 2H), 4.17 (ddd, J=9.6, 8.1, 4.4 Hz, 1H), 4.96 (m, 1H), 6.84 (d, J=9.0 Hz, 2H), 7.36 (d, J=9.1 Hz, 2H). Enantiomeric alcohol (1S,2S)-2-(4-bromophenoxy)cyclohexanol, the more polar product, was obtained as a white solid (3.57 g). Data for (1S,2S)-2-(4-bromophenoxy)cyclohexanol: $^1$H NMR (400 MHz, CDCl$_3$) δ 1.26-1.46 (m, 4H), 1.74-1.79 (m, 2H), 2.08-2.15 (m, 2H), 2.50 (br s, 1H), 3.72 (ddd, J=10.6, 8.5, 4.6 Hz, 1H), 3.96 (m, 1H), 6.84 (d, J=9.0 Hz, 2H), 7.38 (d, J=9.0 Hz, 2H). The absolute configurations of these compounds were assigned on the basis of an X-ray crystal structure of the enantiomer of N-[(1S,2R)-2-(4-bromophenoxy)cyclohexyl]propane-2-sulfonamide (see step 7 below).

Step 3. Synthesis of (1R,2R)-2-(4-bromophenoxy)cyclohexanol

A solution of (1R,2R)-2-(4-bromophenoxy)cyclohexyl acetate (2.047 g, 6.54 mmol) in methanol (12.2 mL) and water (0.32 mL) was cooled to 0° C. and treated with lithium hydroxide hydrate (95%, 1.73 g, 39.2 mmol). The reaction was stirred at 0° C. for 15 minutes, then allowed to warm and stir at room temperature for 18 hours. The methanol was removed under reduced pressure, and the aqueous residue was partitioned between ethyl acetate (200 mL) and water (100 mL). After extraction of the aqueous layer with ethyl acetate (100 mL), the combined organics were washed with saturated aqueous sodium chloride solution (100 mL), dried over magnesium sulfate, filtered and concentrated in vacuo to provide (1R,2R)-2-(4-bromophenoxy)cyclohexanol as a yellow oil. Yield: 1.76 g, 6.49 mmol, 99%. $^1$H NMR (400 MHz, CDCl$_3$) δ 1.26-1.46 (m, 4H), 1.74-1.79 (m, 2H), 2.08-2.14 (m, 2H), 3.72 (ddd, J=10.5, 8.4, 4.7 Hz, 1H), 3.96 (m, 1H), 6.84 (d, J=9.0 Hz, 2H), 7.37 (d, J=9.0 Hz, 2H).

Step 4. Synthesis of (1R,2R)-2-(4-bromophenoxy)cyclohexyl methanesulfonate

The title compound of Step 4 was prepared according to the general procedure for the synthesis of trans-2-(4-bromophenoxy)cyclopentyl methanesulfonate in Example 5, except that (1R,2R)-2-(4-bromophenoxy)cyclohexanol was used instead of trans-2-(4-bromophenoxy)cyclopentanol. (1R,2R)-2-(4-bromophenoxy)cyclohexyl methanesulfonate was obtained as a light golden oil. Yield: 3.60 g, 10.3 mmol, quantitative. $^1$H NMR (400 MHz, CDCl$_3$) δ 1.26-1.51 (m, 3H), 1.64-1.84 (m, 3H), 2.19 (m, 1H), 2.30 (m, 1H), 2.97 (s, 3H), 4.22 (ddd, J=10.2, 8.5, 4.6 Hz, 1H), 4.64 (ddd, J=10.6, 8.4, 4.9 Hz, 1H), 6.82 (d, J=9.1 Hz, 2H), 7.39 (d, J=9.1 Hz, 2H).

Step 5. Synthesis of (1R,2S)-2-azidocyclohexyl 4-bromophenyl ether

To a solution of (1R,2R)-2-(4-bromophenoxy)cyclohexyl methanesulfonate (3.55 g, 10.2 mmol) in dimethylformamide (21.8 mL) and water (2.43 mL) was added sodium azide (95%, 2.09 mg, 30.5 mmol) and the reaction was heated at 120° C. for 23 hours. The reaction was cooled to room temperature, diluted with water (400 mL) and extracted with ethyl acetate (4×400 mL). The combined organic layers were washed with aqueous lithium chloride solution (1N, 400 mL), washed with water (400 mL), and dried over magnesium sulfate. Filtration and removal of solvents in vacuo afforded (1R,2S)-2-azidocyclohexyl 4-bromophenyl ether as an orange oil, which was used in the next step without additional purification. Yield: 2.85 g, 9.62 mmol, 94%. $^1$H NMR (400 MHz, CDCl$_3$) δ 1.36-1.48 (m, 2H), 1.62-1.76 (m, 4H), 1.96-2.07 (m, 2H), 3.63 (m, 1H), 4.43 (m, 1H), 6.85 (d, J=9.0 Hz, 2H), 7.39 (d, J=8.9 Hz, 2H).

Step 6. Synthesis of (1S,2R)-2-(4-bromophenoxy)cyclohexanamine

A solution of (1R,2S)-2-azidocyclohexyl 4-bromophenyl ether from the previous step (2.85 g, 9.62 mmol) in tetrahydrofuran (59 mL) and water (4.6 mL) was treated with polymer-supported triphenylphosphine (3 mmol/g, 7.87 g, 23.6 mmol). The reaction was stirred for 18 hours, then filtered through Celite®. The filter pad was rinsed with tetrahydrofuran (250 mL), then with ethyl acetate (400 mL), and the combined filtrates were concentrated in vacuo, and azeotroped with ethanol. The residue was purified by chromatography on silica gel (Gradient: 0% to 10% methanol in dichloromethane) to afford (1S,2R)-2-(4-bromophenoxy)cyclohexanamine as a yellow oil. Yield: 1.82 g, 6.74 mmol, 70%. $^1$H NMR (400 MHz, CDCl$_3$) δ 1.33-1.55 (m, 4H), 1.66-1.75 (m, 3H), 2.00 (m, 1H), 2.07 (br s, 2H), 2.97 (m, 1H), 4.39 (m, 1H), 6.85 (d, J=9.0 Hz, 2H), 7.36 (d, J=9.0 Hz, 2H).

Step 7. Synthesis of N-[(1S,2R)-2-(4-bromophenoxy)cyclohexyl]propane-2-sulfonamide The title compound of Step 7 was prepared according to the general procedure for the synthesis of cis-N-[2-(4-bromophenoxy)cyclopentyl]propane-2-sulfonamide in Example 5, except that (1S,2R)-2-(4-bromophenoxy)cyclohexanamine was used in place of cis-2-(4-bromophenoxy)cyclopentanamine, and the product purification was carried out using a gradient of 0% to 1% methanol in dichloromethane. N-[(1S,2R)-2-(4-bromophenoxy)cyclohexyl]propane-2-sulfonamide was obtained as a white foam. Yield: 1.67 g, 4.44 mmol, 75%. $^1$H NMR (400 MHz, CDCl$_3$) δ 1.36 (d, J=6.9 Hz, 3H), 1.37 (d, J=6.9 Hz, 3H), 1.37-1.48 (m, 3H), 1.77-1.88 (m, 3H), 2.06 (m, 1H), 3.12 (septet, J=6.8 Hz, 1H), 3.54 (m, 1H), 4.48 (d, J=9.5 Hz, 1H), 4.54 (m, 1H), 6.84 (d, J=9.0 Hz, 2H), 7.39 (d, J=9.0 Hz, 2H). The enantiomer of N-[(1S,2R)-2-(4-bromophenoxy)cyclohexyl]propane-2-sulfonamide was prepared using similar chemistry to that described above in this Step 7, but employing (1S,2S)-2-(4-bromophenoxy)cyclohexanol as starting material instead of (1R,2R)-2-(4-bromophenoxy)cyclohexanol. The absolute stereochemistry of the enantiomer of N-[(1S,2R)-2-(4-bromophenoxy)cyclohexyl]propane-2-sulfonamide was established via X-ray crystallography.

Step 8. Synthesis of N-{(1S,2R)-2-[(2'-cyanobiphenyl-4-yl)oxy]cyclohexyl}propane-2-sulfonamide The title compound was prepared according to the general procedure for the synthesis of Example 2, except that N-[(1S,2R)-2-(4-bromophenoxy)cyclohexyl]propane-2-sulfonamide was used in place of N-[(3S,4S)-4-(4-bromophenoxy)tetrahydrofuran-3-yl]propane-2-sulfonamide, and the microwave irradiation was carried out at 140° C. for 55 minutes. The crude reaction mixture was then filtered through Celite® and rinsed with methanol. Removal of solvent in vacuo provided a brown solid, which was dissolved in ethyl acetate (100 mL) and washed with water (2×75 mL). The aqueous layers were extracted with ethyl acetate (75 mL), and the combined organic layers were washed with saturated aqueous sodium chloride solution (75 mL), dried over magnesium sulfate, filtered and concentrated in vacuo. The resulting colorless oil was purified by preparative thin layer chromatography on silica gel (Eluant: 1% methanol in dichloromethane) to provide the title compound as a white foam. Yield: 72 mg, 0.18 mmol, 34%. LCMS m/z 399 (M+1). $^1$H NMR (400 MHz, CDCl$_3$) δ 1.37 (d, J=7.2 Hz, 3H), 1.39 (d, J=7.0 Hz, 3H), 1.41-1.55 (m, 4H), 1.79-1.94 (m, 3H), 2.16 (m, 1H), 3.14 (septet, J=6.8 Hz, 1H), 3.59 (m, 1H), 4.52 (d, J=9.4 Hz, 1H), 4.66 (m, 1H), 7.06 (d, J=8.7 Hz, 2H), 7.42 (ddd, J=7.6, 7.6, 1.2 Hz, 1H), 7.50 (m, 1H), 7.52 (d, J=8.6 Hz, 2H), 7.64 (ddd, J=7.7, 7.7, 1.4 Hz, 1H), 7.76 (m, 1H). The biological activity of the title compound was >150 times improved over that of its enantiomer, which was prepared in the same way from the enantiomer of N-[(1S,2R)-2-(4-bromophenoxy)cyclohexyl]propane-2-sulfonamide.

Examples 8-54

Method A: Aryl coupling, exemplified by synthesis of trans-N-{4-[(2'-ethoxybiphenyl-4-yl)oxy]tetrahydrofuran-3-yl}propane-2-sulfonamide trans-N-[4-(4-Bromophenoxy)tetrahydrofuran-3-yl]propane-2-sulfonamide (91.1 mg, 0.250 mmol), (2-ethoxyphenyl)boronic acid (49.8 mg, 0.300 mmol), [1,1'-bis(diphenylphosphino)ferrocene]dichloropalladium(II) (95%, 38.5 mg, 0.050 mmol), and sodium carbonate (63.6 mg, 0.600 mmol) were combined in dioxane (3.2 mL) and water (0.8 mL) and subjected to microwave irradiation for 20 minutes at 150° C. The reaction was then filtered through Celite® and partitioned between water (10 mL) and diethyl ether (10 mL). The aqueous layer was extracted with additional diethyl ether (2×10 mL), and the organic layers were combined, dried over sodium sulfate, filtered, concentrated in vacuo, and purified by silica gel chromatography (Gradient: 15% to 35% ethyl acetate in heptane), to afford the title compound as a gum. Yield of pure fractions: 16.6 mg, 0.041 mmol, 16%. See Table 1 for characterization data.

Method B

Coupling of bromoaromatic and boronic acid mediated by tetrakis(triphenylphosphine)palladium(0)

A Suzuki coupling was carried via a method similar to that reported by K. Kawaguchi et al., *Journal of Organic Chemistry* 2007, 72, 5119-5128 and corresponding supporting information.

Method C

Coupling of Amine to Bromoaromatic, Mediated by tris(dibenzylideneacetone)dipalladium(0)

An amination reaction was carried out as described by X. Huang et al., *Journal of the American Chemical Society* 2003, 125, 6653-6655.

Method D

Ester Hydrolysis

Hydrolysis of the alkyl ester to the corresponding carboxylic acid was carried out under standard conditions, for instance with aqueous sodium hydroxide.

Method E

Preparation of cis-N-{4-[(4-substituted)phenoxy]tetrahydrofuran-3-yl}propanesulfonamides The boronic acid (0.1 mmol) was weighed into a vial and treated with a solution of cis-N-[4-(4-bromophenoxy)tetrahydrofuran-3-yl]propane-2-sulfonamide (18.2 mg, 0.05 mmol) in degassed ethanol (0.8 mL). Next, a solution of sodium carbonate (26.5 mg, 0.25 mmol) in water (0.1 mL) was added, and the reaction vial was purged twice with vacuum, then refilled with nitrogen. Tetrakis(triphenylphosphine)palladium(0) (2.9 mg, 0.0025 mmol) in degassed toluene (0.1 mL) was then added and the reaction was heated to 80° C. for 16 hours. Next, the reaction was treated with an aqueous solution of sodium hydroxide (1N, 1.5 mL) and ethyl acetate (2.3 mL) and the reaction vial was shaken and extracted three times with ethyl acetate. The combined organic layers were passed thru a solid phase extraction cartridge loaded with sodium sulfate, and the filtrate was concentrated in vacuo. The residue was dissolved in dimethyl sulfoxide (1 mL) and purified by preparative HPLC (Column: XBridge C$_{18}$, 5 μm, 19×100 mm; Solvent A: 0.1% ammonium hydroxide in water (v/v); Solvent B: 0.1% ammonium hydroxide in acetonitrile (v/v) using an appropriate gradient).

Method F

Preparation of N-[(1S,2R)-2-(N',N'-disubstituted-4-aminophenoxy)cyclohexyl]propane-2-sulfonamides The amine (0.35 mmol) was weighed into a vial. In a dry box was added degassed 2-methyl-2-butanol (0.4 mL), a spatula tip of dicyclohexyl(2',4',6'-triisopropylbiphenyl-2-yl)phosphine (XPhos, 0.7 mg, 0.0015 mmol), a spatula tip of tris(dibenzylideneacetone)dipalladium(0) (0.14 mg, 0.00025 mmol) and one potassium hydroxide pellet. The reaction was then flooded with nitrogen, evacuated using a vacuum, and refilled with nitrogen. After the mixture was shaken at room temperature for 15 minutes, it was treated with a solution of N-[(1S,2R)-2-(4-bromophenoxy)cyclohexyl]propane-2-sulfonamide (26.3 mg, 0.7 mmol) in degassed 2-methyl-2-butanol (0.4 mL) and shaken at 100° C. for 18 hours. The reaction was then treated with water (1.5 mL) and extracted with ethyl acetate (3×2.5 mL). The organic layers were combined, passed thru a solid phase extraction cartridge loaded with sodium sulfate, and concentrated in vacuo. {Note: to remove any tert-butoxycarbonyl protecting groups present after the coupling, a mixture of 1:1 trifluoroacetic acid/dichloromethane (0.5 mL) was added to the appropriate reactions, and then they were shaken at room temperature for 2 hours and concentrated in vacuo.} The residue was dissolved in dimethyl sulfoxide (1 mL), and purified by preparative HPLC (Column: XBridge C$_{18}$, 5 μm, 19×50 mm; Solvent A: 0.1% trifluoroacetic acid in water (v/v); Solvent B: 0.1% trifluoroacetic acid in acetonitrile (v/v) using an appropriate gradient).

TABLE 1

| Ex # | Structure | Method | IUPAC Name | $^1$H NMR (400 MHz, CDCl$_3$), $^{13}$C NMR (100 MHz, CDCl$_3$) (unless otherwise indicated): observed peaks, δ (ppm); Mass spectrum: observed ion m/z; additional data |
|---|---|---|---|---|
| 8 | 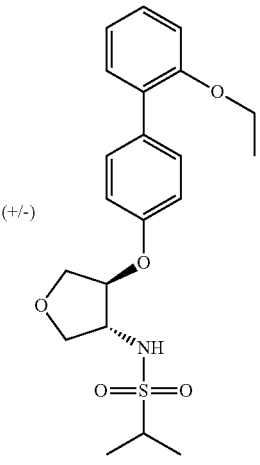 [SMILES: CCOc1ccccc1-c1ccc(O[C@@H]2COC[C@H]2NS(=O)(=O)C(C)C)cc1] (+/−) | A | trans-N-{4-[(2'-ethoxy biphenyl-4-yl)oxy] tetrahydro furan-3-yl}propane-2-sulfonamide. | $^1$H NMR δ 1.39 (m, 9H), 3.22 (septet, J = 6.8 Hz, 1H), 3.86 (m, 1H), 3.98 (dd, J = 10.4, 1.9 Hz, 1H), 4.05 (q, J = 6.9 Hz, 2H), 4.14 (m, 2H), 4.29 (dd, J = 10.4, 4.8 Hz, 1H), 4.93 (m, 1H), 5.02 (br d, J = 8.5 Hz, 1H), 6.96–7.03 (m, 2H), 7.01 (d, J = 8.9 Hz, 2H), 7.26–7.33 (m, 2H), 7.53 (d, J = 8.9 Hz, 2H). LCMS m/z 406.1 (M + 1). |
| 9 | 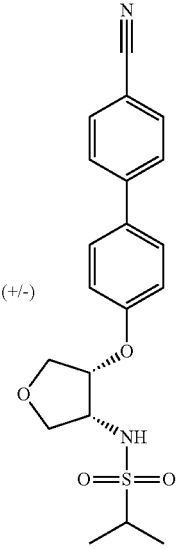 [SMILES: CC(C)S(=O)(=O)N[C@@H]1COC[C@@H]1Oc1ccc(-c2ccc(C#N)cc2)cc1] (+/−) | B | cis-N-{4-[(4'-cyano biphenyl-4-yl)oxy]tetra hydrofuran-3-yl}propane-2-sulfonamide | $^1$H NMR δ 1.36 (J = 6.8 Hz, 3H), 1.38 (d, J = 6.8 Hz, 3H), 3.17 (septet, J = 6.8 Hz, 1H), 3.73 (dd, J = 9.0, 8.6 Hz, 1H), 3.99 (dd, J = 10.7, 1.7 Hz, 1H), 4.14–4.30 (m, 3H), 4.86 (m, 1H), 5.00 (d, J = 9.6 Hz, 1H), 6.99 (d, J = 8.8 Hz, 2H), 7.54 (d, J = 8.9 Hz, 2H), 7.62 (d, half of AB quartet, J = 8.6 Hz, 2H), 7.69 (d, half of AB quartet, J = 8.7 Hz, 2H). $^{13}$C NMR δ 16.53, 54.33, 55.42, 70.12, 71.95, 75.94, 110.33, 116.08, 118.90, 127.12, 128.58, 132.52, 132.83, 144.63, 156.99. |
| 10 | 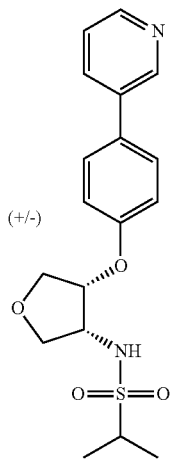 [SMILES: CC(C)S(=O)(=O)N[C@@H]1COC[C@@H]1Oc1ccc(-c2cccnc2)cc1] (+/−) | B | cis-N-[4-(4-pyridin-3-ylphenoxy) tetrahydro furan-3-yl]propane-2-sulfonamide | $^1$H NMR δ 1.35 (d, J = 6.8 Hz, 3H), 1.37 (d, J = 6.8 Hz, 3H), 3.15 (septet, J = 6.8 Hz, 1H), 3.74 (dd, J = 8.8, 8.8 Hz, 1H), 3.99 (dd, J = 10.7, 1.7 Hz, 1H), 4.14–4.30 (m, 3H), 4.85 (m, 1H), 5.38 (d, J = 9.5 Hz, 1H), 6.96 (d, J = 8.8 Hz, 2H), 7.34 (br dd, J = 7.9, 4.8 Hz, 1H), 7.50 (d, J = 8.8 Hz, 2H), 7.81 (ddd, J = 7.9, 2.2, 1.7 Hz, 1H), 8.55 (dd, J = 4.8, 1.6 Hz, 1H), 8.77 (br d, J = 2 Hz, 1H). $^{13}$C NMR δ 16.55, 54.32, 55.47, 70.15, 71.99, 76.00, 116.14, 123.50, 128.44, 131.53, 133.89, 135.75, 147.78, 147.96, 156.63. |

TABLE 1-continued

| Ex # | Structure | Method | IUPAC Name | $^1$H NMR (400 MHz, CDCl$_3$), $^{13}$C NMR (100 MHz, CDCl$_3$) (unless otherwise indicated): observed peaks, δ (ppm); Mass spectrum: observed ion m/z; additional data |
|---|---|---|---|---|
| 11 | 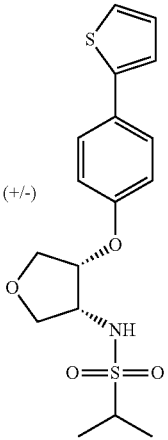 (+/−) | B | cis-N-{4-[4-(2-thienyl)phenoxy]tetrahydrofuran-3-yl}propane-2-sulfonamide | $^1$H NMR δ 1.36 (d, J = 6.8 Hz, 3H), 1.39 (d, J = 6.8 Hz, 3H), 3.16 (septet, J = 6.8 Hz, 1H), 3.73 (dd, J = 8.5, 9 Hz, 1H), 3.98 (dd, J = 10.6, 1.8 Hz, 1H), 4.14-4.28 (m, 3H), 4.82 (m, 1H), 4.90 (d, J = 9.5 Hz, 1H), 6.89 (d, J = 8.9 Hz, 2H), 7.07 (dd, J = 5.1, 3.6 Hz, 1H), 7.22 (dd, J = 3.6, 1.2 Hz, 1H), 7.25 (dd, J = 5.1, 1.1 Hz, 1H), 7.55 (d, J = 8.9 Hz, 2H). $^{13}$C NMR observed peaks: δ 16.57, 16.61, 54.39, 55.42, 70.35, 71.99, 75.97, 115.97, 122.51, 124.30, 127.43, 127.98, 143.61, 155.90. |
| 12 | 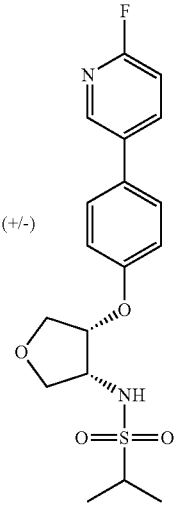 (+/−) | Ex 2 | cis-N-{4-[4-(6-fluoropyridin-3-yl)phenoxy]tetrahydrofuran-3-yl}propane-2-sulfonamide | $^1$H NMR δ 1.35 (d, J = 6.8 Hz, 3H), 1.37 (d, J = 6.7 Hz, 3H), 3.16 (septet, J = 6.8 Hz, 1H), 3.73 (dd, J = 9.0, 8.6 Hz, 1H), 3.98 (dd, J = 10.7, 1.7 Hz, 1H), 4.15 (dd, J = 8, 8 Hz, 1H), 4.19 (dd, J = 10.7, 4.3 Hz, 1H), 4.25 (m, 1H), 4.85 (m, 1H), 5.14 (d, J = 9.6 Hz, 1H), 6.97 (d, J = 8.8 Hz, 2H), 6.97 (m, 1H), 7.45 (d, J = 8.8 Hz, 2H), 7.90 (ddd, J = 8.5, 7.7, 2.7 Hz, 1H), 8.32 (br d, J = 2.6 Hz, 1H). LCMS m/z 380.9 (M + 1). |
| 13 | 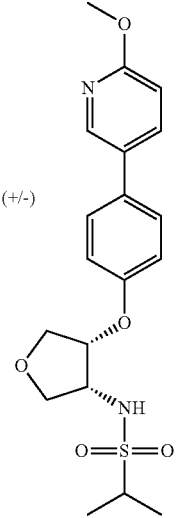 (+/−) | Ex 2 | cis-N-{4-[4-(6-methoxypyridin-3-yl)phenoxy]tetrahydrofuran-3-yl}propane-2-sulfonamide | $^1$H NMR δ 1.34 (d, J = 6.7 Hz, 3H), 1.37 (d, J = 6.8 Hz, 3H), 3.15 (septet, J = 6.8 Hz, 1H), 3.72 (dd, J = 8.9, 8.5 Hz, 1H), 3.96 (s, 3H), 3.98 (dd, assumed, partially obscured by methyl group, J = 10.8, 1.8 Hz, 1H), 4.14 (dd, J = 8, 8 Hz, 1H), 4.18 (dd, J = 10.7, 4.2 Hz, 1H), 4.24 (m, 1H), 4.82 (m, 1H), 5.03 (d, J = 9.5 Hz, 1H), 6.79 (dd, J = 8.6, 0.7 Hz, 1H), 6.94 (d, J = 8.8 Hz, 2H), 7.44 (d, J = 8.8 Hz, 2H), 7.72 (dd, J = 8.6, 2.6 Hz, 1H), 8.31 (dd, J = 2.6, 0.7 Hz, 1H). LCMS m/z 393.4 (M + 1). |

TABLE 1-continued

| Ex # | Structure | Method | IUPAC Name | ¹H NMR (400 MHz, CDCl₃), ¹³C NMR (100 MHz, CDCl₃) (unless otherwise indicated): observed peaks, δ (ppm); Mass spectrum: observed ion m/z; additional data |
|---|---|---|---|---|
| 14 | 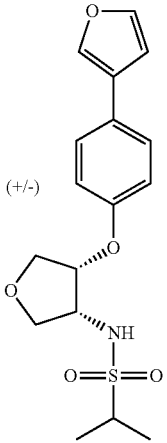 (+/−) | Ex 2 | cis-N-{4-[4-(3-furyl)phenoxy]tetrahydrofuran-3-yl}propane-2-sulfonamide | $^1$H NMR δ 1.35 (d, J = 6.7 Hz, 3H), 1.38 (d, J = 6.8 Hz, 3H), 3.15 (septet, J = 6.8 Hz, 1H), 3.72 (dd, J = 8.7, 8.7 Hz, 1H), 3.97 (dd, J = 10.7, 1.8 Hz, 1H), 4.13-4.19 (m, 2H), 4.23 (m, 1H), 4.80 (m, 1H), 4.98 (d, J = 9.3 Hz, 1H), 6.65 (dd, J = 1.9, 0.9 Hz, 1H), 6.89 (d, J = 8.8 Hz, 2H), 7.42 (d, J = 8.8 Hz, 2H), 7.47 (dd, J = 1.7, 1.7 Hz, 1H), 7.67 (dd, J = 1.5, 0.8 Hz, 1H). LCMS m/z 352.0 (M + 1). |
| 15 | 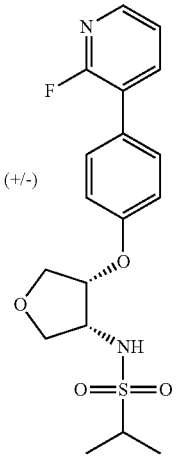 (+/−) | Ex 2 | cis-N-{4-[4-(2-fluoropyridin-3-yl)phenoxy]tetrahydrofuran-3-yl}propane-2-sulfonamide | $^1$H NMR δ 1.35 (d, J = 6.8 Hz, 3H), 1.37 (d, J = 6.8 Hz, 3H), 3.15 (septet, J = 6.8 Hz, 1H), 3.73 (dd, J = 8.7, 8.7 Hz, 1H), 3.98 (dd, J = 10.7, 1.5 Hz, 1H), 4.15 (dd, J = 7.8, 7.8 Hz, 1H), 4.20 (dd, J = 10.8, 4.2 Hz, 1H), 4.25 (m, 1H), 4.85 (m, 1H), 5.04 (m, 1H), 6.96 (d, J = 8.6 Hz, 2H), 7.26 (m, 1H), 7.51 (br d, J = 8.8 Hz, 2H), 7.83 (m, 1H), 8.16 (br d, J = 4.8 Hz, 1H). $^{13}$C NMR δ 16.53, 16.56, 54.36, 55.42, 70.21, 71.98, 75.89, 115.74, 121.82 (d, J = 4 Hz), 123.05 (d, J = 28 Hz), 127.52 (d, J = 4 Hz), 130.26, 140.23 (d, J = 4 Hz), 145.90 (d, J = 15 Hz), 156.63, 160.21 (d, J = 240 Hz). |
| 16 | 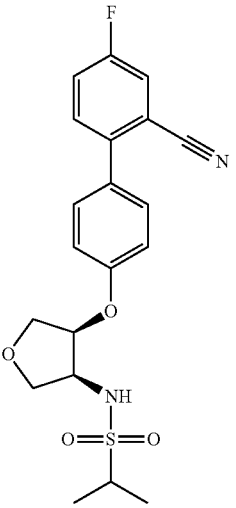 [SMILES: CC(C)S(=O)(=O)N[C@H]1COC[C@H]1Oc1ccc(-c2ccc(F)cc2C#N)cc1] | Ex 2 | N-{(3S,4S)-4-[(2'-cyano-4'-fluorobiphenyl-4-yl)oxy]tetrahydrofuran-3-yl}propane-2-sulfonamide | $^1$H NMR δ 1.38 (d, J = 6.8 Hz, 3H), 1.41 (d, J = 6.8 Hz, 3H), 3.20 (septet, J = 6.8 Hz, 1H), 3.77 (dd, J = 8.8, 8.8 Hz, 1H), 4.00 (dd, J = 10.7, 1.6 Hz, 1H), 4.17 (dd, J = 7.9, 7.9 Hz, 1H), 4.23 (dd, J = 10.7, 4.2 Hz, 1H), 4.30 (m, 1H), 4.82 (m, 1H), 5.51 (d, J = 9.4 Hz, 1H), 7.03 (d, J = 8.8 Hz, 2H), 7.39 (m, 1H), 7.46-7.51 (m, 4H). LCMS m/z 404.9 (M + 1). HPLC: Chiralpak AD-H column; 75:25 CO₂:propanol; second-eluting enantiomer. |

| Ex # | Structure | Method | IUPAC Name | ¹H NMR (400 MHz, CDCl₃), ¹³C NMR (100 MHz, CDCl₃) (unless otherwise indicated): observed peaks, δ (ppm); Mass spectrum: observed ion m/z; additional data |
|---|---|---|---|---|
| 17 | 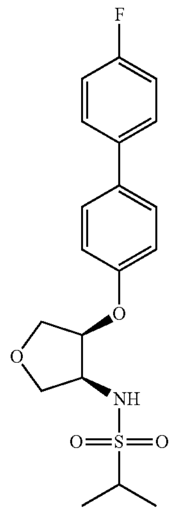 [SMILES: CC(C)S(=O)(=O)N[C@H]1COC[C@H]1Oc1ccc(-c2ccc(F)cc2)cc1] | Ex 2 | N-{(3S,4S)-4-[(4'-fluoro biphenyl-4-yl)oxy]tetra hydrofuran-3-yl}propane-2-sulfonamide | ¹H NMR δ 1.36 (d, J = 6.6 Hz, 3H), 1.39 (d, J = 6.8 Hz, 3H), 3.16 (septet, J = 6.8 Hz, 1H), 3.74 (dd, J = 8.7, 8.7 Hz, 1H), 3.99 (br d, J = 10.8 Hz, 1H), 4.18 (m, 2H), 4.25 (m, 1H), 4.83 (m, 1H), 5.10 (m, 1H), 6.94 (d, J = 8.7 Hz, 2H), 7.10 (dd, J = 8.6, 8.6 Hz, 2H), 7.46-7.49 (m, 4H). LCMS m/z 379.9 (M + 1). HPLC: Chiralcel OJ-H column; 75:25 CO₂:methanol; second-eluting enantiomer. |
| 18 | 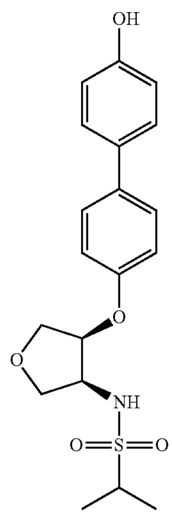 [SMILES: CC(C)S(=O)(=O)N[C@H]1COC[C@H]1Oc1ccc(-c2ccc(O)cc2)cc1] | Ex 2 | N-{(3S,4S)-4-[(4'-hydroxy biphenyl-4-yl)oxy]tetra hydrofuran-3-yl}propane-2-sulfonamide | ¹H NMR (400 MHz, CD₃OD) δ 1.26 (d, J = 6.8 Hz, 3H), 1.30 (d, J = 6.8 Hz, 3H), 3.16 (septet, J = 6.7 Hz, 1H), 3.73 (dd, J = 8.6, 8.6 Hz, 1H), 3.93 (dd, J = 10.4, 1.6 Hz, 1H), 4.08 (dd, J = 7.9, 7.9 Hz, 1H), 4.17 (dd, J = 10.4, 4.2 Hz, 1H), 4.26 (m, 1H), 4.9 (1H, assumed, obscured by water signal), 6.83 (d, J = 8.6 Hz, 2H), 7.00 (d, J = 8.7 Hz, 2H), 7.39 (d, J = 8.6 Hz, 2H), 7.47 (d, J = 8.7 Hz, 2H). LCMS m/z 376.5 (M − 1). |
| 19 | 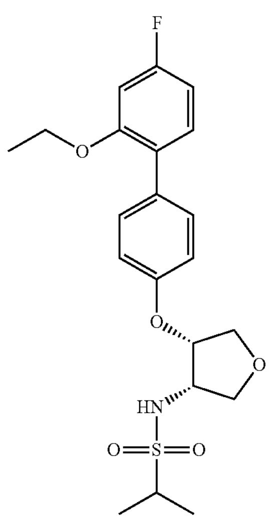 [SMILES: CCOc1cc(F)ccc1-c1ccc(O[C@@H]2COC[C@@H]2NS(=O)(=O)C(C)C)cc1] | Ex 2 | N-{(3S,4S)-4-[(2'-ethoxy-4'-fluoro biphenyl-4-yl)oxy]tetra hydrofuran-3-yl}propane-2-sulfonamide | ¹H NMR (500 MHz, CDCl₃) δ 1.36-1.40 (m, 9H), 3.17 (septet, J = 6.8 Hz, 1H), 3.75 (dd, J = 8.7, 8.7 Hz, 1H), 4.01-4.05 (m, 3H), 4.15-4.21 (m, 2H), 4.24 (m, 1H), 4.84 (m, 1H), 4.88 (d, J = 9.4 Hz, 1H), 6.68-6.73 (m, 2H), 6.91 (d, J = 8.8 Hz, 2H), 7.23 (dd, J = 8.3, 6.8 Hz, 1H), 7.46 (d, J = 8.9 Hz, 2H). LCMS m/z 424.0 (M + 1). |

… TABLE 1-continued

| Ex # | Structure | Method | IUPAC Name | ¹H NMR (400 MHz, CDCl₃), ¹³C NMR (100 MHz, CDCl₃) (unless otherwise indicated): observed peaks, δ (ppm); Mass spectrum: observed ion m/z; additional data |
|---|---|---|---|---|
| 20 | 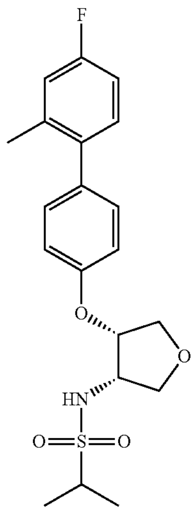 [SMILES: Cc1cc(F)ccc1-c1ccc(O[C@@H]2COC[C@@H]2NS(=O)(=O)C(C)C)cc1] | Ex 2 | N-{(3S,4S)-4-[(4'-fluoro-2'-methyl biphenyl-4-yl)oxy]tetrahydrofuran-3-yl}propane-2-sulfonamide | $^1$H NMR (500 MHz, CDCl₃) δ 1.37 (d, J = 6.7 Hz, 3H), 1.40 (d, J = 6.8 Hz, 3H), 2.25 (s, 3H), 3.18 (septet, J = 6.8 Hz, 1H), 3.75 (dd, J = 8.7, 8.7 Hz, 1H), 4.03 (dd, J = 10.6, 1.8 Hz, 1H), 4.17 (dd, J = 7.9, 7.9 Hz, 1H), 4.21 (dd, J = 10.6, 4.4 Hz, 1H), 4.25 (m, 1H), 4.85 (m, 1H), 4.94 (d, J = 9.5 Hz, 1H), 6.90-6.94 (m, 3H), 6.97 (dd, J = 9.8, 2.7 Hz, 1H), 7.14 (dd, J = 8.4, 6.0 Hz, 1H), 7.22 (d, J = 8.8 Hz, 2H). LCMS m/z 394.1 (M + 1). |
| 21 | 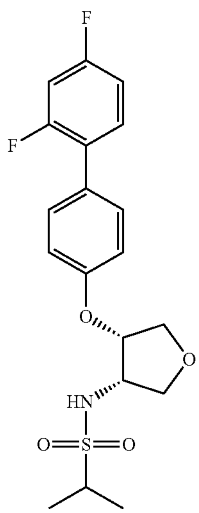 [SMILES: CC(C)S(=O)(=O)N[C@H]1COC[C@H]1Oc1ccc(-c2ccc(F)cc2F)cc1] | Ex 2 | N-{(3S,4S)-4-[(2',4'-difluoro biphenyl-4-yl)oxy]tetrahydrofuran-3-yl}propane-2-sulfonamide | $^1$H NMR (500 MHz, CDCl₃) δ 1.36 (d, J = 6.8 Hz, 3H), 1.39 (d, J = 6.8 Hz, 3H), 3.16 (septet, J = 6.8 Hz, 1H), 3.74 (dd, J = 8.7, 8.7 Hz, 1H), 4.00 (dd, J = 10.7, 1.8 Hz, 1H), 4.15-4.22 (m, 2H), 4.25 (m, 1H), 4.84 (m, 1H), 4.97 (d, J = 9.5 Hz, 1H), 6.88-6.97 (m, 4H), 7.36 (ddd, J = 8.7, 8.7, 6.4 Hz, 1H), 7.44 (dd, J = 8.8, 1.6 Hz, 2H). LCMS m/z 398.5 (M + 1). |
| 22 | 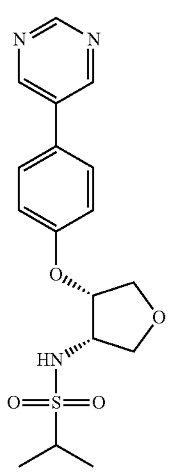 [SMILES: CC(C)S(=O)(=O)N[C@H]1COC[C@H]1Oc1ccc(-c2cncnc2)cc1] | Ex 2 | N-[(3S,4S)-4-(4-pyrimidin-5-ylphenoxy)tetrahydrofuran-3-yl]propane-2-sulfonamide | $^1$H NMR (500 MHz, CDCl₃) δ 1.37 (d, J = 6.8 Hz, 3H), 1.40 (d, J = 6.8 Hz, 3H), 3.19 (septet, J = 6.8 Hz, 1H), 3.79 (dd, J = 8.8, 8.8 Hz, 1H), 4.01 (dd, J = 10.7, 1.5 Hz, 1H), 4.19 (dd, J = 7.9, 7.9 Hz, 1H), 4.23 (dd, J = 10.7, 4.3 Hz, 1H), 4.32 (m, 1H), 4.91 (m, 1H), 5.88 (d, J = 9.6 Hz, 1H), 7.03 (d, J = 8.8 Hz, 2H), 7.51 (d, J = 8.8 Hz, 2H), 8.88 (s, 2H), 9.16 (s, 1H). LCMS m/z 364.5 (M + 1). |

| Ex # | Structure | IUPAC Method Name | ¹H NMR (400 MHz, CDCl₃), ¹³C NMR (100 MHz, CDCl₃) (unless otherwise indicated): observed peaks, δ (ppm); Mass spectrum: observed ion m/z; additional data |
|---|---|---|---|
| 23 | 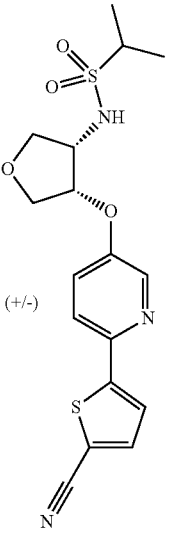 [SMILES: CC(C)S(=O)(=O)N[C@H]1COC[C@H]1Oc1ccc(-c2ccc(C#N)s2)nc1] (+/−) | Ex 2 cis-N-[4-{[6-(5-cyano-2-thienyl)pyridin-3-yl]oxy}tetrahydrofuran-3-yl]propane-2-sulfonamide | ¹H NMR (500 MHz, CDCl₃) δ 1.36-1.39 (m, 6H), 3.18 (septet, J = 6.8 Hz, 1H), 3.71 (dd, J = 9.2, 8.7 Hz, 1H), 3.98 (dd, J = 10.9, 1.6 Hz, 1H), 4.16 (dd, J = 8, 8 Hz, 1H), 4.20 (dd, J = 10.9, 4.2 Hz, 1H), 4.27 (m, 1H), 4.88 (m, 1H), 4.92 (d, J = 10.0 Hz, 1H), 7.29 (dd, J = 8.7, 2.9 Hz, 1H), 7.38 (d, J = 4.0 Hz, 1H), 7.57 (d, J = 4.0 Hz, 1H), 7.63 (dd, J = 8.8, 0.6 Hz, 1H), 8.25 (dd, J = 2.9, 0.5 Hz, 1H). LCMS m/z 394.0 (M + 1). |
| 24 | 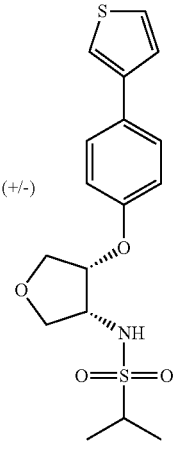 [SMILES: CC(C)S(=O)(=O)N[C@@H]1COC[C@@H]1Oc1ccc(-c2ccsc2)cc1] (+/−) | Ex 2 cis-N-{4-[4-(3-thienyl)phenoxy]tetrahydrofuran-3-yl}propane-2-sulfonamide | ¹H NMR δ 1.36 (d, J = 6.8 Hz, 3H), 1.39 (d, J = 6.8 Hz, 3H), 3.16 (septet, J = 6.8 Hz, 1H), 3.73 (dd, J = 8.6, 8.6 Hz, 1H), 3.99 (dd, J = 10.6, 1.6 Hz, 1H), 4.14-4.20 (m, 2H), 4.24 (m, 1H), 4.82 (m, 1H), 4.99 (d, J = 9.4 Hz, 1H), 6.91 (d, J = 8.8 Hz, 2H), 7.33-7.39 (m, 3H), 7.54 (d, J = 8.8 Hz, 2H). LCMS m/z 368.0 (M + 1). |
| 25 | 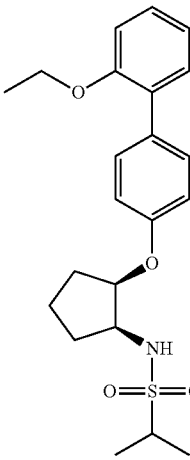 | Ex 6 N-{(1S,2R)-2-[(2'-ethoxybiphenyl-4-yl)oxy]cyclopentyl}propane-2-sulfonamide | ¹H NMR (500 MHz, CDCl₃) δ 1.36 (d, J = 7 Hz, 3H), 1.37 (t, J = 7.1 Hz, 3H), 1.40 (d, J = 6.8 Hz, 3H), 1.65 (m, 1H), 1.83-1.93 (m, 2H), 1.96-2.00 (m, 2H), 2.14 (m, 1H), 3.15 (septet, J = 6.8 Hz, 1H), 3.89 (m, 1H), 4.05 (q, J = 7.0 Hz, 2H), 4.68 (m, 1H), 4.73 (d, J = 9.3 Hz, 1H), 6.92 (d, J = 8.8 Hz, 2H), 6.97 (br d, J = 8.2 Hz, 1H), 7.01 (ddd, J = 7.4, 7.4, 1.1 Hz, 1H), 7.28 (ddd, J = 8.2, 7.4, 1.8 Hz, 1H), 7.32 (dd, J = 7.5, 1.7 Hz, 1H), 7.51 (d, J = 8.9 Hz, 2H). MS (APCl) m/z 404.3 (M + 1). |

TABLE 1-continued

| Ex # | Structure | IUPAC Method Name | ¹H NMR (400 MHz, CDCl₃), ¹³C NMR (100 MHz, CDCl₃) (unless otherwise indicated): observed peaks, δ (ppm); Mass spectrum: observed ion m/z; additional data |
|---|---|---|---|
| 26 | 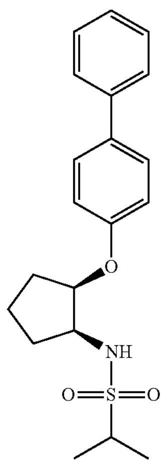 [SMILES: CC(C)S(=O)(=O)N[C@H]1CCC[C@H]1Oc1ccc(-c2ccccc2)cc1] | Ex 6 N-[(1S,2R)-2-(biphenyl-4-yloxy)cyclopentyl]propane-2-sulfonamide | ¹H NMR (500 MHz, CDCl₃) δ 1.36 (d, J = 6.8 Hz, 3H), 1.40 (d, J = 6.8 Hz, 3H), 1.65 (m, 1H), 1.84-1.91 (m, 2H), 1.94-2.00 (m, 2H), 2.15 (m, 1H), 3.15 (septet, J = 6.8 Hz, 1H), 3.89 (m, 1H), 4.68 (ddd, J = 4.5, 4.5, 2.2 Hz, 1H), 4.72 (d, J = 9.3 Hz, 1H), 6.97 (d, J = 8.7 Hz, 2H), 7.32 (m, 1H), 7.43 (m, 2H), 7.54 (d, J = 8.7 Hz, 2H), 7.56 (m, 2H). LCMS m/z 360.1 (M + 1). |
| 27 | 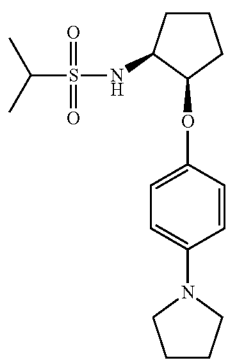 [SMILES: CC(C)S(=O)(=O)N[C@H]1CCC[C@H]1Oc1ccc(N2CCCC2)cc1] | C N-[(1S,2R)-2-(4-pyrrolidin-1-ylphenoxy)cyclopentyl]propane-2-sulfonamide | ¹H NMR (500 MHz, CDCl₃) δ 1.36 (d, J = 6.8 Hz, 3H), 1.39 (d, J = 6.8 Hz, 3H), 1.60 (m, 1H), 1.79-1.91 (m, 4H), 2.00 (m, 4H), 2.09 (m, 1H), 3.15 (septet, J = 6.8 Hz, 1H), 3.24 (m, 4H), 3.83 (m, 1H), 4.48 (m, 1H), 4.82 (d, J = 9.2 Hz, 1H), 6.52 (d, J = 8.9 Hz, 2H), 6.82 (d, J = 9.0 Hz, 2H). LCMS m/z 353 (M + 1). |
| 28 | | Ex 6 D | 2-cyano-4'-({(1R,2S)-2-[(isopropylsulfonyl)amino]cyclopentyl}oxy)biphenyl-4-carboxylic acid | ¹H NMR (500 MHz, CDCl₃) δ 1.38 (d, J = 6.8 Hz, 3H), 1.41 (d, J = 6.8 Hz, 3H), 1.68 (m, 1H), 1.84-1.92 (m, 2H), 1.94-2.05 (m, 2H), 2.16 (m, 1H), 3.17 (septet, J = 6.8 Hz, 1H), 3.92 (m, 1H), 4.73 (m, 1H), 4.80 (d, J = 9.5 Hz, 1H), 7.04 (d, J = 8.8 Hz, 2H), 7.56 (d, J = 8.8 Hz, 2H), 7.62 (d, J = 8.2 Hz, 1H), 8.30 (dd, J = 8.2, 1.8 Hz, 1H), 8.48 (d, J = 1.7 Hz, 1H). LCMS m/z 429.1 (M + 1). |

TABLE 1-continued

| Ex # | Structure | Method | IUPAC Name | ¹H NMR (400 MHz, CDCl₃), ¹³C NMR (100 MHz, CDCl₃) (unless otherwise indicated): observed peaks, δ (ppm); Mass spectrum: observed ion m/z; additional data |
|---|---|---|---|---|
| 29 | 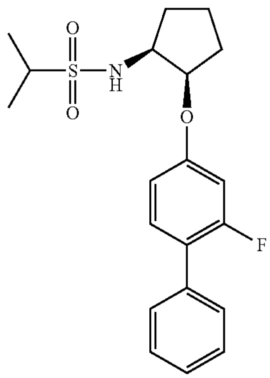 [SMILES: CC(C)S(=O)(=O)N[C@H]1CCC[C@H]1Oc1ccc(-c2ccccc2)c(F)c1] | B | N-{(1S,2R)-2-[(2-fluoro biphenyl-4-yl)oxy]cyclo pentyl} propane-2-sulfonamide | ¹H NMR δ 1.37 (d, J = 6.7 Hz, 3H), 1.40 (d, J = 6.7 Hz, 3H), 1.67 (m, 1H), 1.81-2.05 (m, 4H), 2.14 (m, 1H), 3.15 (m, J = 6.8 Hz, 1H), 3.89 (m, 1H), 4.65 (m, 1H), 4.69 (d, J = 9.6 Hz, 1H), 6.72 (dd, J = 12.3, 2.5 Hz, 1H), 6.77 (dd, J = 8.7, 2.6 Hz, 1H), 7.33-7.39 (m, 2H), 7.42-7.46 (m, 2H), 7.50-7.53 (m, 2H). LCMS m/z 378.6 (M + 1). |
| 30 | 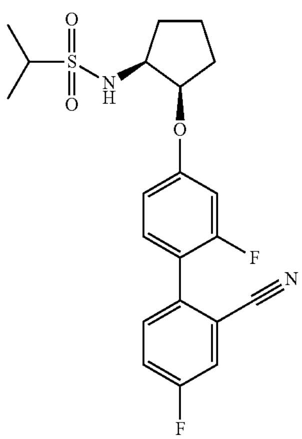 [SMILES: CC(C)S(=O)(=O)N[C@H]1CCC[C@H]1Oc1ccc(-c2ccc(F)cc2C#N)c(F)c1] | Ex 2 | N-{(1S,2R)-2-[(2'-cyano-2,4'-difluoro biphenyl-4-yl)oxy]cyclo pentyl}propane-2-sulfonamide | ¹H NMR δ 1.37 (d, J = 6.8 Hz, 3H), 1.40 (d, J = 6.8 Hz, 3H), 1.63-1.72 (m, 1H), 1.80-2.07 (m, 4H), 2.15 (m, 1H), 3.16 (septet, J = 6.8 Hz, 1H), 3.89 (m, 1H), 4.63-4.68 (m, 2H), 6.76 (dd, J = 11.7, 2.5 Hz, 1H), 6.81 (br dd, J = 8.5, 2.5 Hz, 1H), 7.32 (dd, J = 8.6, 8.6 Hz, 1H), 7.37 (ddd, J = 8.8, 8.0, 2.6 Hz, 1H), 7.45-7.49 (m, 2H). LCMS m/z 418.7 (M − 1). |
| 31 | 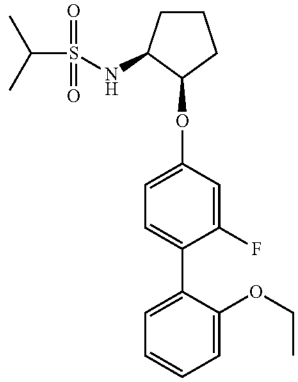 [SMILES: CCOc1ccccc1-c1ccc(O[C@@H]2CCC[C@@H]2NS(=O)(=O)C(C)C)cc1F] | B | N-{(1S,2R)-2-[(2'-ethoxy-2-fluoro biphenyl-4-yl)oxy] cyclopentyl} propane-2-sulfonamide | ¹H NMR δ 1.33 (t, J = 7.0 Hz, 3H), 1.37 (d, J = 6.7 Hz, 3H), 1.40 (d, J = 6.8 Hz, 3H), 1.62-1.71 (m, 1H), 1.81-1.92 (m, 2H), 1.95-2.01 (m, 2H), 2.14 (m, 1H), 3.15 (septet, J = 6.8 Hz, 1H), 3.89 (m, 1H), 4.06 (q, J = 7.0 Hz, 2H), 4.64-4.68 (m, 2H), 6.68 (dd, J = 11.5, 2.5 Hz, 1H), 6.73 (br dd, J = 8.4, 2.5 Hz, 1H), 6.96-7.03 (m, 2H), 7.26 (m, 1H), 7.29 (dd, J = 8.4, 8.4 Hz, 1H), 7.33 (ddd, J = 8.2, 7.5, 1.8 Hz, 1H). LCMS m/z 422 (M + 1). |

TABLE 1-continued

| Ex # | Structure | Method | IUPAC Name | ¹H NMR (400 MHz, CDCl₃), ¹³C NMR (100 MHz, CDCl₃) (unless otherwise indicated): observed peaks, δ (ppm); Mass spectrum: observed ion m/z; additional data |
|---|---|---|---|---|
| 32 | 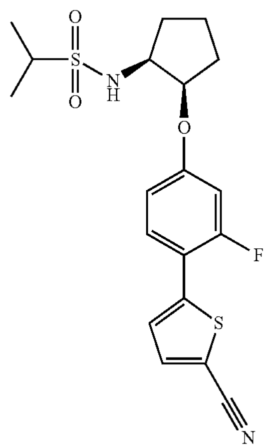 [SMILES: CC(C)S(=O)(=O)N[C@H]1CCC[C@H]1Oc1ccc(-c2ccc(C#N)s2)c(F)c1] | Ex 6 | N-{(1S,2R)-2-[4-(5-cyano-2-thienyl)-3-fluoro phenoxy]cyclopentyl}propane-2-sulfonamide | $^1$H NMR δ 1.37 (d, J = 6.8 Hz, 3H), 1.40 (d, J = 6.8 Hz, 3H), 1.64-1.72 (m, 1H), 1.80-1.95 (m, 3H), 1.97-2.04 (m, 1H), 2.14 (m, 1H), 3.15 (septet, J = 6.8 Hz, 1H), 3.89 (m, 1H), 4.57 (d, J = 9.6 Hz, 1H), 4.67 (m, 1H), 6.72-6.79 (m, 2H), 7.34 (dd, J = 4.0, 0.9 Hz, 1H), 7.54 (dd, J = 8.7, 8.7 Hz, 1H), 7.60 (dd, J = 4.0, 1.0 Hz, 1H). LCMS m/z 407 (M − 1). |
| 33 | 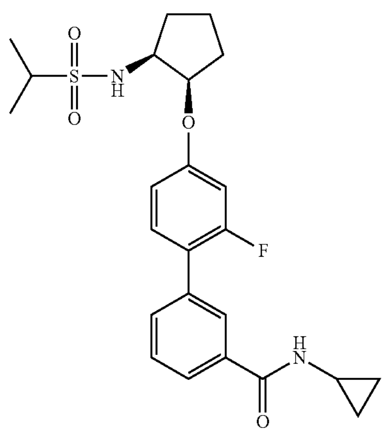 [SMILES: CC(C)S(=O)(=O)N[C@H]1CCC[C@H]1Oc1ccc(-c2cccc(C(=O)NC3CC3)c2)c(F)c1] | B | N-cyclopropyl-2'-fluoro-4'-({(1R,2S)-2-[(isopropyl sulfonyl)amino]cyclopentyl}oxy)biphenyl-3-carboxamide | $^1$H NMR δ 0.65 (m, 2H), 0.89 (m, 2H), 1.37 (d, J = 6.8 Hz, 3H), 1.40 (d, J = 6.8 Hz, 3H), 1.62-1.71 (m, 1H), 1.81-2.04 (m, 4H), 2.14 (m, 1H), 2.93 (m, 1H), 3.15 (septet, J = 6.8 Hz, 1H), 3.89 (m, 1H), 4.63-4.67 (m, 2H), 6.30 (br s, 1H), 6.72 (dd, J = 12.2, 2.5 Hz, 1H), 6.78 (br dd, J = 8.6, 2.5 Hz, 1H), 7.37 (dd, J = 8.8, 8.8 Hz, 1H), 7.48 (br dd, J = 7.8, 7.8 Hz, 1H), 7.63 (m, 1H), 7.70 (ddd, J = 7.7, 1.8, 1.2 Hz, 1H), 7.85 (m, 1H). LCMS m/z 461 (M + 1). |
| 34 | 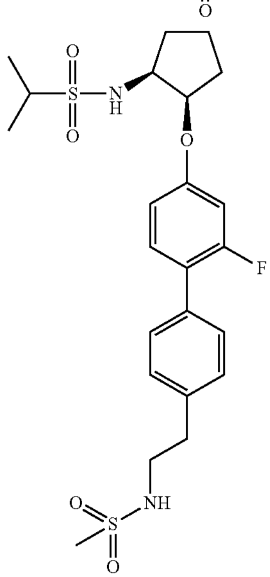 | Ex 2 | N-{(1S,2R)-2-[(2-fluoro-4'-{2-[(methylsulfonyl)amino]ethyl}biphenyl-4-yl)oxy]cyclopentyl}propane-2-sulfonamide | $^1$H NMR δ 1.37 (d, J = 6.8 Hz, 3H), 1.40 (d, J = 6.8 Hz, 3H), 1.63-1.71 (m, 1H), 1.82-2.04 (m, 4H), 2.14 (m, 1H), 2.88 (s, 3H), 2.93 (t, J = 6.7 Hz, 2H), 3.16 (septet, J = 6.8 Hz, 1H), 3.46 (dt, J = 6.6, 6.6 Hz, 2H), 3.89 (m, 1H), 4.25 (br t, J = 6.5 Hz, 1H), 4.64-4.67 (m, 2H), 6.71 (dd, J = 12.2, 2.5 Hz, 1H), 6.77 (br dd, J = 8.6, 2.6 Hz, 1H), 7.28 (d, J = 8.4 Hz, 2H), 7.34 (dd, J = 8.8, 8.8 Hz, 1H), 7.48 (dd, J = 8.2, 1.6 Hz, 2H). LCMS m/z 499.0 (M + 1). |

TABLE 1-continued

| Ex # | Structure | Method | IUPAC Name | ¹H NMR (400 MHz, CDCl₃), ¹³C NMR (100 MHz, CDCl₃) (unless otherwise indicated): observed peaks, δ (ppm); Mass spectrum: observed ion m/z; additional data |
|---|---|---|---|---|
| 35 | 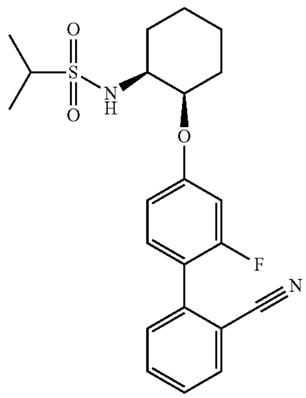 [SMILES: CC(C)S(=O)(=O)N[C@H]1CCCC[C@H]1Oc1ccc(-c2ccccc2C#N)c(F)c1] | Ex 2 | N-{(1S,2R)-2-[(2'-cyano-2-fluoro biphenyl-4-yl)oxy]cyclohexyl} propane-2-sulfonamide | ¹H NMR δ 1.36-1.40 (m, 6H), 1.4-1.56 (m, 4H), 1.80-1.91 (m, 3H), 2.16 (m, 1H), 3.14 (septet, J = 6.8 Hz, 1H), 3.58 (m, 1H), 4.49 (d, J = 9.5 Hz, 1H), 4.64 (m, 1H), 6.81 (dd, J = 11.7, 2.4 Hz, 1H), 6.86 (dd, J = 8.5, 2.4 Hz, 1H), 7.36 (dd, J = 8.6, 8.6 Hz, 1H), 7.44-7.50 (m, 2H), 7.65 (ddd, J = 7.7, 7.7, 1.4 Hz, 1H), 7.77 (br d, J = 7.8 Hz, 1H). LCMS m/z 415.3 (M − 1). |
| 36 | 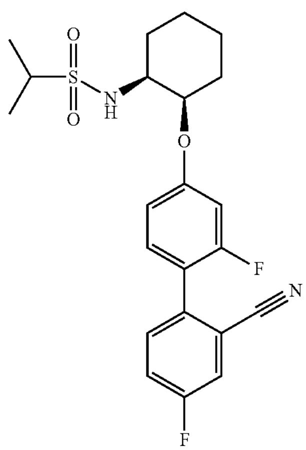 [SMILES: CC(C)S(=O)(=O)N[C@H]1CCCC[C@H]1Oc1ccc(-c2ccc(F)cc2C#N)c(F)c1] | Ex 2 | N-{(1S,2R)-2-[(2'-cyano-2,4'-difluoro biphenyl-4-yl)oxy] cyclohexyl} propane-2-sulfonamide | ¹H NMR δ 1.35-1.38 (m, 6H), 1.4-1.53 (m, 4H), 1.79-1.90 (m, 3H), 2.14 (m, 1H), 3.13 (septet, J = 6.8 Hz, 1H), 3.57 (m, 1H), 4.54 (d, J = 9.5 Hz, 1H), 4.63 (m, 1H), 6.80 (dd, J = 11.7, 2.4 Hz, 1H), 6.85 (dd, J = 8.5, 2.4 Hz, 1H), 7.31 (dd, J = 8.5, 8.5 Hz, 1H), 7.36 (m, 1H), 7.44-7.48 (m, 2H). LCMS m/z 433 (M − 1). |
| 37 | 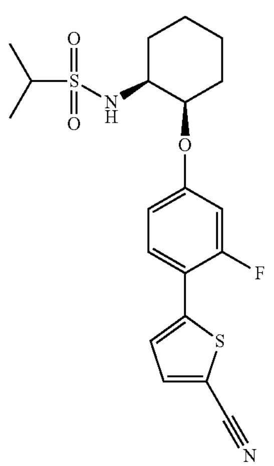 [SMILES: CC(C)S(=O)(=O)N[C@H]1CCCC[C@H]1Oc1ccc(-c2ccc(C#N)s2)c(F)c1] | Ex 2 | N-{(1S,2R)-2-[4-(5-cyano-2-thienyl)-3-fluoro phenoxy] cyclohexyl} propane-2-sulfonamide | ¹H NMR δ 1.37 (d, J = 6.7 Hz, 3H), 1.38 (d, J = 6.8 Hz, 3H), 1.4-1.58 (m, 4H), 1.80-1.90 (m, 3H), 2.12 (m, 1H), 3.13 (septet, J = 6.8 Hz, 1H), 3.57 (m, 1H), 4.42 (d, J = 9.5 Hz, 1H), 4.65 (m, 1H), 6.77-6.84 (m, 2H), 7.34 (dd, J = 4.0, 0.9 Hz, 1H), 7.54 (dd, J = 8.7, 8.7 Hz, 1H), 7.60 (dd, J = 4.0, 1.0 Hz, 1H). LCMS m/z 423.5 (M + 1). |

TABLE 1-continued

| Ex # | Structure | Method | IUPAC Name | ¹H NMR (400 MHz, CDCl₃), ¹³C NMR (100 MHz, CDCl₃) (unless otherwise indicated): observed peaks, δ (ppm); Mass spectrum: observed ion m/z; additional data |
|---|---|---|---|---|
| 38 | 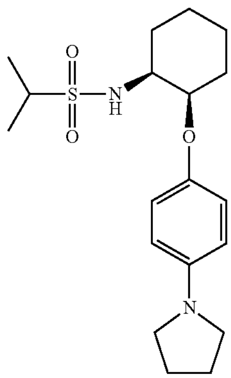 [SMILES: CC(C)S(=O)(=O)N[C@H]1CCCC[C@H]1Oc1ccc(N2CCCC2)cc1] | C | N-[(1S,2R)-2-(4-pyrrolidin-1-ylphenoxy)cyclohexyl]propane-2-sulfonamide | ¹H NMR δ 1.36 (m, 2H, assumed, obscured by methyl groups), 1.38 (d, J = 6.8 Hz, 3H), 1.39 (d, J = 6.8 Hz, 3H), 1.51-1.63 (m, 2H), 1.76-1.90 (m, 3H), 2.00 (m, 4H), 2.03 (m, 1H, assumed, obscured by pyrrolidine signal), 3.14 (septet, J = 6.8 Hz, 1H), 3.25 (m, 4H), 3.52 (m, 1H), 4.34 (m, 1H), 4.68 (d, J = 9.2 Hz, 1H), 6.52 (br d, J = 8.8 Hz, 2H), 6.89 (d, J = 9.0 Hz, 2H). LCMS m/z 366.7 (M + 1). |
| 39 | 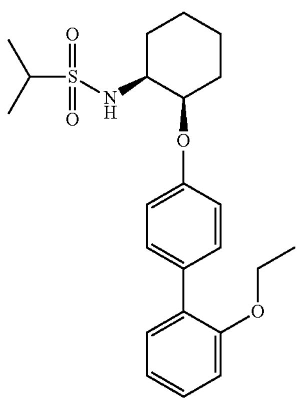 [SMILES: CCOc1ccccc1-c1ccc(O[C@@H]2CCCC[C@@H]2NS(=O)(=O)C(C)C)cc1] | Ex 2 | N-{(1S,2R)-2-[(2'-ethoxybiphenyl-4-yl)oxy]cyclohexyl}propane-2-sulfonamide | ¹H NMR δ 1.36-1.39 (m, 9H), 1.36-1.58 (m, 4H, assumed, obscured by methyl groups), 1.78-1.98 (m, 3H), 2.16 (m, 1H), 3.14 (septet, J = 6.8 Hz, 1H), 3.58 (m, 1H), 4.05 (q, J = 7.0 Hz, 2H), 4.58 (d, J = 9.3 Hz, 1H), 4.61 (m, 1H), 6.94-7.03 (m, 4H), 7.28 (ddd, J = 8.2, 7.5, 1.8 Hz, 1H), 7.32 (dd, J = 7.5, 1.7 Hz, 1H), 7.52 (d, J = 8.9 Hz, 2H). LCMS m/z 415.6 (M − 1). |
| 40 | 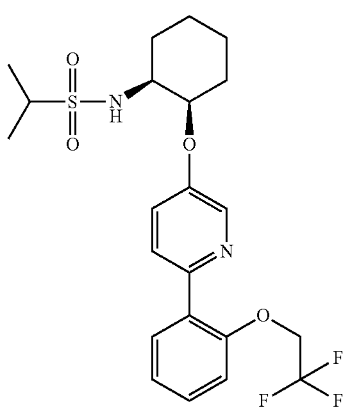 [SMILES: CC(C)S(=O)(=O)N[C@H]1CCCC[C@H]1Oc1ccc(-c2ccccc2OCC(F)(F)F)nc1] | B | N-[(1S,2R)-2-({6-[2-(2,2,2-trifluoroethoxy)phenyl]pyridin-3-yl}oxy)cyclohexyl]propane-2-sulfonamide | ¹H NMR δ 1.36-1.39 (m, 6H), 1.4-1.57 (m, 4H, assumed, partially obscured by methyl signals), 1.81-1.97 (m, 3H), 2.10-2.18 (m, 1H), 3.14 (septet, J = 6.8 Hz, 1H), 3.60 (m, 1H), 4.36 (q, J = 8.2 Hz, 2H), 4.53 (d, J = 9.5 Hz, 1H), 4.67 (m, 1H), 6.97 (br d, J = 8.2 Hz, 1H), 7.19 (ddd, J = 7.5, 7.5, 1.1 Hz, 1H), 7.32 (dd, J = 8.8, 3.0 Hz, 1H), 7.36 (ddd, J = 8.2, 7.4, 1.8 Hz, 1H), 7.79 (dd, J = 8.8, 0.6 Hz, 1H), 7.84 (dd, J = 7.7, 1.7 Hz, 1H), 8.42 (dd, J = 3.0, 0.6 Hz, 1H). LCMS m/z 470.7 (M − 1). |

| Ex # | Structure | Method | IUPAC Name | ¹H NMR (400 MHz, CDCl₃), ¹³C NMR (100 MHz, CDCl₃) (unless otherwise indicated): observed peaks, δ (ppm); Mass spectrum: observed ion m/z; additional data |
|---|---|---|---|---|
| 41 | 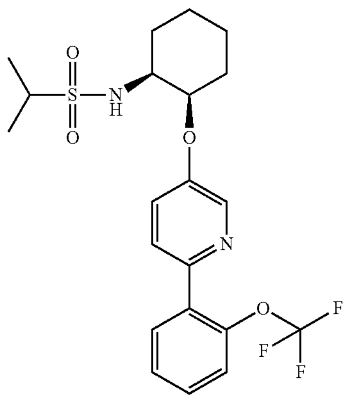 [SMILES: CC(C)S(=O)(=O)N[C@H]1CCCC[C@H]1Oc1ccc(-c2ccccc2OC(F)(F)F)nc1] | B | N-[(1S,2R)-2-({6-[2-(trifluoro methoxy) phenyl] pyridin-3-yl}oxy) cyclohexyl] propane-2-sulfonamide | ¹H NMR δ 1.37 (d, J = 6.7 Hz, 3H), 1.38 (d, J = 6.8 Hz, 3H), 1.4-1.58 (m, 4H, assumed, partially obscured by methyl signals), 1.81-1.97 (m, 3H), 2.11-2.17 (m, 1H), 3.14 (septet, J = 6.8 Hz, 1H), 3.60 (m, 1H), 4.53 (d, J = 9.5 Hz, 1H), 4.69 (m, 1H), 7.33-7.36 (m, 2H), 7.38-7.43 (m, 2H), 7.64 (dd, J = 8.7, 0.6 Hz, 1H), 7.82 (m, 1H), 8.44 (dd, J = 3.0, 0.6 Hz, 1H). LCMS m/z 459 (M + 1). |
| 42 | 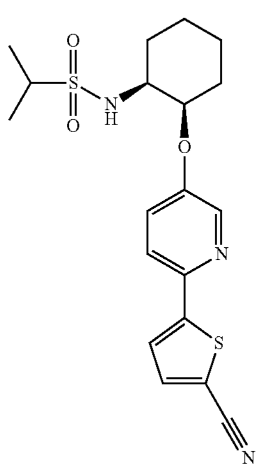 [SMILES: CC(C)S(=O)(=O)N[C@H]1CCCC[C@H]1Oc1ccc(-c2ccc(C#N)s2)nc1] | Ex 2 | N-[(1S,2R)-2-{[6-(5-cyano-2-thienyl pyridin)-3-yl]oxy} cyclohexyl] propane-2-sulfonamide | ¹H NMR δ 1.38 (d, J = 6.8 Hz, 3H), 1.39 (d, J = 6.8 Hz, 3H), 1.43-1.56 (m, 4H, assumed, partially obscured by water signal), 1.82-1.90 (m, 3H), 2.06-2.12 (m, 1H), 3.15 (septet, J = 6.8 Hz, 1H), 3.58 (m, 1H), 4.44 (d, J = 9.5 Hz, 1H), 4.70 (m, 1H), 7.35 (dd, J = 8.8, 2.9 Hz, 1H), 7.39 (d, J = 4.0 Hz, 1H), 7.59 (d, J = 4.0 Hz, 1H), 7.65 (dd, J = 8.7, 0.6 Hz, 1H), 8.31 (dd, J = 2.9, 0.6 Hz, 1H). LCMS m/z 406 (M + 1). |

TABLE 2

| Ex # | Method | Structure | IUPAC Name | Ret. Time (min.) | Mol. Wt. Calc. | Mass spec: Obs ion m/z (M + 1) |
|---|---|---|---|---|---|---|
| 43 | E | 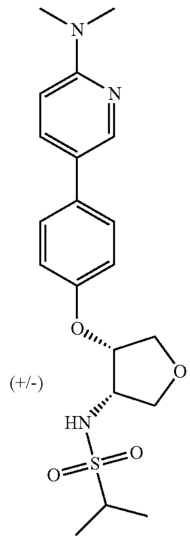 | cis-N-[4-{4-[6-(dimethyl-amino)-pyridin-3-yl]phenoxy}-tetrahydrofuran-3-yl]propane-2-sulfonamide | 1.66$^A$ | 405.17 | 406.07 |
| 44 | E | 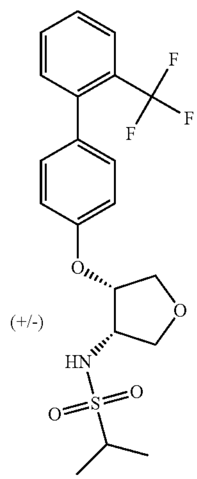 [SMILES: CC(C)S(=O)(=O)N[C@H]1COC[C@H]1Oc1ccc(-c2ccccc2C(F)(F)F)cc1] | cis-N-[4-{[2'-(trifluoro-methyl)-biphenyl-4-yl]oxy}-tetrahydrofuran-3-yl]propane-2-sulfonamide | 3.43$^A$ | 429.12 | 430.03 |
| 45 | E | 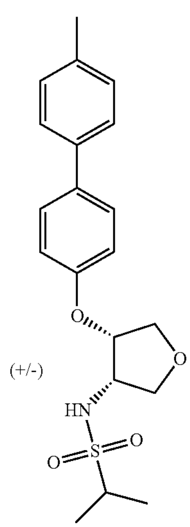 | cis-N-{4-[(4'-methylbiphenyl-4-yl)oxy]-tetrahydrofuran-3-yl}propane-2-sulfonamide | 3.43$^A$ | 375.15 | 376.05 |

TABLE 2-continued

| Ex # | Method | Structure | IUPAC Name | Ret. Time (min.) | Mol. Wt. Calc. | Mass spec: Obs ion m/z (M + 1) |
|---|---|---|---|---|---|---|
| 46 | E | 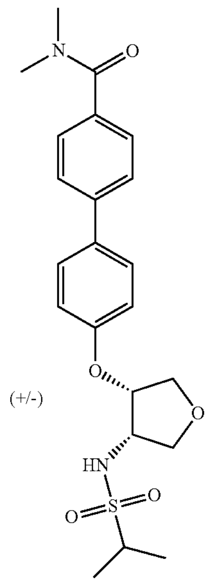 [SMILES: CC(C)S(=O)(=O)N[C@H]1COC[C@H]1Oc1ccc(-c2ccc(C(=O)N(C)C)cc2)cc1] | cis-4'-({4-[(isopropyl-sulfonyl)-amino]tetrahydrofuran-3-yl}oxy)-N,N-dimethyl-biphenyl-4-carboxamide | 2.46[A] | 432.17 | 433.08 |
| 47 | E | 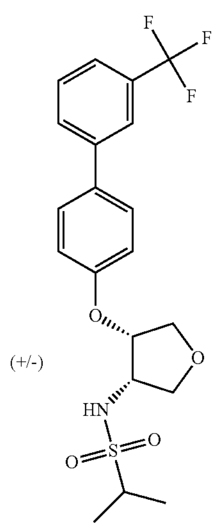 [SMILES: CC(C)S(=O)(=O)N[C@H]1COC[C@H]1Oc1ccc(-c2cccc(C(F)(F)F)c2)cc1] | cis-N-[4-{[3'-(trifluoromethyl)biphenyl-4-yl]oxy}tetrahydrofuran-3-yl]propane-2-sulfonamide | 3.53[A] | 429.12 | 430.06 |

TABLE 2-continued
| Ex # | Method | Structure | IUPAC Name | Ret. Time (min.) | Mol. Wt. Calc. | Mass spec: Obs ion m/z (M + 1) |
|---|---|---|---|---|---|---|
| 48 | E | 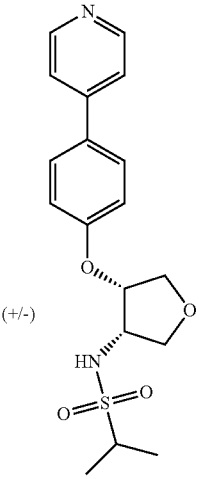 [SMILES: CC(C)S(=O)(=O)N[C@H]1COC[C@H]1Oc1ccc(-c2ccncc2)cc1] | cis-N-[4-(4-pyridin-4-ylphenoxy)tetrahydrofuran-3-yl]propane-2-sulfonamide | 1.47[A] | 362.13 | 363.06 |
| 49 | E | 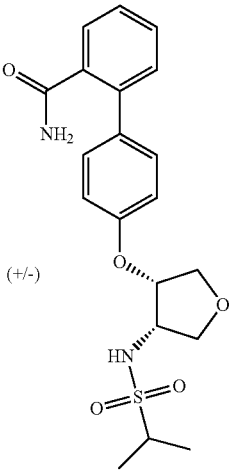 [SMILES: CC(C)S(=O)(=O)N[C@H]1COC[C@H]1Oc1ccc(-c2ccccc2C(N)=O)cc1] | cis-4'-({4-[(isopropylsulfonyl)amino]tetrahydrofuran-3-yl}oxy)biphenyl-2-carboxamide | 2.20[A] | 404.14 | 405.04 |
| 50 | E | 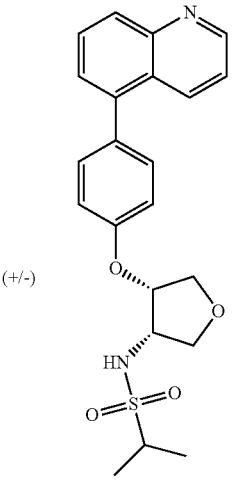 [SMILES: CC(C)S(=O)(=O)N[C@H]1COC[C@H]1Oc1ccc(-c2cccc3ncccc23)cc1] | cis-N-[4-(4-quinolin-5-ylphenoxy)tetrahydrofuran-3-yl]propane-2-sulfonamide | 1.79[A] | 412.15 | 413.05 |

TABLE 2-continued

| Ex # | Method | Structure | IUPAC Name | Ret. Time (min.) | Mol. Wt. Calc. | Mass spec: Obs ion m/z (M + 1) |
|---|---|---|---|---|---|---|
| 51 | E | 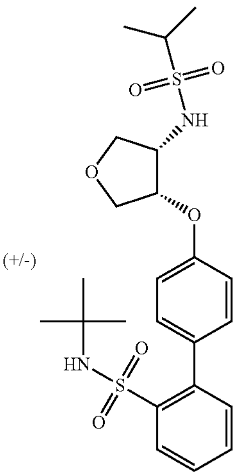 [SMILES: CC(C)S(=O)(=O)N[C@H]1COC[C@H]1Oc1ccc(-c2ccccc2S(=O)(=O)NC(C)(C)C)cc1] | cis-N-tert-butyl-4'-({4-[(isopropylsulfonyl)amino]tetrahydrofuran-3-yl}oxy)biphenyl-2-sulfonamide | 3.25[A] | 496.17 | 497.07 |
| 52 | E | 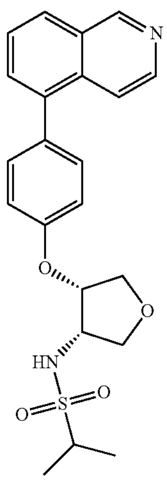 | cis-N-[4-(4-isoquinolin-5-ylphenoxy)tetrahydrofuran-3-yl]propane-2-sulfonamide | 1.78[A] | 412.15 | 413.04 |
| 53 | E | 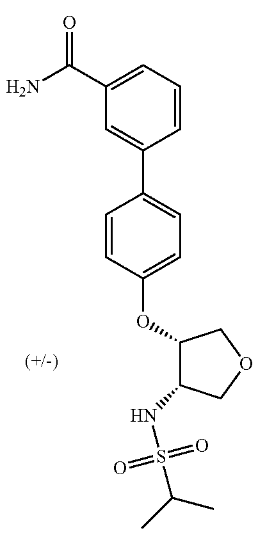 [SMILES: CC(C)S(=O)(=O)N[C@H]1COC[C@H]1Oc1ccc(-c2cccc(C(N)=O)c2)cc1] | cis-4'-({4-[(isopropylsulfonyl)amino]tetrahydrofuran-3-yl}oxy)biphenyl-3-carboxamide | 2.28[A] | 404.14 | 405.01 |

TABLE 2-continued

| Ex # | Method | Structure | IUPAC Name | Ret. Time (min.) | Mol. Wt. Calc. | Mass spec: Obs ion m/z (M + 1) |
|---|---|---|---|---|---|---|
| 54 | F | 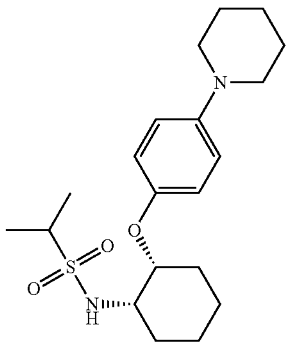 [SMILES: CC(C)S(=O)(=O)N[C@H]1CCCC[C@H]1Oc1ccc(N2CCCCC2)cc1] | N-[(1S,2R)-2-(4-piperidin-1-ylphenoxy)cyclohexyl]pro-pane-2-sulfonamide | 4.35$^B$ | 380.21 | 381.24 |

$^A$Column: Waters Sunfire C$_{18}$ 3.5 μm, 4.6 × 50 mm; Mobile phase A: 0.05% TFA in water;
Mobile phase B: 0.05% TFA in CH$_3$CN; Flow rate 2.0 mL/min.
GRADIENT:
0 minutes    5% B
4 minutes    95% B
5 minutes    95% B
$^B$Column: Waters Xterra C$_{18}$ 3.5 μm, 4.6 × 50 mm; Mobile phase A: 0.1% NH$_4$OH in water;
Mobile phase B: 0.1% NH$_4$OH in CH$_3$CN; Flow rate 2.0 mL/min.
GRADIENT:
0 minutes    5% B
5.83 minutes    95% B
9.0 minutes    95% B

BIOLOGICAL PROTOCOLS

Growth and Maintenance of ES Cells

Murine ES cell line E14, with a targeted mutation in the Sox1 gene and a neuroectodermal marker that offers G418 resistance when the Sox1 gene is expressed (Stem Cell Sciences, West Mains Road, Edinburgh, Scotland EH9 3JQ) may be used in all experiments. ES cells may be maintained undifferentiated as previously described (Methods For The Isolation And Maintenance Of Murine Embryonic Stem Cells; Roach-M-L, McNeish-J-D., Methods in Molecular Biology, 185, 1-16 (2002)). Briefly, ES cells may be grown in stem cell culture media comprising a base medium of Knockout™ D-MEM (Invitrogen 5791 Van Allen Way, Carlsbad, Calif. USA 92008), supplemented with 15% ES qualified Fetal Bovine Serum (FBS) (Invitrogen), 0.2 mM L-Glutamine (Invitrogen), 0.1 mM MEM non-essential amino acids (Invitrogen), 30 μg/ml Gentamicin (G418) (Invitrogen), 1000 U/ml ESGRO™ (CHEMICON International, Inc., 28820 Single Oak Drive, Temecula, Calif. 92590) and 0.1 mM 2-mercaptoethanol (Sigma, 3050 Spruce St., St. Louis, Mo. 63103). ES cells may then be plated on gelatin-coated dishes (BD Biosciences, 2350 Qume Drive, San Jose, Calif. 95131), wherein the media is changed daily and the cells dissociated with 0.05% Trypsin EDTA (Invitrogen) every other day.

Neural In Vitro Differentiation of ES Cells

Embryoid Body Formation: Prior to embryoid body (EB) formation the ES cells may be weaned from FBS onto Knockout Serum Replacement™ (KSR) (Invitrogen). To form EBs, ES cells may be dissociated into a single cell suspension, then 3×10$^6$ cells plated in bacteriology dishes (Nunc 4014) and grown as a suspension culture in NeuroEB-I medium that consisted of Knockout™ D-MEM (Invitrogen), supplemented with 10% KSR (Invitrogen), 0.2 mM L-Glutamine (Invitrogen), 0.1 mM MEM non-essential amino acids (Invitrogen), 30 μg/ml Gentamicin (Invitrogen), 1000 U/ml ESGRO™ (CHEMICON International, Inc.), 0.1 mM 2-mercaptoethanol (Sigma) and 150 ng/ml Transferrin (Invitrogen). The plates may then be put on a Stovall Belly Button™ shaker in an atmospheric oxygen incubator. The media may be changed on day 2 of EB formation with NeuroEB-I and on day 4 with NeuroEB-II (NeuroEB-I plus 1 μg/ml mNoggin (R&D Systems, 614 McKinley Place N.E. Minneapolis, Minn. 55413)

Neuronal Precursor Selection and Expansion: On day 5 of EB formation, EBs may be dissociated with 0.05% Trypsin EDTA, and 4×10$^6$ cells/100 mm dish may then be plated on Laminin coated tissue culture dishes in NeuroEB-II-G418 medium that consisted of a base medium of a 1:1 mixture of D-MEM/F12 supplemented with N2 supplements and NeuroBasal Medium supplemented with B27(I ASSUME THIS IS THE VITAMIN) supplement and 0.1 mM L-Glutamine (all from Invitrogen). The base medium may then be supplemented with 10 ng/ml bFGF (Invitrogen), 1 μg/ml mNoggin, 500 ng/ml SHH-N (IS THIS SONIC HEDGEHOG FROM ProSpecBio Rehovot Science Park, P.O. BOX 398, Rehovot 76103, Israel), 100 ng/ml FGF-8b (R&D Systems), 1 μg/ml Laminin and 200 μg/ml G418 (Invitrogen) for selection of neuronal precursors expressing Sox-1. The plates may then be put in an incubator containing 2% oxygen and maintained in these conditions. During the 6-day selection period, the NeuroEB-II (???) media should be changed daily. On day 6, the surviving neuronal precursor foci may then be dissociated with 0.05% Trypsin EDTA and the cells plated at a density of 1.5×10$^6$ cells/100 mm Laminin coated dish in NeuroII (??)-G418 medium. The cells may then be dissociated every other day for expansion, and prepared for cryopreservation at passage 3 or 4. The cryopreservation medium typically contains 50% KSR, 10% dimethyl sulfoxide (DMSO) (Sigma) and 40% NeuroI(???)-G418 medium. Neuronal precursors may be cryopreserved at a concentration of 4×10⁶ cells/ml and 1 ml/cryovial in a controlled rate freezer overnight then transferred to an ultra-low freezer or liquid nitrogen for long-term storage.

Neuronal Differentiation: Cryopreserved ES cell-derived neuronal precursors may be thawed by the rapid thaw method in a 37° C. water-bath. The cells are then transferred from the cryovial to a 100 mm Laminin coated tissue culture dish that already contains Neuro1l-G418 that has been equilibrated in a 2 percent oxygen incubator. The media is changed with fresh Neuro1l-G418 the next day. The cells may be dissociated every other day as described above for expansion to generate enough cells to plate for the screen. For the screen, the cells are plated into 384-well poly-d-lysine coated tissue culture dishes (BD Biosciences) by the automated SelecT® (The Automation Partnership York Way, Royston, Hertfordshire SG8 5WY UK) at a cell density of 6K cells/well in differentiation medium Neuronl that contains a 4:1 ratio of the NeuroBasalMedium/B27:D-MEM/F12/N2 supplemented with 1 µM cAMP (Sigma), 200 µM Ascorbic Acid (Sigma), 1 µg/ml Laminin (Invitrogen) and 10 ng/ml BDNF (R&D Systems, 614 McKinley Place N.E. Minneapolis, Minn. 55413). The plates are then put in an incubator with 2 percent oxygen and allowed to complete the differentiation process for 7 days. The cells could then be used over a 5-day period for the high throughput screen.

In vitro Assays

Procedure for AMPA ES Cell FLIPR Screen

On the day of the assay, the FLIPR assay may be performed using the following methods:

| Assay buffer: | | | |
|---|---|---|---|
| Compound | g/L | MW | [concentration] |
| NaCl | 8.47 | 58.44 | 145 mM |
| Glucose | 1.8 | 180.2 | 10 mM |
| KCl | .37 | 74.56 | 5 mM |
| MgSO₄ | 1 ml 1M Stock | 246.48 | 1 mM |
| HEPES | 2.38 | 238.3 | 10 mM |
| CaCl₂ | 2 ml 1M Stock | 110.99 | 2 mM |

The pH may be adjusted to 7.4 with 1M NaOH. Prepare a 2 mM (approx.) stock solution of Fluo-4 AM (Invitrogen) dye in DMSO-22 µl DMSO per 50 µg vial (440 µL per 1 mg vial). Make a 1 mM (approx.) Fluo-4 AM, PA working solution per vial by adding 22 µl of 20% pluronic acid (PA) (Invitrogen) in DMSO to each 50 µg vial (440 µL per 1 mg vial). Prepare a 250 mM Probenecid (Sigma) stock solution. Make 4 µM (approx.) dye incubation media by adding the contents of 2 50 µg vials per 11 ml DMEM high glucose without glutamine (220 ml DMEM per 1 mg vial). Add 110 µL probenecid stock per 11 ml media (2.5 mM final concentration). Dye concentrations ranging from 2 µM to 8 µM dye may be used without altering agonist or potentiator pharmacology. Add probenecid to the assay buffer used for cell washing (but not drug preparation) at 110 µl probenecid stock per 11 ml buffer.

Remove growth media from cell plates by flicking. Add 50 µl/well dye solution. Incubate 1 hour at 37° C. and 5% CO₂. Remove dye solution and wash 3 times with assay buffer+ probenecid (100 µl probenecid stock per 10 ml buffer), leaving 30 µL/well assay buffer. Wait at least 10-15 minutes. Compound and agonist challenge additions may be performed with the FLIPR (Molecular Devices, 1311 Orleans Ave, Sunnyvale, Calif. 94089). The first addition is for test compounds, which are added as 15 µL of a 4× concentration. The second addition is 15 µL of 4× concentration of agonist or challenge. This achieves 1× concentration of all compounds only after second addition. Compounds are pretreated at least 5 minutes before agonist addition.

Several baseline images are collected with the FLIPR before compound addition, and images are collected for least one minute after compound addition. Results are analyzed by subtracting the minimum fluorescent FLIPR value after compound or agonist addition from the peak fluorescent value of the FLIPR response after agonist addition to obtain the change in fluorescence. The change in fluorescence (RFUs, relative fluorescent units) are then analyzed using standard curve fitting algorithms. The negative control is defined by the AMPA challenge alone, and the positive control is defined by the AMPA challenge plus a maximal concentration of cyclothiazide (10 uM or 32 uM).

Compounds are delivered as DMSO stocks or as powders. Powders are solubilized in DMSO. Compounds are then added to assay drug buffer as 40 µL top [concentration] (4× the top screening concentration). The standard agonist challenge for this assay is 32 µM AMPA.

$EC_{50}$ values of the compounds of the invention are preferably 10 micromolar or less, more preferably 1 micromolar or less, even more preferably 100 nanomolar or less. The data for specific compounds of the invention is provided below in Table 3.

TABLE 3

| Ex. # | AMPA Potentiator Assay $EC_{50}$ (µM) |
|---|---|
| 1 | 3.33* |
| 2 | 1.36* |
| 3 | 0.0217 |
| 4 | 1.79* |
| 5 | 0.535 |
| 6 | 1.54* |
| 7 | 0.157 |
| 8 | 2.91 |
| 9 | 6.15* |
| 10 | 1.16* |
| 11 | 0.689 |
| 12 | 1.10 |
| 13 | 5.28 |
| 14 | 2.32 |
| 15 | 2.88 |
| 16 | <0.010 |
| 17 | 0.405* |
| 18 | 1.18 |
| 19 | 0.248 |
| 20 | 0.729 |
| 21 | 0.239 |
| 22 | 0.861 |
| 23 | 2.58* |
| 24 | 0.523 |
| 25 | 2.96* |
| 26 | 1.12* |
| 27 | 0.857* |
| 28 | 0.651* |
| 29 | 0.521 |
| 30 | 0.349 |
| 31 | 0.327 |
| 32 | 1.40 |
| 33 | 0.623* |
| 34 | 3.22 |
| 35 | 0.525 |
| 36 | 1.61 |
| 37 | 1.72 |
| 38 | 0.327 |
| 39 | 1.42* |
| 40 | 0.148 |
| 41 | 0.331 |
| 42 | 2.78 |
| 43 | 4.48* |
| 44 | 2.70* |

TABLE 3-continued

| Ex. # | AMPA Potentiator Assay EC$_{50}$ (µM) |
|---|---|
| 45 | 2.55* |
| 46 | 6.76 |
| 47 | 3.82* |
| 48 | 0.626* |
| 49 | 1.41 |
| 50 | 0.452* |
| 51 | 2.09 |
| 52 | 1.25* |
| 53 | 1.11 |
| 54 | 0.503 |

*Value represents the geometric mean of 2-5 EC$_{50}$ determinations

When introducing elements of the present invention or the exemplary embodiment(s) thereof, the articles "a," "an," "the" and "said" are intended to mean that there are one or more of the elements. The terms "comprising," "including" and "having" are intended to be inclusive and mean that there may be additional elements other than the listed elements. Although this invention has been described with respect to specific embodiments, the details of these embodiments are not to be construed as limitations to the invention, the scope of which is defined by the appended claims.

The invention claimed is:

1. A method for treating an AMPA receptor-mediated condition in a mammal selected from the group consisting of dementia, Alzheimer's disease, cognitive disorders, idiopathic and drug-induced Parkinson's disease, psychosis, schizophrenia, mood disorders, depression, attention deficit/hyperactivity disorder, and attention deficit disorder, comprising administering to the mammal a compound of formula I, or a pharmaceutically acceptable salt thereof,

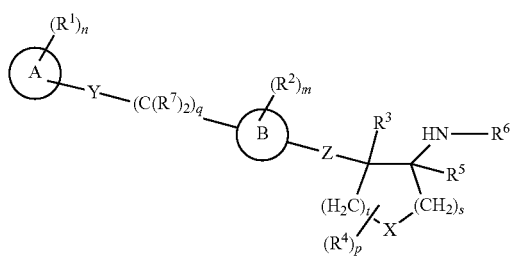

I wherein each $R^1$ and each $R^2$ is independently selected from the group consisting of hydrogen, halogen, hydroxyl, —CF$_3$, —CN, —(NR$^8$)—(C=O)—R$^8$, —(C=O)—OR$^8$, —(C=O)—N(R$^8$)$_2$, —OR$^8$, —N(R$^8$)$_2$, —SO$_2$—N(R$^8$)$_2$, and (C$_1$-C$_6$)alkyl; wherein said (C$_1$-C$_6$)alkyl is optionally substituted with one, two, three or four R$^9$;
m is zero, or one;
n is zero, one, two or three;
p is zero;
q is zero;
s is one and t is one; or one of s or t is one and the other of s or t is two;
$R^3$ is hydrogen;
each $R^4$ is hydrogen;
$R^5$ is hydrogen;
$R^6$ is (C$_1$-C$_6$)alkyl-SO$_2$;
$R^8$ is independently selected from the group consisting of hydrogen, (C$_1$-C$_6$)alkyl and (C$_3$-C$_{10}$)cycloalkyl;

wherein said (C$_1$-C$_6$)alkyl may be optionally substituted with one, two or three halo;
each $R^9$ is independently selected from the group consisting of halogen and (NR$^{10}$)—SO$_2$—R$^{10}$;
$R^{10}$ is independently selected from the group consisting of hydrogen and (C$_1$-C$_6$)alkyl;
ring "A" is (C$_6$-C$_{10}$)aryl, (C$_1$-C$_9$)heteroaryl, or (C$_1$-C$_9$)heterocycloalkyl; wherein two of said $R^1$ substituents on said (C$_1$-C$_9$)heterocycloalkyl may optionally be attached to the same carbon atom and may optionally be taken together to be oxo;
ring "B" is phenyl or pyridinyl;
"X" is —O— or >C(R$^4$)$_2$;
"Y" is absent; and
"Z" is —O.

2. The method of claim 1 wherein said compound is of Formula Ia:

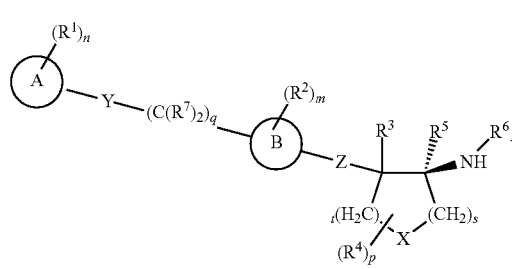

Ia

3. The method of claim 1 wherein said compound is of Formula Ib:

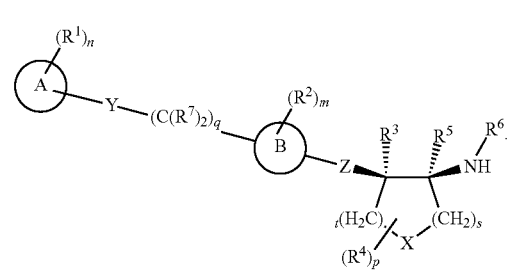

Ib

4. The method of claim 3 wherein X is —O—.

5. The method of claim 4 wherein ring "A" is phenyl.

6. The method of claim 5 wherein ring "A" is phenyl; n is zero, one or two; $R^1$ is selected from the group consisting of hydrogen, halogen, hydroxyl, —CF$_3$, —CN, —(NR$^8$)—(C=O)—R$^8$, —(C=O)—OR$^8$, —(C=O)—N(R$^8$)$_2$, —OR$^8$, —N(R$^8$)$_2$, —SO$_2$—N(R$^8$)$_2$, and (C$_1$-C$_6$)alkyl; wherein said (C$_1$-C$_6$)alkyl is optionally substituted with one, two, three or four R$^9$.

7. The method of claim 4 wherein ring "A" is (C$_1$-C$_9$)heteroaryl; n is zero, one or two; and wherein $R^1$ is selected from the group consisting of hydrogen, halogen, hydroxyl, —CF$_3$, —CN, —(NR$^8$)—(C=O)—R$^8$, —(C=O)—OR$^8$, —(C=O)—N(R$^8$)$_2$, —OR$^8$, —N(R$^8$)$_2$, —SO$_2$—N(R$^8$)$_2$, and (C$_1$-C$_6$)alkyl; wherein said (C$_1$-C$_6$)alkyl is optionally substituted with one, two, three or four R$^9$.

8. The method of claim 7 wherein $R^1$ is (C$_1$-C$_6$)alkoxy, (C$_1$-C$_6$)alkyl, cyano or halogen and is in the ortho or para position relative to Y.

9. The method of claim 4 wherein ring "B" is phenyl; n is zero or one; $R^2$ is hydrogen, halogen, hydroxyl, —$CF_3$, —CN, —($NR^8$)—(C=O)—$R^8$, —(C=O)—$OR^8$, —(C=O)—$N(R^8)_2$, —$OR^8$, —$N(R^8)_2$, —$SO_2$—$N(R^8)_2$, and ($C_1$-$C_6$)alkyl; wherein said ($C_1$-$C_6$)alkyl is optionally substituted with one, two, three or four $R^9$.

10. The method of claim 4 wherein ring "B" is pyridinyl; n is zero or one; and wherein $R^2$ is hydrogen, halogen, hydroxyl, —$CF_3$, —CN, —($NR^8$)—(C=O)—$R^8$, —(C=O)—$OR^8$, —(C=O)—$N(R^8)_2$, —$OR^8$, —$N(R^8)_2$, —$SO_2$—$N(R^8)_2$, and ($C_1$-$C_6$)alkyl; wherein said ($C_1$-$C_6$)alkyl is optionally substituted with one, two, three or four $R^9$.

11. The method of claim 9 wherein $R^2$ is hydrogen.

12. The method of claim 11 wherein $R^6$ is ($C_1$-$C_5$)alkyl-$SO_2$—.

13. A method for treating an AMPA receptor-mediated condition in a mammal selected from the group consisting of dementia, Alzheimer's disease, cognitive disorders, idiopathic and drug-induced Parkinson's disease, psychosis, schizophrenia, mood disorders, depression, attention deficit/hyperactivity disorder, and attention deficit disorder, comprising administering to the mammal a compound or a pharmaceutically acceptable salt thereof, to the mammal wherein the compound is:

N-{1-[4-trans-({4-[(isopropylsulfonyl)amino]tetrahydrofuran-3-yl}oxy)phenyl]pyrrolidin-3-yl}acetamide;

N-[(3S,4S)-4-(biphenyl-4-yloxy)tetrahydrofuran-3-yl]propane-2-sulfonamide;

N-{(3S,4S)-4-[(2'-cyanobiphenyl-4-yl)oxy]tetrahydrofuran-3-yl}propane-2-sulfonamide;

N-{(3S,4S)-4-[4-(5-cyano-2-thienyl)phenoxy]tetrahydrofuran-3-yl}propane-2-sulfonamide;

N-{(1S,2R)-2-[(2'-cyanobiphenyl-4-yl)oxy]cyclopentyl}propane-2-sulfonamide;

N-{(1S,2R)-2-[4-(5-cyano-2-thienyl)phenoxy]cyclopentyl}propane-2-sulfonamide;

N-{(1S,2R)-2-[(2'-cyanobiphenyl-4-yl)oxy]cyclohexyl}propane-2-sulfonamide;

cis-N-[4-(4-pyridin-3-ylphenoxy)tetrahydro furan-3-yl]propane-2-sulfonamide;

cis-N-{4-[4-(2-thienyl)phenoxy]tetrahydro furan-3-yl}propane-2-sulfonamide;

N-{(3S,4S)-4-[(2'-cyano-4'-fluoro biphenyl-4-yl)oxy]tetrahydrofuran-3-yl}propane-2-sulfonamide;

N-{(3S,4S)-4-[(4'-fluoro biphenyl-4-yl)oxy]tetra hydrofuran-3-yl}propane-2-sulfonamide;

N-{(3S,4S)-4-[(2'-ethoxy-4'-fluoro biphenyl-4-yl)oxy]tetra hydrofuran-3-yl}propane-2-sulfonamide;

cis-N-[4-{[6-(5-cyano-2-thienyl)pyridin-3-yl]oxy}tetra hydrofuran-3-yl]propane-2-sulfonamide;

cis-N-{4-[4-(3-thienyl)phenoxy]tetrahydro furan-3-yl}propane-2-sulfonamide;

2-cyano-4'-({(1R,2S)-2-[(isopropyl sulfonyl)amino]cyclopentyl}oxy)biphenyl-4-carboxylic acid;

N-{(1S,2R)-2-[(2'-cyano-2,4'-difluoro biphenyl-4-yl)oxy]cyclopentyl}propane-2-sulfonamide;

N-{(1S,2R)-2-[(2'-ethoxy-2-fluoro biphenyl-4-yl)oxy]cyclopentyl}propane-2-sulfonamide;

N-{(1S,2R)-2-[4-(5-cyano-2-thienyl)-3-fluoro phenoxy]cyclopentyl}propane-2-sulfonamide;

N-{(1S,2R)-2-[(2'-cyano-2-fluoro biphenyl-4-yl)oxy]cyclohexyl}propane-2-sulfonamide;

N-{(1S,2R)-2-[(2'-cyano-2,4'-difluoro biphenyl-4-yl)oxy]cyclohexyl}propane-2-sulfonamide;

N-{(1S,2R)-2-[4-(5-cyano-2-thienyl)-3-fluoro phenoxy]cyclohexyl}propane-2-sulfonamide;

N-[(1S,2R)-2-(4-pyrrolidin-1-ylphenoxy)cyclohexyl]propane-2-sulfonamide;

N-[(1S,2R)-2-({6-[2-(2,2,2-trifluoro ethoxy)phenyl]pyridin-3-yl}oxy)cyclohexyl]propane-2-sulfonamide;

N-[(1S,2R)-2-({6-[2-(trifluoro methoxy)phenyl]pyridin-3-yl]oxy)cyclohexyl}propane-2-sulfonamide; or N-[(1S,2R)-2-{[6-(5-cyano-2-thienyl)pyridin-3-yl]oxy}cyclohexyl]propane-2-sulfonamide.

14. The method of claim 13 wherein the condition is a cognitive disorder, schizophrenia, or depression.

15. The method of claim 13 wherein the compound or pharmaceutically acceptable salt thereof to be administered is N-{(3S,4S)-4-[4-(5-cyano-2-thienyl)phenoxy]tetrahydrofuran-3-yl}propane-2-sulfonamide.

16. The method of claim 15 wherein the condition is a cognitive disorder.

17. The method of claim 15 wherein the condition is schizophrenia.

18. The method of claim 15 wherein the condition is depression.

* * * * *